US012606570B2

(12) United States Patent
Liu et al.

(10) Patent No.: US 12,606,570 B2
(45) Date of Patent: Apr. 21, 2026

(54) DEUTERATED COMPOUNDS AND IMAGING AGENTS FOR IMAGING HUNTINGTIN PROTEIN

(71) Applicant: CHDI Foundation, Inc., New York, NY (US)

(72) Inventors: Longbin Liu, Thousand Oaks, CA (US); Celia Dominguez, Los Angeles, CA (US); Jonathan Bard, New York, NY (US); Vinod Khetarpal, Ambler, PA (US); Ashley Jarvis, Abingdon (GB); Sarah Hayes, Oxfordshire (GB); John E. Mangette, Town of Lancaster, NY (US)

(73) Assignee: CHDI Foundation, Inc., New York, NY (US)

( * ) Notice: Subject to any disclaimer, the term of this patent is extended or adjusted under 35 U.S.C. 154(b) by 866 days.

(21) Appl. No.: 17/729,881

(22) Filed: Apr. 26, 2022

(65) Prior Publication Data

US 2022/0372045 A1 Nov. 24, 2022

Related U.S. Application Data

(60) Provisional application No. 63/180,608, filed on Apr. 27, 2021.

(51) Int. Cl.
*C07D 498/04* (2006.01)
*A61K 51/04* (2006.01)

(52) U.S. Cl.
CPC ........ *C07D 498/04* (2013.01); *A61K 51/0455* (2013.01); *C07B 2200/05* (2013.01)

(58) Field of Classification Search
CPC .............. C07D 498/04; A61K 51/0455; C07B 2200/05
USPC .......................................................... 424/1.69
See application file for complete search history.

(56) References Cited

U.S. PATENT DOCUMENTS

| | | | | |
|---|---|---|---|---|
| 10,479,802 B2 * | 11/2019 | Dominguez | ......... | C07D 405/14 |
| 11,059,836 B2 * | 7/2021 | Dominguez | ......... | C07D 413/14 |
| 12,258,355 B2 | 3/2025 | Dominguez et al. | | |
| 2018/0344882 A1 * | 12/2018 | Wu | .................... | A61K 51/0453 |

FOREIGN PATENT DOCUMENTS

| | | | | |
|---|---|---|---|---|
| WO | WO-2016033445 A1 * | 3/2016 | ........... | A61B 5/0035 |
| WO | 2020176424 A1 | 9/2020 | | |

OTHER PUBLICATIONS

International Search Report and Written Opinion for International Application No. PCT/US2022/026313, Jul. 15, 2022, 12 pages.

Liu Longbin et al, "Imaging Mutant Huntingtin Aggregates: Development of a Potential PET Ligand", Journal of Medicinal Chemistry, vol. {0} 63, No. {0} 15, Jul. 14, 2020 (Jul. 14, 2020), p. 8608-8633

Fazio Patrik et al, "Novel Imaging Biomarkers for Huntington's Disease and Other Hereditary Choreas", Oct. 5, 2018 (Oct. 5, 2018), vol. {0} 18, No. {0} 12, p. 1-13.

Liu et al., "Design and Evaluation of [18F]CHDI-650 as a Positron Emission Tomography Ligand to Image Mutant Huntingtin Aggregates", Journal of Medicinal Chemistry, 2023, 66, 641-656.

* cited by examiner

*Primary Examiner* — Michael G. Hartley
*Assistant Examiner* — Sean R Donohue
(74) *Attorney, Agent, or Firm* — Sheppard Mullin Richter & Hampton LLP

(57) ABSTRACT

Provided herein are certain compounds and imaging agents useful for detecting a disease or condition associated with protein aggregation, compositions thereof, and methods of their use.

8 Claims, 2 Drawing Sheets

Specification includes a Sequence Listing.

Example 5-1

Example 1-1

DEUTERATED COMPOUNDS AND IMAGING AGENTS FOR IMAGING HUNTINGTIN PROTEIN

CROSS REFERENCE TO RELATED APPLICATIONS

This application claims priority to U.S. Provisional Application No. 63/180,608, filed Apr. 27, 2021, which is incorporated herein by reference for all purposes.

REFERENCE TO AN ELECTRONIC SEQUENCE LISTING

The contents of the electronic sequence listing submitted as ASCII format (333397.text; size 5,292 bytes; and Date of Creation Jan. 26, 2026) is herein incorporated by reference in its entirety.

FIELD

Provided herein are deuterated compounds and imaging agents useful for detecting, treating, or preventing a disease or condition associated with protein aggregation, compositions thereof, and methods of their use.

BACKGROUND

The advent of molecular imaging approaches such as positron emission tomography (PET) and single photon emission computed tomography (SPECT) has enabled non-invasive measurements of molecular and cellular mechanisms throughout the body in preclinical and clinical settings. Such measurements have widespread diagnostic utility, and their use for evaluation of treatment responses and to assist drug development is expanding rapidly.

Molecular probes labeled with positron-emitting radionuclides and associated PET imaging assays are under development to target, detect, visualize, and quantify various extracellular and intracellular molecules and processes associated with various diseases, especially neurodegenerative disorders where the pathology resides in the brain. One such disease is Huntington's disease (HD). HD is an inherited, progressive neurodegenerative disorder, characterized by motor, cognitive, and psychiatric deficits, as well as neurodegeneration and brain atrophy beginning in the striatum and the cortex, and extending to other subcortical brain regions. HD is caused by the expanded CAG trinucleotide repeat in the exon-1 region of the huntingtin gene (HTT). The resulting polyglutamate domain expansion may induce misfolding and conformational changes in the mutant huntingtin (mHTT) protein, leading to formation of protein aggregates. HD has a prevalence of 5-10 cases per 100,000 worldwide, which makes it the most common inherited and monogenic neurodegenerative disorder.

Consistent with other medical conditions, treatments for HD are ideally initiated at or before early signs of disease. Thus, early indicators of disease onset and reliable pharmacodynamic biomarkers of disease progression are highly desirable. Imaging methods such as PET may provide such indication.

PET involves the administration to a subject of a positron-emitting radionuclide tracer followed by detection of the positron emission (annihilation) events in the body. The radionuclide tracer is typically composed of a targeting molecule having incorporated therein one or more types of positron-emitting radionuclides.

A useful radionuclide for incorporation in PET tracers is fluorine-18, due to its long half-life (109.8 minutes), the availability of radiolabeled reagents, and the ease of installation of fluorine atoms. However, some fluorides are susceptible to metabolic cleavage in biological systems that lead to bone accumulation of fluorine-18 in the brain and interfere with PET imaging of surrounding tissues. Accordingly, there is a need for compounds and imaging agent incorporating fluorine-18 that are sufficiently stable in vivo during the imaging process.

SUMMARY

The present disclosure relates to compounds useful for imaging Huntingtin protein. Some embodiments provide for a compound as described herein, for example a compound of Formula I, Formula Ia, Formula Ib, Formula X, or any other Formula as described herein, wherein the compound is optionally labeled with one or more positron-emitting isotopes. The instant disclosure reveals that, in some instances, a fluorine atom such as an $^{18}F$ may be susceptible to environmental and/or metabolic cleavage in vivo. Thus, compounds described herein incorporate stabilizing functionality in the vicinity of an $^{18}F$, which reduces or prevents such cleavage. In specific embodiments, the compound includes a deuterated fluoroalkyl or deuterated fluoroalkoxy group.

In some embodiments, an imaging agent comprising the compound of Formula I, Formula La, or Formula Ib, or an isotopically enriched analog, pharmaceutically acceptable salt, prodrug, tautomer, stereoisomer, or a mixture of stercoisomers thereof, is provided. In some embodiments, the compound contains one or more positron-emitting isotopes selected from $^{11}C$, $^{13}N$, $^{15}O$, and $^{18}F$. In particular embodiments, the positron-emitting isotope is $^{18}F$. In some embodiments, the compound comprises deuterium at a position such that a fluorine atom is protected from environmental or metabolic cleavage in vivo.

Also provided are imaging agents comprising a compound described herein, wherein the compound is labeled with one or more positron-emitting radionuclides. In some embodiments, the compound contains one or more positron-emitting radionuclides selected from $^{11}C$, $^{13}N$, $^{15}O$, and $^{18}F$. Such compositions are useful as tracers in PET imaging.

Also provided is a method of detecting the presence or absence of a protein susceptible to aggregation in an individual comprising administering an effective amount of a compound described herein or an imaging agent comprising a compound described herein, and generating an image of a body part or body area of the individual. The method may further comprise detecting changes in distribution or amount of such protein, for example, in an individual subject over-time.

In some embodiments, provided is a compound or an imaging agent for use in detecting the presence or absence of a protein susceptible to aggregation in an individual, wherein the use comprises administering an effective amount of a compound or an imaging agent described herein to an individual, and generating an image of a body part or body area of the individual.

In some embodiments, provided is a compound or an imaging agent for use as described herein, wherein generating an image of a body part or body area of the individual comprises detecting the presence or absence of a protein susceptible to aggregation in the image. In some embodiments, provided is a compound or an imaging agent for use as described herein, wherein the protein susceptible to aggregation is huntingtin protein (HTT protein). In some embodiments, provided is a compound or an imaging agent for use as described herein, wherein the HTT protein is found in basal ganglia.

In some embodiments, provided is a compound or an imaging agent for use as described herein, wherein the presence or absence of a protein aggregate corresponds to the presence or absence of a neurodegenerative disease.

In some embodiments, provided is a compound or an imaging agent for use as described herein, wherein the neurodegenerative disease is selected from Alzheimer's disease, amyotrophic lateral sclerosis, Huntington's disease, Parkinson's disease, Prion disease, and spinocerebellar ataxias. In some embodiments, provided is a compound or an imaging agent for use as described herein, wherein the neurodegenerative disease is Huntington's disease (HD).

In some embodiments, provided is a compound or an imaging agent for use as described herein, wherein the effective amount of the imaging agent comprises from about 0.1 to about 20 mCi. In some embodiments, provided is a compound or an imaging agent for use as described herein, wherein the effective amount of the imaging agent comprises about 10 mCi.

In some embodiments, provided is a compound or an imaging agent for use as described herein, wherein generating an image comprises positron emission tomography (PET) imaging, PET with concurrent computed tomography imaging (PET/CT), PET with concurrent magnetic resonance imaging (PET/MRI), single-photon emission computed tomography (SPECT) imaging, or a combination thereof. In some embodiments, provided is a compound or an imaging agent for use as described herein, wherein generating an image comprises PET imaging.

In some embodiments, provided is a compound or an imaging agent for use as described herein, wherein the HTT protein is present as oligomers or aggregates, or a combination thereof. In some embodiments, provided is a compound or an imaging agent for use as described herein, wherein the HTT protein is mutant.

In some embodiments, provided is a compound or an imaging agent for use as described herein, wherein the body part or body area is head, spinal cord, limb, thorax, or abdomen. In some embodiments, provided is a compound or an imaging agent for use as described herein, wherein the body part or body area is brain.

DETAILED DESCRIPTION

Figure 1:
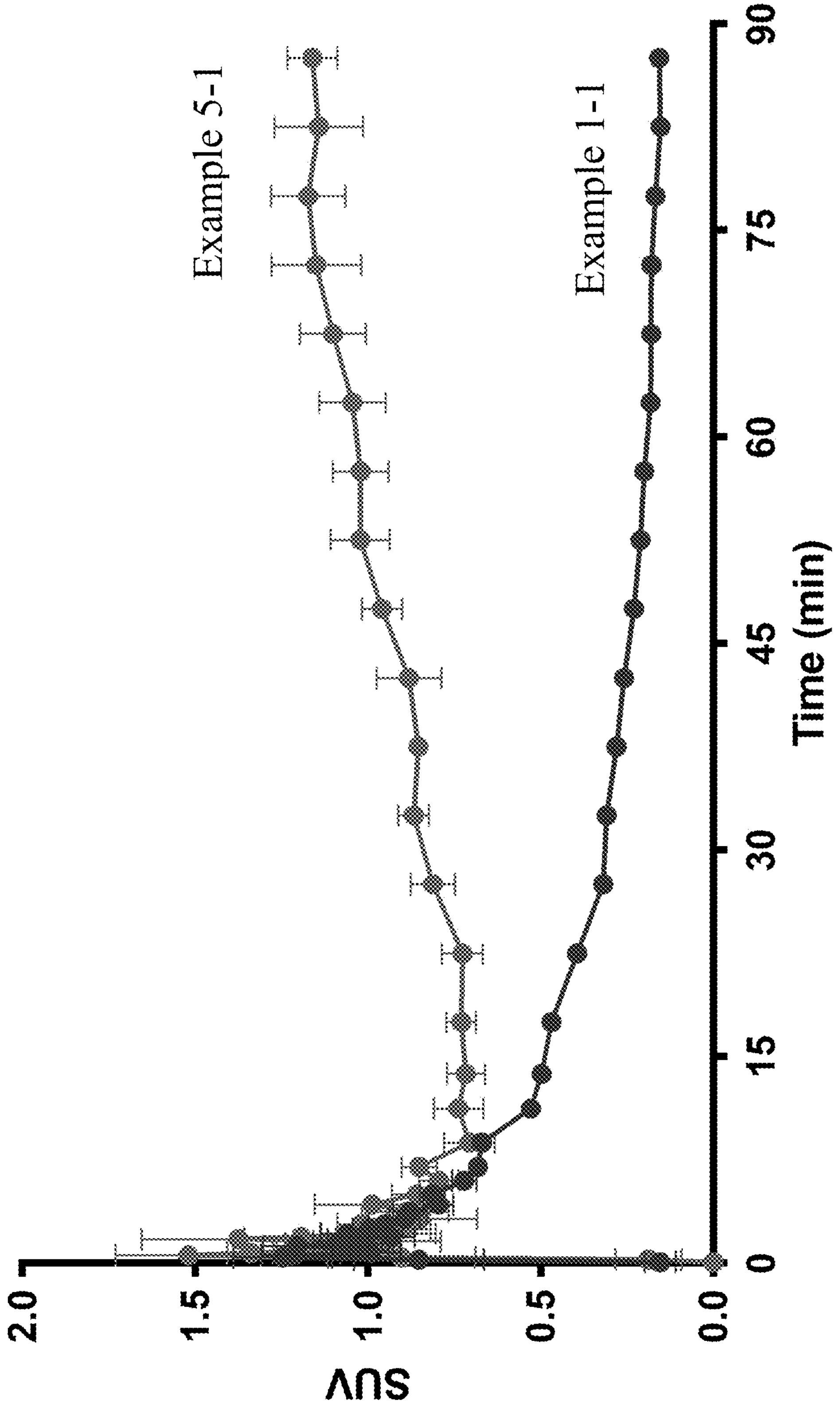
FIG. 1 depicts a comparison of Compound 1-1 and Compound 5-1 bone uptake of fluorine-18 following administration.

The following description sets forth exemplary embodiments of the present technology. It should be recognized, however, that such description is not intended as a limitation on the scope of the present disclosure, but is instead provided as a description of exemplary embodiments.

Definitions

As used in the present specification, the following words, phrases and symbols are generally intended to have the meanings as set forth below, except to the extent that the context in which they are used indicates otherwise.

A compound described herein refers to a compound, or an isotopically labeled analog, pharmaceutically acceptable salt, solvate, prodrug, stereoisomer, or mixture of stereoisomers thereof, of any formula described herein, including those of Formula I, Ia, Ib, II, III, IV, V, VI, VII, X, XI, XII, XIII, XIV, XV, XVI, XVII, XVIII, or XIX, or a compound described anywhere herein including the Examples, or a compound of Table 1 or a labeled isomer of such compound as defined herein, or an imaging agent or pharmaceutical composition comprising such compound or labeled compound.

A dash ("-") that is not between two letters or symbols is used to indicate a point of attachment to a parent structure for a substituent. For example, $-C(O)NH_2$ is attached to a parent structure through the carbon atom. A dash at the front or end of a chemical group is a matter of convenience; chemical groups may be depicted with or without one or more dashes without losing their ordinary meaning. A wavy line drawn through a bond in a structure indicates a specified point of attachment. Unless chemically or structurally required, no directionality or stereochemistry is indicated or implied by the order in which a chemical group is written or named.

The prefix "$C_{u-v}$" indicates that the following group has from u to v carbon atoms, exclusive of further substitution. For example, "$C_{1-6}$ alkyl" indicates an alkyl group having from 1 to 6 carbon atoms.

Reference to "about" a value or parameter herein includes (and describes) embodiments that are directed to that value or parameter per se. In certain embodiments, the term "about" includes the indicated amount ±10%. In other embodiments, the term "about" includes the indicated amount ±5%. In certain other embodiments, the term "about" includes the indicated amount ±1%. Also, to the term "about X" includes description of "X". Also, the singular forms "a" and "the" include plurals thereof unless the context clearly dictates otherwise. Thus, e.g., reference to "the compound" includes a plurality of such compounds and reference to "the assay" includes reference to one or more assays and equivalents thereof known to those skilled in the art.

"Alkyl" refers to an unbranched or branched saturated hydrocarbon chain. As used herein, alkyl has 1 to 20 carbon atoms (i.e., $C_{1-20}$ alkyl), 1 to 12 carbon atoms (i.e., $C_{1-12}$ alkyl), 1 to 9 carbon atoms (i.e., $C_{1-9}$ alkyl), 1 to 8 carbon atoms (i.e., $C_{1-8}$ alkyl), 1 to 6 carbon atoms (i.e., $C_{1-6}$ alkyl), or 1 to 4 carbon atoms (i.e., $C_{1-4}$ alkyl). Examples of alkyl groups include, e.g., methyl, ethyl, propyl, isopropyl, n-butyl, sec-butyl, iso-butyl, tert-butyl, pentyl, 2-pentyl, isopentyl, neopentyl, hexyl, 2-hexyl, 3-hexyl and 3-methylpentyl. When an alkyl residue having a specific number of carbons is named by chemical name or identified by molecular formula, all positional isomers having that number of carbons may be encompassed; thus, for example, "butyl" includes n-butyl (i.e., $-(CH_2)_3CH_3$), sec-butyl (i.e., $-CH(CH_3)CH_2CH_3$), isobutyl (i.e., $-CH_2CH(CH_3)_2$) and tert-butyl (i.e., $-C(CH_3)_3$); and "propyl" includes n-propyl (i.e., $-(CH_2)_2CH_3$) and isopropyl (i.e., $-CH(CH_3)_2$).

Alternative chemical names known to those of skill in the art may be used in lieu of the terms provided herein. For example, a divalent group such as a divalent "alkyl" group, a divalent "aryl" group, etc., may also be referred to as an "alkylene" or an "arylene" group, respectively. Also, unless indicated explicitly otherwise (for example, by a dash), where combinations of groups are referred to herein as one moiety, e.g., arylalkyl or aralkyl, the last mentioned group contains the atom by which the moiety is attached to the rest of the molecule.

"Alkenyl" refers to a hydrocarbon group containing at least one carbon-carbon double bond and having from 2 to 20 carbon atoms (i.e., $C_{2-20}$ alkenyl), 2 to 8 carbon atoms (i.e., $C_{2-8}$ alkenyl), 2 to 6 carbon atoms (i.e., $C_{2-6}$ alkenyl), or 2 to 4 carbon atoms (i.e., $C_{2-4}$ alkenyl). Examples of alkenyl groups include, e.g., ethenyl, propenyl, butadienyl (including 1,2-butadienyl and 1,3-butadienyl), and isoprenyl. Alkenyl groups also include "fluoroalkenyl" which refers to an alkenyl group including a carbon atom substituted by at least one fluorine atom. A "primary fluoroalkenyl" is a fluoroalkenyl including a saturated, primary carbon atom substituted by a fluorine atom.

"Alkynyl" refers to an hydrocarbon group containing at least one carbon-carbon triple bond and having from 2 to 20 carbon atoms (i.e., $C_{2-20}$ alkynyl), 2 to 8 carbon atoms (i.e., $C_{2-8}$ alkynyl), 2 to 6 carbon atoms (i.e., $C_{2-6}$ alkynyl), or 2 to 4 carbon atoms (i.e., $C_{2-4}$ alkynyl). The term "alkynyl" also includes those groups having a triple bond and a double bond. Alkynyl groups also include "fluoroalkynyl" which refers to an alkynyl group including a carbon atom substituted by at least one fluorine atom. A "primary fluoroalkynyl" is a fluoroalkynyl including a saturated, primary carbon atom substituted by a fluorine atom.

"Alkoxy" refers to a group "alkyl-O—". Examples of alkoxy groups include, e.g., methoxy, ethoxy, n-propoxy, iso-propoxy, n-butoxy, tert-butoxy, sec-butoxy, n-pentoxy, n-hexoxy, and 1,2-dimethylbutoxy.

"Alkylamino" refers to a group "alkyl-NH—". Examples of alkylamino groups include, e.g., methylamino, ethylamino, iso-propylamino, tert-butylamino, and n-hexylamino. "Dialkylamino" refers to a group "$(alkyl)_2N$—". Examples of dialkylamino groups include, e.g., dimethylamino, diethylamino, (iso-propyl)(methyl)amino, (n-pentyl)(tert-butyl)amino, and di-n-hexylamino.

"Alkylthio" refers to a group "alkyl-S—". "Alkylsulfinyl" refers to the group "alkyl-S(O)—". "Alkylsulfonyl" refers to a group "alkyl-$S(O)_2$—". "Alkylsulfonylalkyl" refers to -alkyl-$S(O)_2$-alkyl.

"Acyl" refers to a group —C(O)$R^y$, wherein $R^y$ is hydrogen, alkyl, alkenyl, alkynyl, cycloalkyl, heterocyclyl, aryl, heteroalkyl or heteroaryl; each of which may be optionally substituted, as defined herein. Examples of acyl include, e.g., formyl, acetyl, cyclohexylcarbonyl, cyclohexylmethylcarbonyl and benzoyl.

"Amido" refers to both a "C-amido" group, which refers to a group —C(O)$NR^yR^z$, and an "N-amido" group, which refers to a group —$NR^y$C(O)$R^z$, wherein $R^y$ and $R^z$ are independently hydrogen, alkyl, alkenyl, alkynyl, haloalkyl, cycloalkyl, heterocyclyl, aryl, heteroalkyl, or heteroaryl; each of which may be optionally substituted, as defined herein, or $R^y$ and $R^z$ are taken together to form a cycloalkyl or heterocyclyl; each of which may be optionally substituted, as defined herein.

"Amino" refers to a group —$NR^yR^z$ wherein $R^y$ and $R^z$ are independently hydrogen, alkyl, alkenyl, alkynyl, haloalkyl, cycloalkyl, heterocyclyl, aryl, heteroalkyl, or heteroaryl; each of which may be optionally substituted, as defined herein. In some embodiments, "amino" refers to a group $NH_2$.

"Amidino" refers to a group —C(=$NR^y$)$NR^z_2$, wherein $R^y$ and $R^z$ are independently hydrogen, alkyl, alkenyl, alkynyl, haloalkyl, cycloalkyl, heterocyclyl, aryl, heteroalkyl, or heteroaryl; each of which may be optionally substituted, as defined herein.

"Aryl" refers to an aromatic carbocyclic group having a single ring (e.g., monocyclic) or multiple rings (e.g., bicyclic or tricyclic) including fused systems. As used herein, aryl has 6 to 20 ring carbon atoms (i.e., $C_{6-20}$ aryl) or 6 to 10 carbon ring atoms (i.e., $C_{6-10}$ aryl). Examples of aryl groups include, e.g., phenyl, naphthyl, fluorenyl, and anthryl. Aryl, however, does not encompass or overlap in any way with heteroaryl defined below. If one or more aryl groups are fused with a heteroaryl, the resulting ring system is heteroaryl. If one or more aryl groups are fused with a heterocyclyl, the resulting ring system is heterocyclyl.

"Arylalkyl" or "Aralkyl" refers to a group "aryl-alkyl-".

"Carbamoyl" refers to both an "O-carbamoyl" group, which refers to a group —O—C(O)$NR^yR^z$, and an "N-carbamoyl" group, which refers to a group —$NR^y$C(O)O$R^z$, wherein $R^y$ and $R^z$ are independently hydrogen, alkyl, alkenyl, alkynyl, haloalkyl, cycloalkyl, heterocyclyl, aryl, heteroalkyl, or heteroaryl; each of which may be optionally substituted, as defined herein.

"Carboxyl ester" or "ester" refer to both —OC(O)$R^x$ and —C(O)O$R^x$, wherein $R^x$ is alkyl, alkenyl, alkynyl, haloalkyl, cycloalkyl, heterocyclyl, aryl, heteroalkyl, or heteroaryl; each of which may be optionally substituted, as defined herein.

"Cycloalkyl" refers to a saturated or partially unsaturated cyclic alkyl group having a single ring or multiple rings including fused, bridged, and spiro ring systems. The term "cycloalkyl" includes cycloalkenyl groups (i.e., the cyclic group having at least one double bond) and carbocyclic fused ring systems having at least one $sp^3$ ring carbon atom (i.e., at least one non-aromatic ring). As used herein, cycloalkyl has from 3 to 20 ring carbon atoms (i.e., $C_{3-20}$ cycloalkyl), 3 to 12 ring carbon atoms (i.e., $C_{3-12}$ cycloalkyl), 3 to 10 ring carbon atoms (i.e., $C_{3-10}$ cycloalkyl), 3 to 8 ring carbon atoms (i.e., $C_{3-8}$ cycloalkyl), or 3 to 6 ring carbon atoms (i.e., $C_{3-6}$ cycloalkyl). Monocyclic groups include, for example, cyclopropyl, cyclobutyl, cyclopentyl, cyclohexyl, cyclohexenyl, cycloheptyl and cyclooctyl. Polycyclic groups include, for example, bicyclo[2.2.1]heptanyl, bicyclo[2.2.2]octanyl, adamantyl, norbornyl, norbornenyl, decalinyl, 7,7-dimethyl-bicyclo[2.2.1]heptanyl and the like. Further, the term cycloalkyl is intended to encompass any non-aromatic ring system which may include a fused aryl ring, regardless of the attachment to the remainder of the molecule. Still further, cycloalkyl also includes "spirocycloalkyl," for example spiro[2.5]octanyl, spiro[4.5]decanyl, or spiro[5.5]undecanyl. When there are two positions for substitution on a carbon atom in a parent structure, cycloalkyl as a substituent group may include spirocycloalkyl. A cycloalkyl may be substituted at its carbon atom of attachment to a parent structure.

"Cycloalkoxy" refers to a group "—O-cycloalkyl."

"Cycloalkylalkyl" refers to a group "cycloalkyl-alkyl-".

"Guanidino" refers to —$NR^y$C(=$NR^z$)$NR^yR^z$, wherein each $R^y$ and $R^z$ are independently hydrogen, alkyl, alkenyl, alkynyl, haloalkyl, cycloalkyl, heterocyclyl, aryl, heteroalkyl, or heteroaryl; each of which may be optionally substituted, as defined herein.

"Imino" refers to a group —C(=$NR^y$)$R^z$, wherein $R^y$ and $R^z$ are each independently hydrogen, alkyl, alkenyl, alkynyl, haloalkyl, cycloalkyl, heterocyclyl, aryl, heteroalkyl, or heteroaryl; each of which may be optionally substituted, as defined herein.

"Imido" refers to a group —C(O)$NR^y$C(O)R, wherein $R^y$ and $R^z$ are each independently hydrogen, alkyl, alkenyl, alkynyl, haloalkyl, cycloalkyl, heterocyclyl, aryl, heteroalkyl, or heteroaryl; each of which may be optionally substituted, as defined herein.

"Halogen" or "halo" refers to a substituent atom of group VIIA of the periodic table, such as fluoro, chloro, bromo, or iodo.

"Haloalkyl" refers to an unbranched or branched alkyl group as defined above, wherein one or more (e.g., 1 to 6 or 1 to 3) hydrogen atoms, up to and including all hydrogen atoms, are replaced by a halogen. For example, where a residue is substituted with more than one halogen, it may be referred to by using a prefix corresponding to the number of halogen moieties attached. Dihaloalkyl and trihaloalkyl refer to alkyl substituted with two ("di") or three ("tri") halo groups, which may be, but are not necessarily, the same halogen. A perhaloalkyl group is a haloalkyl group in which every hydrogen substituent is replaced by halo. Examples of haloalkyl include, e.g., trifluoromethyl, difluoromethyl, fluoromethyl, trichloromethyl, 2,2,2-trifluoroethyl, 1,2-difluoroethyl, 3-bromo-2-fluoropropyl, 1,2-dibromoethyl, and the like. Haloalkyl groups also include "fluoroalkyl" which refers to an alkyl group substituted by at least one fluorine atom. A "primary fluoroalkyl" is a fluoroalkyl including a primary carbon atom substituted by a fluorine atom. A "deuterated haloalkyl" refers to a haloalkyl group substituted by at least one deuterium atom.

"Haloalkoxy" refers to an alkoxy group as defined above, wherein one or more (e.g., 1 to 6 or 1 to 3) hydrogen atoms, up to and including all hydrogen atoms, are replaced by a halogen. Haloalkoxy groups also include "fluoroalkoxy" which refers to an alkoxy group substituted by at least one fluorine atom. A "primary fluoroalkoxy" is a fluoroalkoxy including a primary carbon atom substituted by a fluorine atom. A "deuterated haloalkoxy" refers to a haloalkoxy group substituted by at least one deuterium atom.

"Hydroxyalkyl" refers to an alkyl group as defined above, wherein one or more (e.g., 1 to 6 or 1 to 3) hydrogen atoms are replaced by a hydroxy group.

"Heteroalkyl" refers to an alkyl group in which one or more of the carbon atoms of the alkyl chain (and any associated hydrogen atoms) are each independently replaced with the same or different heteroatomic group, provided the point of attachment to the remainder of the molecule is through a carbon atom. The term "heteroalkyl" includes unbranched or branched saturated chains having carbon and heteroatoms. By way of example, 1, 2, or 3 carbon atoms may be independently replaced with the same or different heteroatomic group. Heteroatomic groups include, but are not limited to, $—NR^y—$, $—C(O)NR^y—$, $—NR^yC(O)—$, $—O—$, $—S—$, $—S(O)—$, and $—S(O)_2—$, wherein $R^y$ is hydrogen, alkyl, alkenyl, alkynyl, haloalkyl, cycloalkyl, heterocyclyl, aryl, heteroalkyl, or heteroaryl; each of which may be optionally substituted, as defined herein. Examples of heteroalkyl groups include, e.g., ethers (e.g., $—CH_2OCH_3$, $—CH(CH_3)OCH_3$, $—CH_2CH_2OCH_3$, $—CH_2CH_2OCH_2CH_2OCH_3$, etc.), thioethers (e.g., $—CH_2SCH_3$, $—CH(CH_3)SCH_3$, $—CH_2CH_2SCH_3$, $—CH_2CH_2SCH_2CH_2SCH_3$, etc.), sulfones (e.g., $—CH_2S(O)_2CH_3$, $—CH(CH_3)S(O)_2CH_3$, $—CH_2CH_2S(O)_2CH_3$, $—CH_2CH_2S(O)_2CH_2CH_2OCH_3$, etc.), and aminoalkyls (e.g., $—CH_2NR^yCH_3$, $—CH(CH_3)NR^yCH_3$, $—CH_2CH_2NR^yCH_3$, $—CH_2CH_2NR^yCH_2CH_2NR^yCH_3$, etc., where $R^y$ is hydrogen, alkyl, alkenyl, alkynyl, haloalkyl, cycloalkyl, heterocyclyl, aryl, heteroalkyl, or heteroaryl; each of which may be optionally substituted, as defined herein). As used herein, heteroalkyl includes 1 to 10 carbon atoms, 1 to 8 carbon atoms, or 1 to 4 carbon atoms; and 1 to 3 heteroatoms, 1 to 2 heteroatoms, or 1 heteroatom.

"Heteroaryl" refers to an aromatic group having a single ring or multiple fused rings, with one or more ring heteroatoms independently selected from nitrogen, oxygen, and sulfur, and may comprise one or more (e.g., 1 to 3)N-oxide (—O—) moieties. As used herein, heteroaryl includes 1 to 20 ring carbon atoms (i.e., $C_{1-20}$ heteroaryl), 3 to 12 ring carbon atoms (i.e., $C_{3-12}$ heteroaryl), or 3 to 8 carbon ring atoms (i.e., $C_{3-8}$ heteroaryl), and 1 to 5 ring heteroatoms, 1 to 4 ring heteroatoms, 1 to 3 ring heteroatoms, 1 to 2 ring heteroatoms, or 1 ring heteroatom independently selected from nitrogen, oxygen, and sulfur. In certain instances, heteroaryl includes 5-10 membered ring systems, 5-7 membered ring systems, or 5-6 membered ring systems, each independently having 1 to 4 ring heteroatoms, 1 to 3 ring heteroatoms, 1 to 2 ring heteroatoms, or 1 ring heteroatom independently selected from nitrogen, oxygen, and sulfur. Examples of heteroaryl groups include, e.g., acridinyl, benzimidazolyl, benzothiazolyl, benzindolyl, benzofuranyl, benzothiazolyl, benzothiadiazolyl, benzonaphthofuranyl, benzoxazolyl, benzothienyl (benzothiophenyl), benzotriazolyl, imidazo[1,2-a]pyridyl, carbazolyl, cinnolinyl, dibenzofuranyl, dibenzothiophenyl, furanyl, isothiazolyl, imidazolyl, indazolyl, indolyl, indazolyl, isoindolyl, isoquinolyl, isoxazolyl, naphthyridinyl, oxadiazolyl, oxazolyl, 1-oxidopyridinyl, 1-oxidopyrimidinyl, 1-oxidopyrazinyl, 1-oxidopyridazinyl, phenazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, thiazolyl, thiadiazolyl, triazolyl, tetrazolyl and triazinyl. Examples of the fused-heteroaryl rings include, but are not limited to, benzo[d]thiazolyl, quinolinyl, isoquinolinyl, benzo[b]thiophenyl, indazolyl, benzo[d]imidazolyl, pyrazolo[1,5-a]pyridinyl and imidazo[1,5-a]pyridinyl, where the heteroaryl can be bound via either ring of the fused system. Any aromatic ring system, having a single or multiple fused rings containing at least one ring heteroatom, is considered a heteroaryl regardless of the attachment to the remainder of the molecule (i.e., through any one of the fused rings). Heteroaryl does not encompass or overlap with aryl as defined above.

"Heteroarylalkyl" refers to a group "heteroaryl-alkyl-".

"Heterocyclyl" refers to a saturated or partially unsaturated cyclic alkyl group, with one or more ring heteroatoms independently selected from nitrogen, oxygen, and sulfur, wherein the nitrogen or sulfur atoms are optionally oxidized to form an N-oxide, a sulfinyl (—S(O)—), or a sulfoxide ($—S(O)_2—$). The term "heterocyclyl" includes heterocycloalkenyl groups (i.e., a heterocyclyl group having at least one double bond), bridged-heterocyclyl groups, fused-heterocyclyl groups, spiro-heterocyclyl, and oxo-heterocyclyl groups. A heterocyclyl may be a single ring or multiple rings, wherein the multiple rings may be fused, bridged, or spiro. Regardless of substituent groups listed, a heterocyclyl may comprise one or more (e.g., 1 to 3) oxo (=O) or N-oxide ($—O^-$) moieties unless stated otherwise. A heterocyclyl can be bound through a carbon atom or a heteroatom as valency permits. Further, the term heterocyclyl encompasses any ring system including a non-aromatic ring or ring system containing at least one heteroatom, which ring may be fused to an aryl or heteroaryl ring, regardless of the attachment to the remainder of the molecule. A heterocyclyl may have a charged resonance structure that is aromatic (e.g., pyridin-2(1H)-on-1-yl). As used herein, a heterocyclyl may include 3 to 14 ring atoms, 3 to 10 ring atoms, 3 to 6 ring atoms, or 5 to 6 ring atoms, and/or 2 to 12 ring carbon atoms (i.e., $C_{2-12}$ heterocyclyl), 2 to 10 ring carbon atoms (i.e., $C_{2-10}$ heterocyclyl), 2 to 8 ring carbon atoms (i.e., $C_{2-8}$ heterocyclyl), 3 to 12 ring carbon atoms (i.e., $C_{3-12}$ heterocyclyl), 3 to 8 ring carbon atoms (i.e., $C_{3-8}$ heterocyclyl), or 3 to 6 ring carbon atoms (i.e., $C_{3-6}$ heterocyclyl); having 1 to 5 ring heteroatoms, 1 to 4 ring heteroatoms, 1 to 3 ring heteroatoms, 1 to 2 ring heteroatoms, or 1 ring heteroatom. Examples of heterocyclyl groups include, e.g., azetidinyl, azepinyl, benzodioxolyl, benzo[b][1,4]dioxepinyl, 1,4-benzodioxanyl, benzopyranyl, benzodioxinyl, benzopyranonyl, benzofuranonyl, dioxolanyl, dihydropyranyl, hydropyranyl, thienyl[1,3]dithianyl, decahydroisoquinolyl, furanonyl, imidazolinyl, imidazolidinyl, indolinyl, indolizinyl, isoindolinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, oxiranyl, oxetanyl, phenothiazinyl, phenoxazinyl, piperidinyl, piperazinyl, 4-piperidonyl, pyrrolidinyl, pyrazolidinyl, quinuclidinyl, thiazolidinyl, tetrahydrofuryl, tetrahydropyranyl, trithianyl, tetrahydroquinolinyl, thiophenyl (i.e., thienyl), tetrahydropyranyl, thiomorpholinyl, thiamorpholinyl, 1-oxo-thiomorpholinyl and 1,1-dioxo-thiomorpholinyl. The term "heterocyclyl" also includes "spiro-heterocyclyl." Examples of the spiro-heterocyclyl rings include, e.g., bicyclic and tricyclic ring systems, such as 2-oxa-7-azaspiro[3.5]nonanyl, 2-oxa-6-azaspiro[3.4]octanyl and 6-oxa-1-azaspiro[3.3]heptanyl. When there are two positions for substitution on a carbon atom in a parent structure, heterocyclyl as a substituent group may include spiro-heterocyclyl. Examples of bridged-heterocyclyl rings include, but are not limited to, 2,5-diazabicyclo[2.2.1]heptane, 2-oxa-5-azabicyclo[2.2.1]heptanyl. Examples of the fused-heterocyclyl rings include, but are not limited to, 1,2,3,4-tetrahydroisoquinolinyl, 4,5,6,7-tetrahydrothieno[2,3-c]pyridinyl, indolinyl and isoindolinyl, where the heterocyclyl can be bound via either ring of the fused system. An "oxo-heterocyclyl" group is a heterocyclyl including at least one oxo substituent (e.g., 1, or 1 to 2 oxo substituents), whether or not additional substituents are permitted (i.e., an unsubstituted oxo-heterocyclyl includes an oxo and no other substitution). In some embodiments, an oxo-heterocyclyl includes a cyclic amide moiety.

"Heterocyclylalkyl" refers to a group "heterocyclyl-alkyl-."

"Oxime" refers to a group —CRY(=NOH) wherein $R^y$ is hydrogen, alkyl, alkenyl, alkynyl, haloalkyl, cycloalkyl, heterocyclyl, aryl, heteroalkyl, or heteroaryl; each of which may be optionally substituted, as defined herein.

"Sulfonyl" refers to a group $—S(O)_2R^y$, where $R^y$ is hydrogen, alkyl, alkenyl, alkynyl, haloalkyl, cycloalkyl, heterocyclyl, aryl, heteroalkyl, or heteroaryl; each of which may be optionally substituted, as defined herein. Examples of sulfonyl are methylsulfonyl, ethylsulfonyl, phenylsulfonyl, and toluenesulfonyl.

"Sulfinyl" refers to a group $—S(O)R^y$, where $R^y$ is hydrogen, alkyl, alkenyl, alkynyl, haloalkyl, cycloalkyl, heterocyclyl, aryl, heteroalkyl, or heteroaryl; each of which may be optionally substituted, as defined herein. Examples of sulfinyl are methylsulfinyl, ethylsulfinyl, phenylsulfinyl, and toluenesulfinyl.

"Sulfonamido" refers to the groups $—SO_2NR^yR^z$ and $—NR^ySO_2R^z$, where $R^y$ and $R^z$ are each independently hydrogen, alkyl, alkenyl, alkynyl, haloalkyl, cycloalkyl, heterocyclyl, aryl, heteroalkyl, or heteroaryl; each of which may be optionally substituted, as defined herein.

The terms "optional" or "optionally" means that the subsequently described event or circumstance may or may not occur and that the description includes instances where said event or circumstance occurs and instances in which it does not. Also, the term "optionally substituted" refers to a group which is unsubstituted or substituted.

The term "substituted" used herein refers to a group in which any one or more (e.g., 1 to 5 or 1 to 3) hydrogen atoms is replaced by a non-hydrogen group such as, but not limited to alkyl, alkenyl, alkynyl, alkoxy, alkylthio, acyl, amido, amino, amidino, aryl, arylalkyl, azido, carbamoyl, carboxyl, carboxyl ester, cyano, cycloalkyl, cycloalkylalkyl, guanidino, halo, haloalkyl, haloalkoxy, hydroxyalkyl, heteroalkyl, heteroaryl, heteroarylalkyl, heterocyclyl, heterocyclylalkyl, $—NHNH_2$, $=NNH_2$, imino, imido, hydroxy, oxo, oxime, nitro, sulfonyl, sulfinyl, alkylsulfonyl, alkylsulfinyl, thiocyanate, —S(O)OH, $—S(O)_2OH$, sulfonamido, thiol, thioxo, N-oxide or $—Si(R^y)_3$, wherein each $R^y$ is independently hydrogen, alkyl, alkenyl, alkynyl, haloalkyl, heteroalkyl, cycloalkyl, aryl, heteroaryl, or heterocyclyl.

In certain embodiments, "substituted" refers to a group in which one or more (e.g., 1 to 5 or 1 to 3) hydrogen atoms are independently replaced with deuterium, halo, cyano, hydroxyl, imino, nitro, azido, oxo, thioxo, alkyl, alkenyl, alkynyl, haloalkyl, alkoxy, thioalkyl, haloalkoxy, cycloalkyl, heterocyclyl, N-heterocyclyl, heterocyclylalkyl, aryl, arylalkyl, heteroaryl, heteroarylalkyl, $—NR^gR^h$, $—NR^gC(=O)R^h$, $—NR^gC(=O)NR^gR^h$, $—NR^gC(=O)OR^h$, $—NR^gS(=O)_{1-2}R^h$, $—C(=O)R^g$, $—C(=O)OR^g$, $—OC(=O)OR^g$, $—OC(=O)R^g$, $—C(=O)NR^gR^h$, $—OC(=O)NR^gR^h$, $—OR^g$, $—SR^g$, $—S(=O)R^g$, $—S(=O)_2R^g$, $—OS(=O)_{1-2}R^g$, $—S(=O)_{1-2}OR^g$, $—NR^gS(=O)_{1-2}NR^gR^h$, $=NSO_2R^g$, $=NOR^g$, $—S(=O)_{1-2}NR^gR^h$, $—SF_5$, or $—SCF_3$. In certain embodiments, "substituted" also means a group in which one or more (e.g., 1 to 5 or 1 to 3) hydrogen atoms are replaced with $—C(=O)R^g$, $—C(=O)OR^g$, $—C(=O)NR^gR^h$, $—CH_2SO_2R^g$, or $—CH_2SO_2NR^gR^h$. In the foregoing, $R^g$ and $R^h$ are the same or different and independently hydrogen, alkyl, alkenyl, alkynyl, alkoxy, thioalkyl, aryl, arylalkyl, cycloalkyl, cycloalkylalkyl, haloalkyl, heterocyclyl, heterocyclylalkyl, heteroaryl, and/or heteroarylalkyl, or $R^g$ and $R^h$ are taken together with the atoms to which they are attached to form a heterocyclyl ring optionally substituted with oxo, halo, or alkyl, wherein the alkyl is optionally substituted with oxo, halo, amino, hydroxyl, or alkoxy.

Polymers or similar indefinite structures arrived at by defining substituents with further substituents appended ad infinitum (e.g., a substituted aryl having a substituted alkyl which is itself substituted with a substituted aryl group, which is further substituted by a substituted heteroalkyl group, etc.) are not intended to arise from the above definitions. Unless otherwise noted, the maximum number of serial substitutions in compounds described herein is three. For example, serial substitutions of substituted aryl groups with two other substituted aryl groups are limited to ((substituted aryl)substituted aryl) substituted aryl. Similarly, the above definitions are not intended to encompass compounds having chemically unfeasible or unisolable substitution patterns (e.g., methyl substituted with 5 fluorines or heteroaryl groups having three consecutive oxygen ring atoms). Such impermissible substitution patterns are well known to the skilled artisan. When used to modify a chemical group, the term "substituted" may describe other chemical groups defined herein.

In certain embodiments, as used herein, the phrase "one or more" refers to one to five. In certain embodiments, as used herein, the phrase "one or more" refers to one to three.

Any compound or structure given herein is intended to represent unlabeled forms as well as "isotopically enriched analogs" of the compounds. Isotopically enriched forms of compounds may also be referred to as "labeled." Isotopically enriched analogs have structures depicted herein, except that one or more atoms are enriched in an isotope having a selected atomic mass or mass number. Examples of isotopes that can be incorporated into the compounds described herein include isotopes of hydrogen, carbon, nitrogen, oxygen, phosphorous, fluorine, chlorine, and iodine, such as $^{2}H$, $^{3}H$, $^{11}C$, $^{13}C$, $^{14}C$, $^{13}N$, $^{15}N$, $^{15}O$, $^{17}O$, $^{18}O$, $^{31}P$, $^{32}P$, $^{35}S$, $^{18}F$, $^{36}Cl$, $^{123}I$, and $^{125}I$, respectively. Generally, an isotopically enriched analog includes compounds having any isotopic enrichment above the natural abundance of the isotope (e.g., at Earth's surface). Various isotopically labeled compounds are included in the present disclosure, for example those into which radioactive isotopes such as $^{3}H$, $^{18}F$, $^{11}C$, and $^{14}C$ are incorporated. Compounds labeled with $^{18}F$, $^{3}H$, or $^{11}C$ may be useful in metabolic studies, reaction kinetic studies, detection or imaging techniques, such as positron emission tomography (PET) or single-photon emission computed tomography (SPECT), including drug or substrate tissue distribution assays or in radiation treatment of patients.

Also provided are "deuterated analogs" of compounds described herein in which one or more hydrogens is/are replaced by deuterium, such as a hydrogen on a carbon atom. Such compounds are synthesized by, for example, carrying out a reaction such as one provided herein or known in the art, and employing starting materials or reactants in which one or more hydrogen atoms have been replaced by deuterium atoms.

Isotopically labeled compounds of this disclosure and prodrugs thereof can generally be prepared by carrying out the procedures disclosed in the schemes or in the examples and preparations described below by substituting an available isotopically labeled reagent for a non-isotopically labeled reagent. Where a compound is described as a deuterated analog, the compound may be drawn with deuterium as a substituent.

The concentration of such a heavier isotope may be defined by an isotopic enrichment factor. In the compounds of this disclosure any atom not specifically designated as a particular isotope is meant to represent any stable isotope of that atom. Unless otherwise stated, when a position is designated specifically as "H" or "hydrogen", the position is understood to have hydrogen and its isotopes at their natural abundances.

In many cases, the compounds of this disclosure are capable of forming acid and/or base salts by virtue of the presence of amino and/or carboxyl groups or groups similar thereto.

Provided also are isotopically enriched analogs, pharmaceutically acceptable salts, prodrugs, tautomers, stereoisomers, and mixtures of stereoisomers of the compounds described herein. "Pharmaceutically acceptable" or "physiologically acceptable" refer to compounds, salts, compositions, dosage forms and other materials which are useful in preparing a pharmaceutical composition that is suitable for veterinary or human pharmaceutical use.

The term "pharmaceutically acceptable salt" of a compound described herein refers to salts that retain the biological effectiveness and properties of the given compound and which are not biologically or otherwise undesirable. "Pharmaceutically acceptable salts" or "physiologically acceptable salts" of compounds described herein include, for example, acid addition salts obtained by interacting a compound with a basic functional group with an acid, and base addition salts obtained by interacting a compounds with an acidic functional group with a base. If the compound is obtained as an acid addition salt, the free base can be obtained by basifying a solution of the acid salt. Conversely, if the compound is a free base (e.g., of an amine), an addition salt may be produced by dissolving the free base in a suitable organic solvent and treating the solution with an acid. Those skilled in the art will recognize various synthetic methodologies that may be used to prepare nontoxic pharmaceutically acceptable addition salts. Pharmaceutically acceptable acid addition salts of compounds described herein may be prepared from inorganic and organic acids.

Suitable inorganic acids include, e.g., hydrochloric acid, hydrobromic acid, sulfuric acid, nitric acid, phosphoric acid, and the like. Suitable organic acids include, e.g., acetic acid, propionic acid, gluconic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like. Likewise, pharmaceutically acceptable base addition salts can be prepared from inorganic and organic bases. Salts derived from inorganic bases include, by way of example only, sodium, potassium, lithium, aluminum, ammonium, calcium and magnesium salts. Salts derived from organic bases include, but are not limited to, salts of primary, secondary and tertiary amines, such as alkyl amines (i.e., $NH_2$(alkyl)), dialkyl amines (i.e., HN(alkyl)$_2$), trialkyl amines (i.e., N(alkyl)$_3$), substituted alkyl amines (i.e., $NH_2$ (substituted alkyl)), di(substituted alkyl) amines (i.e., HN(substituted alkyl)$_2$), tri(substituted alkyl) amines (i.e., N(substituted alkyl)$_3$), alkenyl amines (i.e., $NH_2$(alkenyl)), dialkenyl amines (i.e., HN(alkenyl)$_2$), trialkenyl amines (i.e., N(alkenyl)$_3$), substituted alkenyl amines (i.e., $NH_2$ (substituted alkenyl)), di(substituted alkenyl) amines (i.e., HN(substituted alkenyl)$_2$), tri(substituted alkenyl) amines (i.e., N(substituted alkenyl)$_3$, mono-, di-, or tri-cycloalkyl amines (i.e., $NH_2$(cycloalkyl), HN(cycloalkyl)$_2$, N(cycloalkyl)$_3$), mono-, di-, or tri-arylamines (i.e., $NH_2$(aryl), HN(aryl)$_2$, N(aryl)$_3$), cyclic amines (e.g., piperidine, piperazine, 1,4-diazabicyclo[2.2.2]octane), aromatic amines (e.g., pyridine, quinoline), or mixed amines, etc. Specific examples of suitable amines include, by way of example only, isopropylamine, trimethyl amine, diethyl amine, tri (iso-propyl) amine, tri(n-propyl) amine, ethanolamine, 2-dimethylaminoethanol, piperazine, piperidine, morpholine, N-ethylpiperidine, and the like.

Some compounds described herein may exist as tautomers. For example, where a compound is drawn as including an amide, the compound may exist as an imidic acid tautomer, and where a compound is drawn as including a ketone, the compound may also exist as an enol tautomer. Regardless of which tautomer is shown and regardless of the nature of the equilibrium among tautomers, the compounds are understood by one of ordinary skill in the art to comprise both tautomers. Thus, for example, the amide containing compounds are understood to include their imidic acid tautomers, and the imidic acid containing compounds are understood to include their amide tautomers.

The compounds described herein may include an asymmetric center and may thus give rise to enantiomers, diastereomers, and other stereoisomeric forms that may be defined, in terms of absolute stereochemistry, as (R)- or (S)-, or as (D)- or (L)- for amino acids. Compounds described herein are meant to include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, for example, (chiral) chromatography and/or fractional crystallization. Conventional techniques for the preparation/isolation of individual enantiomers include chiral synthesis from a suitable optically pure precursor or resolution of the racemate (or the racemate of a salt or derivative) using, for example, chiral high performance liquid chromatography (HPLC). When the compounds described herein contain double bonds or other centers of geometric asymmetry, and unless specified otherwise, it is intended that the compounds include both cis- and trans- or E- and Z-geometric isomers.

A "stercoisomer" refers to one of a set of compounds made up of the same atoms bonded by the same bonds but having different three-dimensional structures. Various stereoisomers and mixtures thereof are contemplated including "enantiomers," which refers to stereoisomeric compounds that are non-superimposable mirror images of one another.

A "diastereomer" is one of a set of stereoisomers that have at least two asymmetric atoms that are not mirror-images of each other.

A "prodrug" is any molecule which releases a putatively active parent drug according to a compound described herein in vivo when such prodrug is administered to a mammalian subject. A prodrug may be a form of a compound described herein modified in such a way that the modifications may be cleaved in vivo to release the parent compound. Prodrugs may be prepared by modifying functional groups present in the compound described herein in such a way that the modifications are cleaved, either in routine manipulation or in vivo, to the parent compounds. Prodrugs include compounds described herein wherein a hydroxy, amino, carboxyl, or sulfhydryl group in a compound described herein is bonded to any group that may be cleaved in vivo to regenerate the free hydroxy, amino, or sulfhydryl group, respectively. Examples of prodrugs include, but are not limited to esters (e.g., acetate, formate, and benzoate derivatives), amides, guanidines, carbamates (e.g., N,N-dimethylaminocarbonyl) of hydroxy functional groups in compounds described herein, and the like. Preparation, selection, and use of prodrugs is discussed in T. Higuchi and V. Stella, "Pro-drugs as Novel Delivery Systems," Vol. 14 of the A.C.S. Symposium Series; "Design of Prodrugs," ed. H. Bundgaard, Elsevier, 1985; and in Bioreversible Carriers in Drug Design, ed. Edward B. Roche, American Pharmaceutical Association and Pergamon Press, 1987, each of which are hereby incorporated by reference in their entirety.

The methods described herein may be applied to cell populations in vivo or ex vivo. "In vivo" means within a living individual, as within an animal or human. In this context, the methods described herein may be used therapeutically in an individual. "Ex vivo" means outside of a living individual. Examples of ex vivo cell populations include in vitro cell cultures and biological samples including fluid or tissue samples obtained from individuals. Such samples may be obtained by methods well known in the art. Exemplary biological fluid samples include blood, cerebrospinal fluid, urine, and saliva. In this context, the compounds and compositions described herein may be used for a variety of purposes, including therapeutic and experimental purposes. For example, the compounds and compositions described herein may be used ex vivo to determine the optimal schedule and/or dosing of administration of a compound of the present disclosure for a given indication, cell type, individual, and other parameters. Information gleaned from such use may be used for experimental purposes or in the clinic to set protocols for in vivo treatment. Other ex vivo uses for which the compounds and compositions described herein may be suited are described below or will become apparent to those skilled in the art. The selected compounds may be further characterized to examine the safety or tolerance dosage in human or non-human subjects. Such properties may be examined using commonly known methods to those skilled in the art.

The above-listed terms also include in vitro and ex vivo methods.

As used herein the terms "group," "moiety," "radical," "substituent," and "fragment" are synonymous and are intended to indicate portions of molecules attachable to other portions of molecules, e.g., through an indicated attachment point or bond.

The term "active agent" is used to indicate a compound which has biological activity in the treatment, amelioration, or prevention of a disease or condition. In some embodiments, an "active agent" is a compound or an isotopically labeled analog, pharmaceutically acceptable salt, solvate, prodrug, stereoisomer, or mixture of stercoisomers thereof, having pharmaceutical utility. For example an active agent may be an anti-neurodegenerative therapeutic.

The term "effective amount" means an amount, for example, of a compound described herein, sufficient to bring about a desired response in an individual or patient. In the context of use of an imaging agent, an effective amount may be an amount needed to produce an image having diagnostic or therapeutic utility. The term "therapeutically effective amount" means an amount effective, when administered to a human or non-human patient, to provide a therapeutic benefit such as amelioration of symptoms, slowing of disease progression, or prevention of disease e.g., a therapeutically effective amount may be an amount sufficient to decrease the symptoms of a disease described herein. The (therapeutically) effective amount may vary depending on the subject, and disease or condition being treated, the weight and age of the subject, the severity of the disease or condition, and the manner of administering, which can readily be determined by one of ordinary skill in the art.

The term "huntingtin protein" or "HTT protein" as used herein, refers to the protein encoded by the human huntingtin gene (HTT gene) located on the short (p) arm of chromosome 4 at position 16.3. More precisely, the $IT_{15}$ gene coding for the HTT protein is located from base pair 3,076,407 to base pair 3,245,686 on chromosome 4.

The term "protein aggregate," as used herein refers to an aggregation of protein which may be, for example, an insoluble fibrous amyloid comprising mis-folded HTT protein molecules ("HTT protein aggregate") or mis-folded β-amyloid protein molecules ("β-amyloid aggregate"). A "protein susceptible to aggregation" is a protein that is capable of forming such aggregates, in its wild type or in a mutated form.

The term "imaging agent," as used herein, refers to a compound described herein labeled with one or more positron-emitting isotopes or radionuclides, or a composition comprising the labeled compound. A positron-emitter labeled compound need only be enriched with a detectable isotope to a degree that permits detection with a technique suitable for the particular application.

The term "PET imaging" (which may be referred to as positron emission tomography imaging), as used herein, refers to the use of a positron-emitter labeled compound to produce images of internal structures of the human or animal body.

The term "positron-emitting radionuclide," or "positron-emitting isotope" as used herein, refers to an isotope that exhibits particular type of radioactive decay referred to as β+ decay, in which a proton inside a radionuclide nucleus is converted into a neutron while releasing a positron and an electron neutrino ($v_e$). Some examples of positron-emitting isotopes include $^{15}O$, $^{13}N$, $^{11}C$, $^{18}F$, $^{76}Br$, and $^{124}I$.

The term "labeled," as used herein, refers to a compound which is associated with one or more positron-emitting isotopes in greater than natural abundance. For example, a labeled compound described herein may contain one or more positron-emitting radionuclides, wherein an atom in the molecule (including an atom in an indicated substituent) is present as a positron-emitting isotope.

The term "tomography," as used herein, refers to a process of imaging by sections. The images may be looked at individually, as a series of two-dimensional slices or together, as a computer-generated three-dimensional representation.

In some embodiments, the term "neurodegenerative disease" refers to a disease or condition in which the function of a subject's nervous system becomes impaired. Examples of neurodegenerative diseases include those described herein.

"Treatment" or "treating" means any treatment of a disease state in a patient, including a) inhibiting the disease (e.g., decreasing one or more symptoms resulting from the disease or condition, and/or diminishing the extent of the disease or condition);
b) slowing or arresting the development of clinical symptoms associated with the disease or condition (e.g., stabilizing the disease or condition, preventing or delaying the worsening or progression of the disease or condition, and/or preventing or delaying the spread (e.g., metastasis) of the disease or condition); and/or
c) relieving the disease, that is, causing the regression of clinical symptoms (e.g., ameliorating the disease state, providing partial or total remission of the disease or condition, enhancing effect of another medication, delaying the progression of the disease, increasing the quality of life and/or prolonging survival).

"Prevention" or "preventing" means any treatment of a disease or condition that causes the clinical symptoms of the disease or condition not to develop. Compounds may, in some embodiments, be administered to a subject (including a human) who is at risk (e.g., carries a genetic or epigenetic marker, has engaged in an activity, or has been exposed to an environmental condition, associated with the disease or condition) or has a family history of the disease or condition.

"Subject" or "patient" refers to an animal, such as a mammal, that has been or will be the object of treatment, observation, or experiment. The methods described herein may be useful in both human therapy and veterinary applications. In some embodiments, the subject or patient is a mammal. In some embodiments, the subject or patient is human.

The term "Curie" (Ci) is a unit of measurement of radioactivity and has its customary meaning to those of skill in the art.

The term "diagnostic imaging," as used herein, refers to the use of electromagnetic radiation to produce images of internal structures of the human or animal body for the purpose of diagnosis.

The term "metabolically protected fluorine atom" means a compound containing a fluorine atom which has adjacent functionality that reduces cleavage to form a difluorinated isomer. The metabolically protected fluorine atom may comprise one or more deuterium atoms adjacent (e.g., geminal or vicinal) to the fluorine atom. Through-space (e.g., steric) blocking is also contemplated. The compound comprising the metabolically protected fluorine atom may comprise a primary fluoroalkyl or primary fluoroalkoxy group that includes protecting functionality adjacent to the primary fluoride. Such compounds may be prepared by methods described herein and known in the art.

It is appreciated that certain features described herein, which are, for clarity, described in the context of separate embodiments, may also be provided in combination in a single embodiment. Conversely, various features described herein, which are, for brevity, described in the context of a single embodiment, may also be provided separately or in any suitable subcombination. All combinations of the embodiments pertaining to the chemical groups represented by the variables contained within Formula I, Formula Ia, or Formula Ib, or any other formula are specifically embraced herein just as if each and every combination was individually and explicitly recited, to the extent that such combinations result in stable compounds (i.e., compounds that can be isolated, characterized, and tested for biological activity). In addition, all subcombinations of the chemical groups listed in the embodiments describing such variables, as well as all subcombinations of uses and medical indications described herein, are also specifically embraced herein just as if each and every subcombination of chemical groups and subcombination of uses and medical indications was individually and explicitly recited herein. In addition, some embodiments include every combination of one or more additional agents disclosed herein just as if each and every combination was individually and explicitly recited.

| List of Abbreviations and Acronyms | |
|---|---|
| δ | Chemical shift |
| Ac | Acetate |
| approx. | Approximately |
| BP | Binding potential |
| br | Broad |
| CMBP | Cyanomethyltributylphosphorane |
| *d* | Deuterated |
| d | Doublet |
| dd | Doublet of doublets |
| DCM | Dichloromethane |
| DMF | N,N-dimethylformamide |
| DMSO | Dimethyl sulfoxide |
| EDC | 1-Ethyl-3-(3-dimethylaminopropyl)carbodiimide |
| ELS | Evaporative light scattering |
| ESI | Electrospray ionization |
| Et | Ethyl |
| EtOAc | Ethyl acetate |
| EtOH | Ethanol |
| FCC | Flash column chromatography |
| h | Hour(s) |
| HATU | 1-[Bis(dimethylamino)methylene]-1H-1,2,3-triazolo[4,5-b]pyridinium 3-oxide hexafluorophosphate |
| HOBt | 1-Hydroxybenzotriazole |
| HPLC | High performance liquid chromatography |
| $IC_{50}$ | Half maximal inhibitory concentration |
| J | Coupling constant |
| $K_{assn}$ | Association Constant |
| $K_{diss}$ | Dissociation Constant |
| LCMS | Liquid chromatography-mass spectrometry |
| m | Multiplet |
| M | Molar |
| MBq | Megabecquerels |
| Me | Methyl |
| MeCN | Acetonitrile |
| MeOH | Methanol |
| MHz | Megahertz |
| min | Minute(s) |
| MPLC | Medium Pressure Liquid Chromatography |
| MTBE | Methyl tert-butyl ether |
| m/z | Mass to charge ratio |

-continued

| List of Abbreviations and Acronyms | |
|---|---|
| NMR | Nuclear magnetic resonance |
| *p* | Para |
| PBS | Phosphate buffered saline |
| PDA | Photodiode array |
| $PdCl_2$(dppf) | [1,1'-Bis(diphenylphosphino)ferrocene]dichloropalladium(II) |
| Ph | Phenyl |
| ppm | Part(s) per million |
| prep | Preparative |
| q | Quartet |
| RBA | Radioligand binding assay |
| ROI | Regions of interest |
| rt | Room temperature |
| s | Singlet |
| SCX | Propylsulfonic acid (non-endcapped) functionalized silica |
| t | Triplet |
| TAC | Time activity curve |
| TBAF | Tetrabutylammonium fluoride |
| THF | Tetrahydrofuran |
| TLC | Thin-layer chromatography |
| Tr | Retention time |
| Tris | Tris(hydroxymethyl)aminomethane |
| UPLC | Ultra-performance liquid chromatography |
| UV | Ultraviolet |
| v/v | Volume per volume |
| WT | Wild type |

Compounds

The present disclosure relates to compounds useful for imaging a protein susceptible to aggregation, for example, Huntingtin protein. The compound may comprise a metabolically protected fluoride atom.

Some embodiments provide a compound of Formula Ia:

Ia

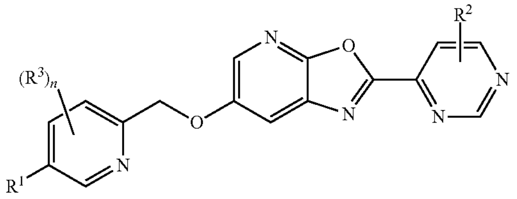

or an isotopically enriched analog, pharmaceutically acceptable salt, prodrug, tautomer, stereoisomer, or a mixture of stereoisomers thereof, wherein:

$R^1$ is $C_{1-6}$alkyl, $C_{2-6}$alkenyl, $C_{1-6}$haloalkyl, deuterated $C_{1-6}$haloalkyl, $C_{1-6}$alkoxy, $C_{1-6}$haloalkoxy, deuterated $C_{1-6}$haloalkoxy, —O-alkylene-O—$SO_2$—$R^5$, or —O-deuterated alkylene-O—$SO_2$—$R^5$;

$R^5$ is aryl optionally substituted by alkyl;

$R^2$ is absent, $C_{1-6}$alkyl, $C_{1-6}$haloalkyl, deuterated $C_{1-6}$haloalkyl, $C_{1-6}$haloalkoxy, or deuterated $C_{1-6}$haloalkoxy;

$R^3$ is halo, $C_{1-6}$alkyl, or $C_{1-6}$haloalkyl; and n is 0, 1, or 2.

Some embodiments provide a compound of Formula Ib:

Ib

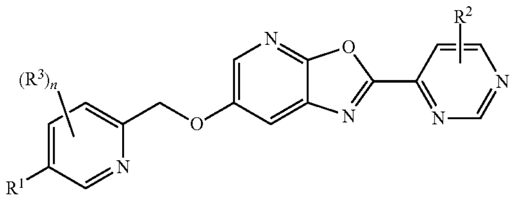

or an isotopically enriched analog, pharmaceutically acceptable salt, prodrug, tautomer, stereoisomer, or a mixture of stereoisomers thereof, wherein:

$R^1$ is $C_{1-6}$alkyl, $C_{2-6}$alkenyl, $C_{1-6}$haloalkyl, deuterated $C_{1-6}$haloalkyl, $C_{1-6}$alkoxy, deuterated $C_{1-6}$haloalkoxy, —O-alkylene-O—$SO_2$—$R^5$, or —O-deuterated alkylene-O—$SO_2$—$R^5$;

$R^5$ is aryl optionally substituted by alkyl;

$R^2$ is absent, $C_{1-6}$alkyl, $C_{1-6}$haloalkyl, deuterated $C_{1-6}$haloalkyl, $C_{1-6}$haloalkoxy, or deuterated $C_{1-6}$haloalkoxy;

$R^3$ is halo, $C_{1-6}$alkyl, or $C_{1-6}$haloalkyl; and n is 0, 1, or 2.

Some embodiments provide for a compound of Formula I:

I

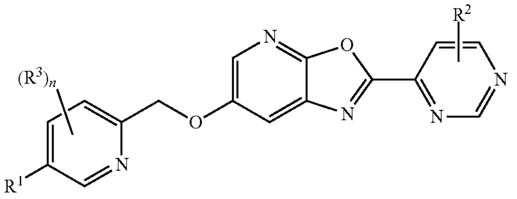

or an isotopically enriched analog, pharmaceutically acceptable salt, prodrug, tautomer, stereoisomer, or a mixture of stereoisomers thereof, wherein:

$R^1$ is $C_{1-6}$alkyl, $C_{2-6}$alkenyl, $C_{1-6}$haloalkyl, deuterated $C_{1-6}$haloalkyl, $C_{1-6}$alkoxy, deuterated $C_{1-6}$haloalkoxy, or —O-alkylene-O—$SO_2$—$R^5$;

$R^5$ is aryl optionally substituted by alkyl;

$R^2$ is absent, $C_{1-6}$alkyl, $C_{1-6}$haloalkyl, deuterated $C_{1-6}$haloalkyl, $C_{1-6}$haloalkoxy, or deuterated $C_{1-6}$haloalkoxy;

$R^3$ is halo, $C_{1-6}$alkyl, or $C_{1-6}$haloalkyl; and n is 0, 1, or 2.

In some embodiments, the compound of Formula I, Formula Ia, or Formula Ib, is a compound of Formula II:

II

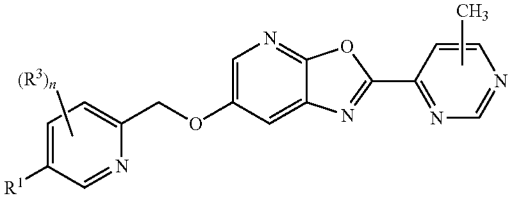

or an isotopically enriched analog, pharmaceutically acceptable salt, prodrug, tautomer, stereoisomer, or a mixture of stereoisomers thereof.

In some embodiments, the compound of Formula I, Formula Ia, or Formula Ib, is a compound of Formula III:

III

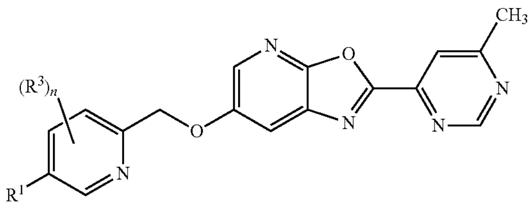

or an isotopically enriched analog, pharmaceutically acceptable salt, prodrug, tautomer, stereoisomer, or a mixture of stereoisomers thereof.

In some embodiments, the compound of Formula I, Formula Ia, or Formula Ib, is a compound of Formula IV:

IV

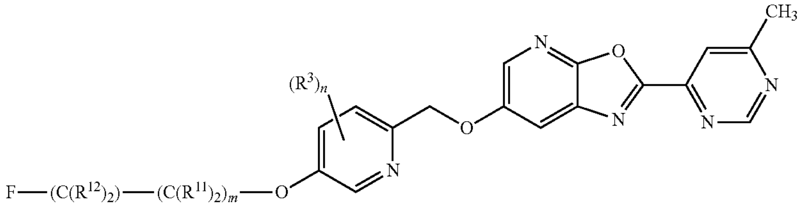

or an isotopically enriched analog, pharmaceutically acceptable salt, prodrug, tautomer, stereoisomer, or a mixture of stereoisomers thereof, wherein m is 0, 1, or 2, each $R^{11}$ and each $R^{12}$ is independently selected from hydrogen and deuterium, and at least one $R^{11}$ or $R^{12}$ is deuterium.

In some embodiments, the compound of Formula I, Formula Ia, or Formula Ib, is a compound of Formula V:

V

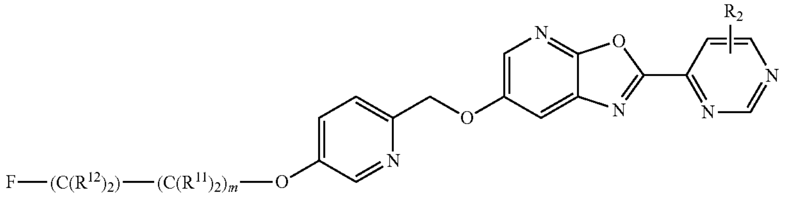

or an isotopically enriched analog, pharmaceutically acceptable salt, prodrug, tautomer, stereoisomer, or a mixture of stereoisomers thereof, wherein m is 0, 1, or 2, each $R^{11}$ and each $R^{12}$ is independently selected from hydrogen and deuterium, and at least one $R^{11}$ or $R^{12}$ is deuterium.

In some embodiments, the compound of Formula I, Formula Ia, or Formula Ib, is a compound of Formula VI:

VI

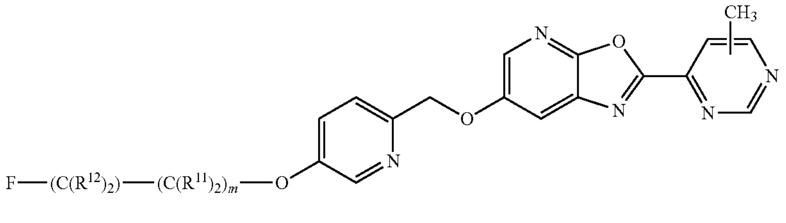

or an isotopically enriched analog, pharmaceutically acceptable salt, prodrug, tautomer, stereoisomer, or a mixture of stereoisomers thereof; wherein m is 0, 1, or 2, each $R^{11}$ and each $R^{12}$ is independently selected from hydrogen and deuterium, and at least one $R^{11}$ or $R^{12}$ is deuterium.

In some embodiments, the compound of Formula I, Formula Ia, or Formula Ib, is a compound of Formula VII:

VII

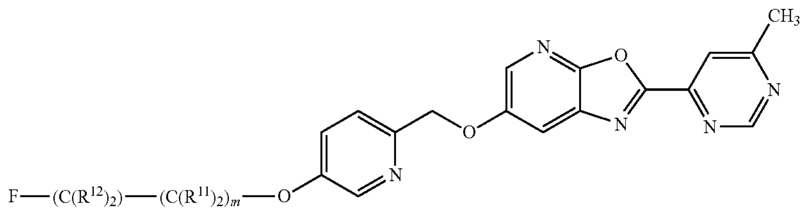

or an isotopically enriched analog, pharmaceutically acceptable salt, prodrug, tautomer, stereoisomer, or a mixture of stereoisomers thereof, wherein m is 0, 1, or 2, each $R^{11}$ and each $R^{12}$ is independently selected from hydrogen and deuterium, and at least one $R^{11}$ or $R^{12}$ is deuterium.

In some embodiments, the compound comprises a metabolically protected fluorine atom. The compound having a metabolically protected fluorine atom may comprise a primary fluoro with one to four geminal and/or vicinal deuterium atoms. The compound comprising a metabolically protected fluorine atom may comprise a deuterated $C_{1-6}$haloalkyl or deuterated $C_{1-6}$haloalkoxy. The metabolically protected fluorine atom may be a deuterated fluorine-containing group selected from fluoroalkyl, fluoroalkenyl, and fluoroalkynyl group. The compound may comprise a substituent group having the structure

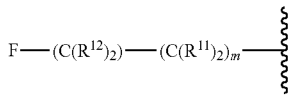

wherein m is 0, 1, or 2, each $R^{11}$ and each $R^{12}$ is independently selected from hydrogen, deuterium, and $C_{1-3}$alkyl, and at least one $R^{11}$ or $R^{12}$ is deuterium, and the wavy line indicates a point of attachment to a parent structure, for example a structure having any Formula provided herein. In some embodiments, each $R^{11}$ and each $R^{12}$ is deuterium.

In some embodiments, the compound having a metabolically protected fluorine comprises a substituent group having the structure

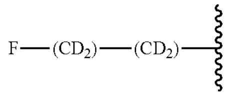

wherein the wavy line indicates a point of attachment to a parent structure. The bond at the wavy line may be appended via a linking functionality, e.g., via an oxygen atom to form an ether.

In some embodiments, the compound comprises at least one fluoro. In some embodiments, the compound comprises one fluoro. In some embodiments, $R^1$ includes a fluorine atom.

In some embodiments, one of $R^1$ or $R^2$ comprises a deuterated $C_{1-6}$haloalkyl, deuterated $C_{1-6}$haloalkoxy, or a moiety

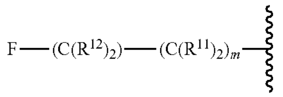

wherein m is 0, 1, or 2, each $R^{11}$ and each $R^2$ is independently selected from hydrogen, deuterium, and $C_{1-3}$alkyl, and at least one $R^{11}$ or $R^{12}$ is deuterium, and wherein the wavy line indicates a point of attachment to a parent structure.

In some embodiments, one of $R^1$ or $R^2$ is $F—(C(R^{12})_2)—(C(R^{11})_2)_m—O—$ wherein m is 0, 1, or 2, each $R^{11}$ and each $R^{12}$ is independently selected from hydrogen, deuterium, and $C_{1-3}$alkyl, and at least one $R^{11}$ or $R^{12}$ is deuterium.

In some embodiments, each $R^{11}$ and each $R^{12}$ is deuterium.

In some embodiments, $R^1$ is deuterated $C_{1-6}$haloalkyl or deuterated $C_{1-6}$haloalkoxy.

In some embodiments, $R^1$ is deuterated $C_{1-6}$haloalkoxy. In some embodiments, $R^1$ is $C_{1-6}$fluoroalkoxy.

In some embodiments, $R^1$ is $—O-CD_2-CD_2-F$.

In some embodiments, each $R^{11}$ and each $R^{12}$ is independently selected from halo, hydrogen, and deuterium, and at least one $R^{11}$ or $R^{12}$ is deuterium or halo. In some embodiments, at least one $R^{11}$ and at least one $R^{12}$ is halo. In some embodiments, each $R^{11}$ and each $R^{12}$ is fluoro.

In some embodiments, $R^2$ is $C_{1-6}$alkyl or $C_{1-6}$haloalkoxy.

In some embodiments, $R^2$ is $C_{1-6}$alkyl.

In some embodiments, n is 0.

In some embodiments, $R^3$ is fluoro.

In some embodiments, the compound of Formula I, Formula Ia, or Formula Ib, is labeled with one or more positron-emitting isotopes.

In some embodiments, the compound contains one or more positron-emitting isotopes selected from $^{11}C$, $^{13}N$, $^{15}O$, and $^{18}F$.

In some embodiments, an imaging agent comprising the compound of Formula I, Formula Ia, or Formula Ib, or an isotopically enriched analog, pharmaceutically acceptable salt, prodrug, tautomer, stereoisomer, or a mixture of stereoisomers thereof, is provided.

Also provided are additional compounds as described herein. In some embodiments, provided is a compound selected from Table 1, or an isotopically labeled analog, pharmaceutically acceptable salt, solvate, prodrug, stereoisomer, or mixture of stereoisomers thereof.

In some embodiments, provided is a compound selected from those in Table 1, or an isotopically enriched analog, pharmaceutically acceptable salt, prodrug, tautomer, stereoisomer, or a mixture of stereoisomers thereof, optionally wherein the compound is labeled with one or more positron-emitting isotopes.

In some embodiments, provided is a pharmaceutical composition comprising the compound described herein, or an isotopically enriched analog, pharmaceutically acceptable salt, prodrug, tautomer, stereoisomer, or a mixture of stereoisomers thereof, and a pharmaceutically acceptable excipient.

Non-metal positron-emitting isotopes may be covalently linked to the compounds described herein by a reaction well known from the state of art. When the positron-emitting isotope is a metallic positron-emitter, it is understood that labeling may require the use of a chelating agent. Such chelating agents are well known from the state of the art.

In some embodiments, provided is a compound selected from those described in the Examples section provided herein.

Also is provided a compound, or an isotopically enriched analog, pharmaceutically acceptable salt, prodrug, tautomer, stereoisomer, or a mixture of stereoisomers thereof, selected from Table 1:

TABLE 1

| Ex. | Structure |
|---|---|
| 1-1 | 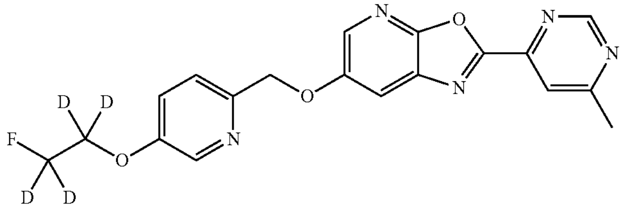 [SMILES: [2H]C([2H])(F)C([2H])([2H])Oc1ccc(COc2cnc3oc(-c4cc(C)ncn4)nc3c2)nc1] |
| 1-2 | 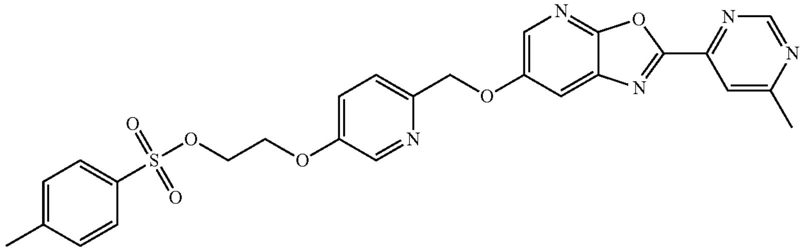 |
| 1-3 | 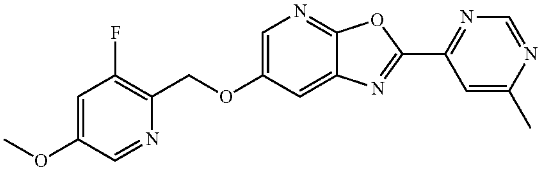 |
| 1-4 | 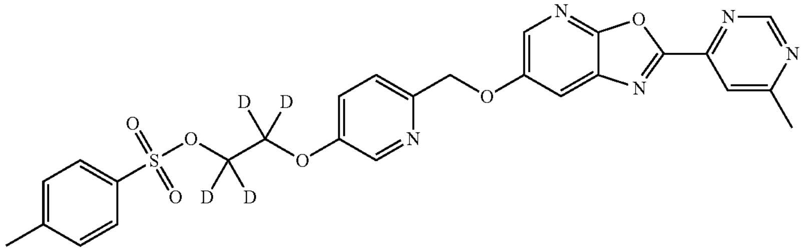 |
| 2-1 | 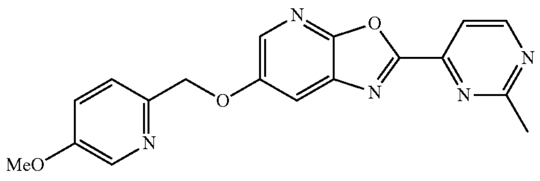 [SMILES: COc1ccc(COc2cnc3oc(-c4ccnc(C)n4)nc3c2)nc1] |

TABLE 1-continued

| Ex. | Structure |
| --- | --- |
| 3-1 | 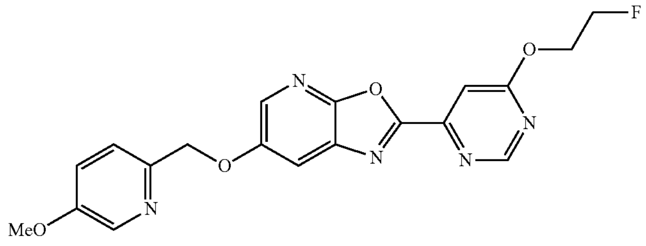 [SMILES: COc1ccc(COc2cnc3oc(-c4cc(OCCF)ncn4)nc3c2)nc1] |
| 4-1 | 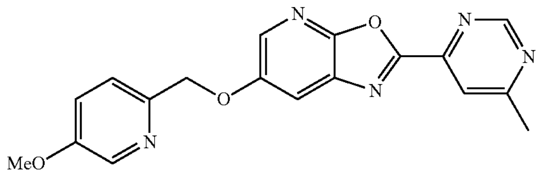 [SMILES: COc1ccc(COc2cnc3oc(-c4cc(C)ncn4)nc3c2)nc1] |
| 5-1 | 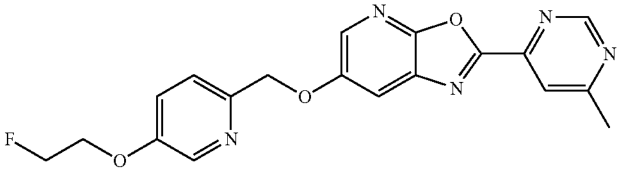 [SMILES: Cc1cc(-c2nc3cc(OCc4ccc(OCCF)cn4)cnc3o2)ncn1] |
| 5-2 | 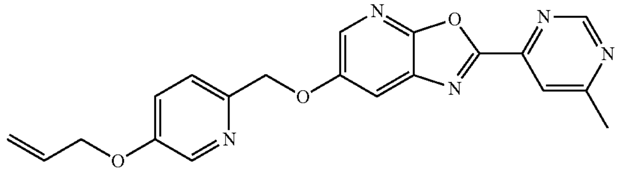 [SMILES: C=CCOc1ccc(COc2cnc3oc(-c4cc(C)ncn4)nc3c2)nc1] |
| 5-3 | 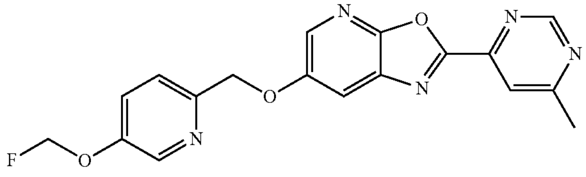 [SMILES: Cc1cc(-c2nc3cc(OCc4ccc(OCF)cn4)cnc3o2)ncn1] |

In some embodiments, the compound is a compound of Formula X:

X

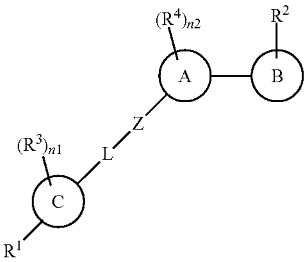

or an isotopically enriched analog, pharmaceutically acceptable salt, prodrug, tautomer, stereoisomer, or a mixture of stereoisomers thereof, wherein:

Ring A is a 9-membered bicyclic heteroaryl;

Ring B is a 6-membered heterocyclyl, 6-membered oxo-heterocyclyl, or 6-membered heteroaryl;

Ring C is a 6-membered heteroaryl;

Z is O, S, NH, or $N(C_{1-3}alkyl)$;

L is $CH_2$, $CH(C_{1-3}alkyl)$, $C(C_{1-3}alkyl)_2$, or C(O);

$R^1$ is cyano, halo, hydroxy, nitro, $C_{1-6}$alkyl, $C_{2-6}$alkenyl, $C_{2-6}$alkynyl, $C_{1-6}$haloalkyl, deuterated $C_{1-6}$haloalkyl, $C_{1-6}$alkoxy, $C_{1-6}$haloalkoxy, deuterated $C_{1-6}$haloalkoxy, $C_{1-6}$alkylthio, $C_{3-8}$ cycloalkyl, heterocyclyl, heteroaryl, amino, alkylamino, dialkylamino, or —O-alkylene-O—$SO_2$—$R^5$;

$R^5$ is aryl optionally substituted by alkyl;

$R^2$ is absent, cyano, halo, hydroxy, nitro, $C_{1-6}$alkyl, $C_{1-6}$haloalkyl, deuterated $C_{1-6}$haloalkyl, $C_{1-6}$alkoxy, $C_{1-6}$haloalkoxy, deuterated $C_{1-6}$haloalkoxy, $C_{1-6}$alkylthio, $C_{3-8}$ cycloalkyl, heterocyclyl, heteroaryl, amino, alkylamino, or dialkylamino;

$R^3$ is cyano, halo, hydroxy, nitro, $C_{1-6}$alkyl, $C_{1-6}$haloalkyl, deuterated $C_{1-6}$haloalkyl, $C_{1-6}$alkoxy, $C_{1-6}$haloalkoxy, deuterated $C_{1-6}$haloalkoxy, $C_{1-6}$alkylthio, $C_{3-8}$ cycloalkyl, heterocyclyl, heteroaryl, amino, alkylamino, or dialkylamino;

$R^4$ is cyano, halo, hydroxy, nitro, $C_{1-6}$alkyl, $C_{1-6}$haloalkyl, deuterated $C_{1-6}$haloalkyl, $C_{1-6}$alkoxy, $C_{1-6}$haloalkoxy, deuterated $C_{1-6}$haloalkoxy, $C_{1-6}$alkylthio, $C_{3-8}$ cycloalkyl, heterocyclyl, heteroaryl, amino, alkylamino, or dialkylamino;

n1 is 0, 1, or 2; and n2 is 0, 1, or 2;

wherein one of $R^1$, $R^2$, $R^3$, or $R^4$ comprises a deuterated $C_{1-6}$haloalkyl, deuterated $C_{1-6}$haloalkoxy, or a moiety

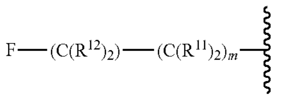

wherein m is 0, 1, or 2, each $R^{11}$ and each $R^{12}$ is independently selected from hydrogen, deuterium, and $C_{1-3}$alkyl, and at least one $R^{11}$ or $R^{12}$ is deuterium, and wherein the wavy line indicates a point of attachment to a parent structure.

In some embodiments, the compound is a compound of Formula XI:

XI

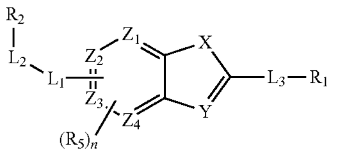

or an isotopically enriched analog, pharmaceutically acceptable salt, prodrug, tautomer, stereoisomer, or a mixture of stereoisomers thereof, wherein:

X is chosen from $NR^4$, O, and S;

Y is chosen from $CR_4$ and N;

$Z_1$, $Z_2$, $Z_3$, and $Z_4$ are independently chosen from CH and N, provided that at least two of $Z_1$, $Z_2$, $Z_3$, and $Z_4$ are CH;

$R_1$ is chosen from heteroaryl, heterocycloalkenyl, and heterocycloalkyl, each of which is optionally substituted with one or two groups independently chosen from cyano, halo, lower alkyl optionally substituted with amino, alkylamino, or di(alkyl)amino, lower alkoxy optionally substituted with lower alkoxy, optionally substituted amino, haloalkyl, di(alkyl)aminocarbonyl, alkylaminocarbonyl, and aminocarbonyl, or $R^1$ is phenyl optionally substituted with one or two groups independently chosen from cyano, heteroaryl, halo, phenoxy, benzyloxy, heteroaryl, lower alkyl optionally substituted with amino, (alkyl)amino, or di(alkyl) amino, lower alkoxy, optionally substituted amino, di(alkyl)aminocarbonyl, alkylaminocarbonyl, and aminocarbonyl;

$L_1$ is —O— and $L_2$ is —$(CR_7R_8)_m$— or —$(CR_7R_8)_m$—O—; or $L_1$ is —$NR_3$— and $L_2$ is —C(O)— or —$(CR_7R_8)_m$—; or $L_1$ is —$NR_3$— and $L_2$ is —C(O)(O)$(CR_7R_8)_m$—; or $L_1$ is —$NR_3$— and $L_2$ is —C(O)$(CR_7R_8)_m$(O)—; or $L_1$ is —$NR_3$— and $L_2$ is —C(O)$(CR_7R_8)_m$—; or $L_1$ is —$NR_3$— and $L_2$ is —C(O)$CR_7$═$CR_8$—; or $L_1$ is —C(O)— and $L_2$ is —$NR_3$; or $L_1$ is —$(CR_7R_8)_m$ and $L_2$ is —$NR_3$—, —C(O)—, or —O—; or $L_1$ is absent and $L_2$ is absent; or $L_1$ taken together with $L_2$ is —CH═CH—, —C≡C—, or heterocyclylene;

$L_3$ is —CH═CH—, or $L_3$ is absent;

$R_2$ is chosen from heterocycloalkyl, aryl, and heteroaryl, each of which is optionally substituted with one or two groups chosen from

—OC(O)—$R_6$,

—C(O)O—$R_6$, amino, halo, haloalkyl, phenyl, heteroaryl, cyano, (lower alkyl)thio, phenoxy, phenoxymethyl, heteroaryloxy, heteroaryloxy substituted with lower alkyl, hydroxyl, lower alkenyloxy, lower alkoxy, lower alkoxy substituted with lower alkoxy, amino, (alkyl)amino, (dialkyl)amino, heterocycloalkyl, heteroaryl, or halo, lower alkyl, and lower alkyl substituted with amino, (alkyl)amino, (dialkyl)amino, hydroxyl or lower alkoxy;

$R_3$ is chosen from hydrogen and lower alkyl;

$R_4$ is chosen from hydrogen, halo, cyano, and lower alkyl;

$R_5$ is chosen from lower alkyl, lower alkoxy, and halo;

$R_6$ is lower alkyl;

$R_7$ is chosen from hydrogen, hydroxyl, trifluoromethyl, and lower alkyl;

$R_8$ is chosen from hydrogen and lower alkyl;

n is 0 or 1; and m is 0, 1, or 2;

wherein the compound of Formula XI, or a pharmaceutically acceptable salt thereof, is labeled with one or more positron-emitting isotopes;

and wherein the compound comprises a metabolically protected fluorine atom.

In some embodiments, the compound is a compound of Formula XII:

XII

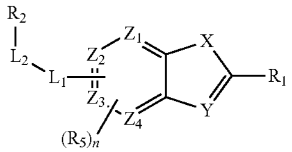

or an isotopically enriched analog, pharmaceutically acceptable salt, prodrug, tautomer, stereoisomer, or a mixture of stereoisomers thereof, wherein:

X is chosen from ($CR_3$═$CR_3$), O, NH, and S;

Y is chosen from $CR_3$ and N;

where for each occurrence, $R_3$ is independently chosen from hydrogen, halo, cyano, and lower alkyl;

$Z_1$, $Z_2$, $Z_3$, and $Z_4$ are independently chosen from CH and N, provided that at least two of $Z_1$, $Z_2$, $Z_3$, and $Z_4$ are CH;

$R_1$ is chosen from aryl, heteroaryl, and heterocycloalkyl, each of which is optionally substituted with one or two groups independently chosen from alkynyl, cyano, optionally substituted amino, halo, and lower alkyl optionally substituted with optionally substituted amino;

$L_1$ is chosen from C(O)O, O, and $NR_4$, or $L_1$ is absent;

$R_4$ is chosen from hydrogen and lower alkyl;

$L_2$ is $(CH_2)_m$ where m is 0, 1, or 2;

$R_2$ is chosen from hydrogen, hydroxyl, lower alkyl, lower haloalkyl, halo, and lower alkoxy, $R_5$ is chosen from lower alkyl, lower alkoxy, and halo; and n is 0 or 1; or $R^2$ and $R_5$, taken together with any intervening atoms forms a 5- to 7-membered heterocycloalkyl ring, wherein the compound of Formula XII, or a pharmaceutically acceptable salt thereof, is labeled with one or more positron-emitting isotopes;

and wherein the compound comprises a metabolically protected fluorine atom.

In some embodiments, the compound is a compound of Formula XIII:

XIII

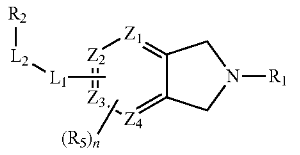

or an isotopically enriched analog, pharmaceutically acceptable salt, prodrug, tautomer, stereoisomer, or a mixture of stereoisomers thereof, wherein:

$Z_1$, $Z_2$, $Z_3$, and $Z_4$ are independently chosen from CH and N, provided that at least two of $Z_1$, $Z_2$, $Z_3$, and $Z_4$ are CH;

$R_1$ is chosen from aryl, heteroaryl, and heterocycloalkenyl, each of which is optionally substituted with one or two groups independently chosen from alkynyl, heteroaryl, cyano, optionally substituted amino, halo, lower alkyl, and lower alkyl substituted with optionally substituted amino;

$L_1$ is chosen from O and $NR_4$;

$R_4$ is chosen from hydrogen and lower alkyl;

$L_2$ is $(CH_2)_m$ where m is 0, 1, or 2;

$R_2$ is chosen from hydrogen, aryl, aryl substituted with hydroxyl or lower alkoxy, heteroaryl, and heteroaryl substituted with hydroxyl or lower alkoxy, $R_5$ is chosen from lower alkyl, lower alkoxy, halo, and oxo (as a substituent on the heterocycloalkyl ring); and n is 0 or 1;

wherein the compound of Formula XIII, or a pharmaceutically acceptable salt thereof, is labeled with one or more positron-emitting isotopes;

and wherein the compound comprises a metabolically protected fluorine atom.

In some embodiments, the compound is a compound of Formula XIV:

XIV

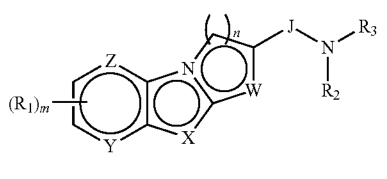

or an isotopically enriched analog, pharmaceutically acceptable salt, prodrug, tautomer, stereoisomer, or a mixture of stereoisomers thereof, wherein:

m is 0, 1, or 2;

n is 1 or 2;

J is C(=O) or $—CH_2—$;

X is S or N;

Y is CH or N;

Z is CH or N;

W is N or S;

for each occurrence, $R_1$ is independently chosen from halo, lower alkoxy, hydroxy, aryl, heteroaryl, cycloalkoxy, or lower alkyl, wherein the lower alkoxy, cycloalkoxy, lower alkyl, aryl, or heteroaryl are each optionally substituted with one, two, or three groups independently selected from lower alkoxy, alkenyl, $—NR_4R_5$, halo, or heteroaryl optionally substituted with one to three lower alkoxy;

$R_2$ is hydrogen or lower alkyl; and $R_3$ is alkyl, aryl, aralkyl, heterocycloalkyl, heterocycloalkenyl, heteroaryl, or heteroaralkyl, each of which is optionally substituted with one, two, or three groups independently chosen from hydroxy, lower alkoxy optionally substituted with lower alkoxy or halo, lower alkyl optionally substituted with halo, halo, heteroaryl, $—(CH_2)_tNR_4R_5$, oxo, cyano, or $—C(O)—NR_4R_5$, or $R_2$ and $R_3$ taken together with the nitrogen to which they are bound form a heterocycloalkyl ring, optionally substituted with one, two, or three groups independently chosen from hydroxy, lower alkoxy, lower alkyl, halo, or $—C(O)—NR_4R_5$;

t is 0, 1, or 2;

each $R_4$ is independently chosen from hydrogen or lower alkyl;

each $R_5$ is independently chosen from hydrogen or lower alkyl; or $R_4$ and $R_5$ taken together with the nitrogen to which they are bound form a heterocycloalkyl ring, optionally substituted with one, two, or three groups independently chosen from hydroxy, lower alkoxy, lower alkyl, halo, or $—C(O)—NR_6R_7$;

each $R_6$ is independently chosen from hydrogen or lower alkyl; and each $R_7$ is independently chosen from hydrogen or lower alkyl;

wherein the compound of Formula XIV, or a pharmaceutically acceptable salt thereof, is labeled with one or more positron-emitting isotopes;

and wherein the compound comprises a metabolically protected fluorine atom.

In some embodiments, the compound is a compound of Formula XV:

XV

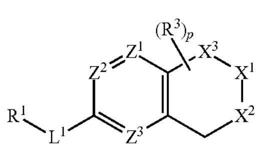

or an isotopically enriched analog, pharmaceutically acceptable salt, prodrug, tautomer, stereoisomer, or a mixture of stereoisomers thereof, wherein:

$Z^1$ and $Z^2$ are each independently CH, or one of $Z^1$ and $Z^2$ is N and the other is CH;

$Z^3$ is N or CH;

$L^1$ is —O—$C_{1-4}$alkylene, —O—$C_{1-4}$alkylene-O—, or —N($R^4$)C(=O)—;

one of $X^1$ and $X^2$ is N-$L^2$-$R^2$ and the other is $CH_2$;

$X^3$ is $CH_2$ or —O—$CH_2$—;

$L^2$ is —$(CH_2)_n$—, —C(=O)—, —C(=O)NH—, —C(=O)(O)—$(CH_2)_n$, or —S(=O)$_2$;

n is 0, 1, or 2;

$R^1$ is aryl or heteroaryl, each of which is optionally substituted with one or two substituents independently selected from halogen, haloalkyl, hydroxy, alkyl, alkoxy, haloalkoxy, and —N($R^4$)$_2$;

$R^2$ is aryl, alkyl, heteroaryl, heterocycloalkyl, or heterocycloalkenyl, each of which is optionally substituted with one or two substituents independently selected from halogen, haloalkyl, hydroxy, alkyl optionally substituted with alkenyl or alkoxy, alkoxy optionally substituted with alkenyl or alkoxy, haloalkoxy, heteroaryl, and —N($R^4$)$_2$;

p is 0, 1, or 2;

each $R^3$ is independently $C_{1-4}$alkyl, or two $R^3$ on the same carbon form oxo, where $R^3$ may substitute one or more ring carbon atoms of

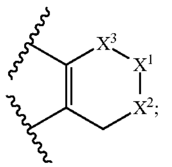

and each $R^4$ is independently H or $C_{1-4}$alkyl;

wherein the compound of Formula XV, or a pharmaceutically acceptable salt thereof, is labeled with one or more positron-emitting isotopes;

and wherein the compound comprises a metabolically protected fluorine atom.

In some embodiments, the compound is a compound of Formula XVI:

XVI

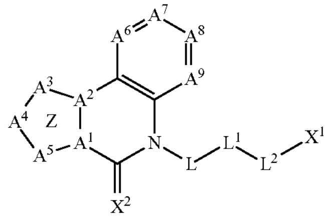

or an isotopically enriched analog, pharmaceutically acceptable salt, prodrug, tautomer, stereoisomer, or a mixture of stereoisomers thereof, wherein:

the compound is labeled with one or more positron-emitting isotopes;

$A^1$ is C;

$A^2$ is C or N;

$A^3$ is $CR^{21}$, $NR^3$, or N;

$A^4$ is $CR^{22}$, $NR^3$, or N;

$A^5$ is $CR^{23}$, $NR^3$, or N;

wherein ring Z formed by -$A^1$-$A^2$-$A^3$-$A^4$-$A^5$- is a 5-membered heteroaryl having up to three nitrogen atoms;

each of $R^{21}$, $R^{22}$, and $R^{23}$ is independently hydrogen, halo, cyano, hydroxy, amino, alkylamino, dialkylamino, $C_{1-4}$alkyl, $C_{1-4}$haloalkyl, $C_{1-4}$alkoxy, $C_{1-4}$haloalkoxy, or $C_{3-6}$cycloalkyl;

each $R^3$ is independently hydrogen, $C_{1-4}$alkyl, $C_{1-4}$haloalkyl, or $C_{3-6}$cycloalkyl;

$A^6$ is $CR^{11}$ or N, $A^7$ is $CR^{12}$ or N, $A^8$ is $CR^{13}$ or N, and $A^9$ is $CR^{14}$ or N, wherein no more than two of $A^6$, $A^7$, $A^8$, and $A^9$ is N;

each of $R^{11}$, $R^{12}$, $R^{13}$, and $R^{14}$ is hydrogen, halo, cyano, hydroxy, amino, alkylamino, dialkylamino, $C_{1-4}$alkyl, $C_{1-4}$haloalkyl, $C_{1-4}$alkoxy, or $C_{1-4}$haloalkoxy;

$X^1$ is $C_{1-6}$alkyl, $C_{3-10}$cycloalkyl, $C_{6-10}$aryl, heteroaryl, or heterocyclyl, wherein $X^1$ is optionally substituted with 1 to 4 $R^4$;

each $R^4$ is independently halo, cyano, hydroxy, amino, alkylamino, dialkylamino, $C_{1-4}$alkyl, $C_{1-4}$haloalkyl, $C_{1-4}$alkoxy, or $C_{1-4}$haloalkoxy;

$X^2$ is 0, S, or $NR^5$; $R^5$ is hydrogen, $C_{1-6}$alkyl, $C_{1-6}$haloalkyl, or $C_{1-6}$alkoxy;

L is —$(C(R^6)_2)_m$—, wherein m is 1, 2, 3, or 4;

each $R^6$ is independently hydrogen, halo, cyano, hydroxy, amino, alkylamino, dialkylamino, $C_{1-4}$alkyl, $C_{1-4}$haloalkyl, $C_{1-4}$alkoxy, or $C_{1-4}$haloalkoxy; or two $R^6$, together with any intervening atoms, join to form a 3- to 6-membered ring;

$L^1$ is C(O), C(O)$NR^a$, $NR^a$C(O), or O, or $L^1$ is absent;

$R^a$ is hydrogen, $C_{1-6}$alkyl, or $C_{1-6}$haloalkyl;

$L^2$ is $C_{1-2}$alkylene optionally substituted by 1 to 4 $R^7$, or $L^2$ is absent;

each $R^7$ is independently halo, cyano, hydroxy, amino, alkylamino, dialkylamino, $C_{1-4}$alkyl, $C_{1-4}$haloalkyl, $C_{1-4}$alkoxy, or $C_{1-4}$haloalkoxy;

and wherein the compound comprises a metabolically protected fluorine atom.

In some embodiments, the compound is a compound of Formula XVII:

XVII

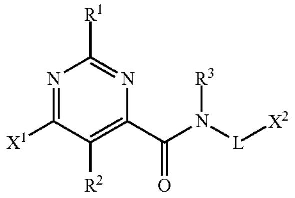

or an isotopically enriched analog, pharmaceutically acceptable salt, prodrug, tautomer, stereoisomer, or a mixture of stereoisomers thereof, wherein:

the compound is labeled with one or more positron-emitting isotopes;

$R^1$ is hydrogen, halo, $C_{1-6}$alkyl, $C_{1-6}$haloalkyl, $C_{1-6}$alkoxy, $C_{1-6}$haloalkoxy, or phenyl;

$R^2$ is hydrogen, halo, $C_{1-6}$alkyl, $C_{1-6}$haloalkyl, $C_{1-6}$alkoxy, or $C_{1-6}$haloalkoxy;

$R^3$ is hydrogen, $C_{1-6}$alkyl, or $C_{1-6}$haloalkyl;

$X^1$ is $C_{6-10}$aryl or heteroaryl, each of which is optionally substituted with 1 to 4 $R^4$;

$X^2$ is heteroaryl, heterocyclyl, or oxo-heterocyclyl, each of which is optionally substituted with 1 to 4 $R^6$;

each $R^4$ is independently halo, cyano, hydroxy, nitro, amino, alkylamino, dialkylamino, $C_{1-6}$alkyl optionally substituted with $R^5$, $C_{1-6}$haloalkyl, $C_{1-6}$hydroxyalkyl, $C_{1-6}$alkoxy optionally substituted with $R^5$, or $C_{1-6}$haloalkoxy;

each $R^5$ is independently halo, cyano, hydroxy, amino, alkylamino, dialkylamino, or $C_{1-6}$alkoxy;

each $R^6$ is independently halo, cyano, hydroxy, nitro, amino, alkylamino, dialkylamino, $C_{1-6}$alkyl optionally substituted with $R^7$, $C_{1-6}$haloalkyl, $C_{1-6}$hydroxyalkyl, $C_{1-6}$alkoxy optionally substituted with $R^7$, or $C_{1-6}$haloalkoxy;

each $R^7$ is independently halo, cyano, hydroxy, amino, alkylamino, dialkylamino, or $C_{1-6}$alkoxy;

L is $(C(R^8)_2)_n$;

n is 0, 1, or 2;

each $R^8$ is independently hydrogen, halo, $C_{1-6}$alkyl, $C_{1-6}$haloalkyl or $C_{1-6}$alkoxy;

or one of $R^3$ or $R^8$, together with the intervening atoms, forms a 3- to 6-membered saturated or partially unsaturated ring with $R^6$;

and wherein the compound comprises a metabolically protected fluorine atom.

In some embodiments, the compound is a compound of Formula XVIII:

XVIII

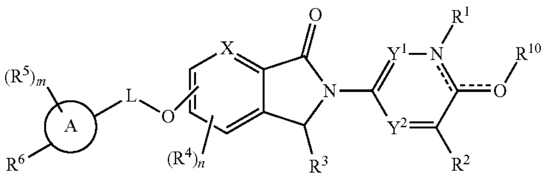

or an isotopically enriched analog, pharmaceutically acceptable salt, prodrug, tautomer, stereoisomer, or a mixture of stereoisomers thereof, wherein:

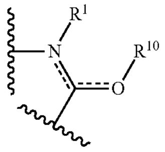 is 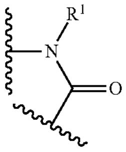 or 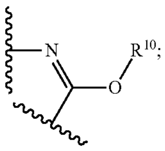

$R^1$, when present, is hydrogen, $C_{1-6}$alkyl, or $C_{1-6}$haloalkyl;

$R^{10}$, when present, is hydrogen, $C_{1-6}$alkyl, or $C_6$haloalkyl;

Ring A is 5- to 6-membered heteroaryl;

X is $CR^{11}$ or N;

$R^{11}$ is hydrogen, cyano, hydroxy, halo, $C_{1-6}$alkyl, $C_{1-6}$haloalkyl, or $C_{1-6}$alkoxy;

$Y^1$ is $CR^{12}$ or N;

$Y^2$ is $CR^{13}$ or N;

each of $R^{12}$ and $R^{13}$ is hydrogen, hydroxy, halo, $C_{1-6}$alkyl, $C_{1-6}$haloalkyl, or $C_{1-6}$alkoxy;

$R^2$ is hydrogen, hydroxy, halo, $C_{1-6}$alkyl, $C_{1-6}$haloalkyl, or $C_{1-6}$alkoxy;

L is $C_1$-$C_3$alkylene optionally substituted with 1 to 6 fluoro;

$R^3$ is hydrogen, fluoro, $C_{1-6}$alkyl, or $C_{1-6}$haloalkyl;

each $R^4$ is independently cyano, hydroxy, halo, $C_{1-6}$alkyl, $C_{1-6}$haloalkyl, or $C_{1-6}$alkoxy;

each $R^5$ is independently cyano, hydroxy, halo, $C_{1-6}$alkyl, $C_{1-6}$haloalkyl, or $C_{1-6}$alkoxy;

$R^6$ is hydrogen, cyano, hydroxy, halo, $C_{1-6}$alkyl, —$SO_2F$, or $L^1$-$R^7$;

$L^1$ is —O—, —$SO_2$—, or —$OSO_2$—;

$R^7$ is hydrogen, $C_{1-6}$alkyl, or $C_{1-6}$haloalkyl, wherein the $C_{1-6}$alkyl or C-haloalkyl, of $R^7$ is optionally substituted with —$SO_2$-aryl, —$OSO_2$-aryl, 1 to 6 deuterium atoms, or a combination thereof, and wherein the —$SO_2$-aryl or —$OSO_2$-aryl is further optionally substituted with cyano, hydroxy, halo, $C_{1-6}$alkyl, $C_{1-6}$haloalkyl, or $C_{1-6}$alkoxy;

m is 0, 1, 2, or 3; and n is 0, 1, or 2;

wherein the compound of Formula XVIII, or a pharmaceutically acceptable salt thereof, is labeled with one or more positron-emitting isotopes;

and wherein the compound comprises a metabolically protected fluorine atom.

In some embodiments, the compound is a compound of Formula XVIII:

XVIII

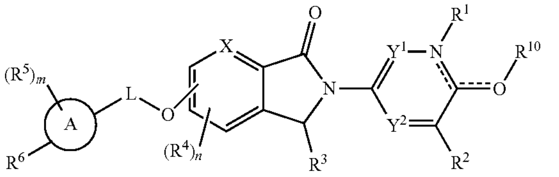

or an isotopically enriched analog, pharmaceutically acceptable salt, prodrug, tautomer, stereoisomer, or a mixture of stereoisomers thereof, wherein:

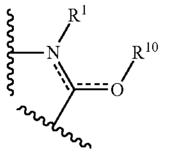 is 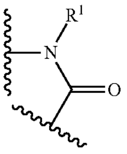 or 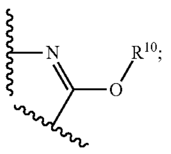

$R^1$, when present, is hydrogen, $C_{1-6}$alkyl, or $C_{1-6}$haloalkyl;

$R^{10}$, when present, is hydrogen, $C_{1-6}$alkyl, or $C_{1-6}$haloalkyl;

Ring A is 5- to 6-membered heteroaryl;

X is $CR^{11}$ or N;

$R^{11}$ is hydrogen, cyano, hydroxy, halo, $C_{1-6}$alkyl, $C_{1-6}$haloalkyl, or $C_{1-6}$alkoxy;

$Y^1$ is $CR^{12}$ or N;

$Y^2$ is $CR^{13}$ or N;

each of $R^{12}$ and $R^{13}$ is hydrogen, hydroxy, halo, $C_{1-6}$alkyl, $C_{1-6}$haloalkyl, or $C_{1-6}$alkoxy;

$R^2$ is hydrogen, hydroxy, halo, $C_{1-6}$alkyl, $C_{1-6}$haloalkyl, or $C_{1-6}$alkoxy;

L is $C_1$-$C_3$alkylene optionally substituted with 1 to 6 fluoro;

$R^3$ is hydrogen, fluoro, $C_{1-6}$alkyl, or $C_{1-6}$haloalkyl;

each $R^4$ is independently cyano, hydroxy, halo, $C_{1-6}$alkyl, $C_{1-6}$haloalkyl, or $C_{1-6}$alkoxy;

each $R^5$ is independently cyano, hydroxy, halo, $C_{1-6}$alkyl, $C_{1-6}$haloalkyl, or $C_{1-6}$alkoxy;

$R^6$ is hydrogen, cyano, hydroxy, halo, $C_{1-6}$alkyl, —$SO_2$F, or $L^1$-$R^7$;

$L^1$ is —O—, —$SO_2$—, or —$OSO_2$—;

$R^7$ is hydrogen, $C_{1-6}$alkyl, or $C_{1-6}$haloalkyl, wherein the $C_{1-6}$alkyl or $C_{1-6}$haloalkyl, of $R^7$ is optionally substituted with —$SO_2$-aryl, —$OSO_2$-aryl, 1 to 6 deuterium atoms, or a combination thereof, and wherein the —$SO_2$-aryl or —$OSO_2$-aryl is further optionally substituted with cyano, hydroxy, halo, $C_{1-6}$alkyl, $C_{1-6}$haloalkyl, or $C_{1-6}$alkoxy;

m is 0, 1, 2, or 3; and n is 0, 1, or 2;

and wherein the compound comprises a metabolically protected fluorine atom.

In some embodiments, the compound is a compound of Formula XIX:

XIX

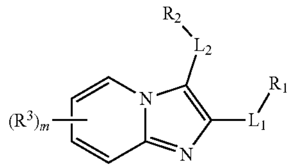

or an isotopically enriched analog, pharmaceutically acceptable salt, prodrug, tautomer, stereoisomer, or a mixture of stereoisomers thereof, wherein:

$L_1$ is —CH═CH— or $L_1$ is absent;

$R_1$ is chosen from phenyl or heteroaryl, each of which is optionally substituted with one, two, or three groups independently chosen from cyano, halo, heteroaryl, lower alkyl, lower alkyl substituted with one or two substituents independently chosen from lower alkoxy substituted with heteroaryl, —C(O)O-lower alkyl, hydroxyl, lower alkynyloxy, lower alkoxy, and lower alkoxy substituted with one or two substituents independently chosen from halo, heterocycloalkyl, heteroaryl, heteroaryl substituted with lower alkoxy, optionally substituted amino, alkyl substituted with heteroaryl, and alkyl substituted with heteroaryl substituted with lower alkoxy; or $R_1$ is phenyl substituted with two groups, which taken together with the carbon atoms to which they are bonded form a heterocycloalkenyl ring wherein said phenyl is further optionally substituted with a substituent chosen from halo, heteroaryl, and optionally substituted amino;

$L_2$ is —N($R_4$)— or $L_2$ is absent;

$R_2$ is chosen from hydrogen, lower alkyl, and lower alkyl substituted with lower alkoxy, amino, (alkyl)amino, (dialkyl)amino, or hydroxy;

for each occurrence, $R_3$ is independently chosen from halo, cyano, lower alkoxy, lower alkyl optionally substituted with amino, (alkyl)amino, or di(alkyl)amino, and ethynyl optionally substituted with tri(alkyl)silyl;

$R_4$ is chosen from hydrogen and lower alkyl; and m is 0, 1, or 2, wherein the compound of Formula XIX, or a pharmaceutically acceptable salt thereof, is labeled with one or more positron-emitting isotopes;

and wherein the compound comprises a metabolically protected fluorine atom.

Diagnostic Methods and Uses

In some embodiments, a method of detecting the presence or absence of a protein susceptible to aggregation in an individual is provided, comprising administering an effective amount of a compound or an imaging agent described herein to an individual, and generating an image of a body part or body area of the individual. Generating an image of a body part or body area of the individual may comprise generating an image to detect the presence or absence of a protein susceptible to aggregation in the image. Thus, the compounds disclosed herein are useful for detecting a disease or condition mediated, at least in part, by a protein susceptible to protein aggregation. In some embodiments, the presence or absence of a protein aggregate corresponds to the presence or absence of a neurodegenerative disease. In some embodiments, the neurodegenerative disease is selected from Alzheimer's disease, amyotrophic lateral sclerosis, Huntington's disease, Parkinson's disease, Prion disease, and spinocerebellar ataxias.

Provided are methods of generating diagnostic images, and of detecting the presence or absence of a protein susceptible to aggregation, using positron emission tomography (PET). PET imaging may be conducted as known to those of skill in the art, or as follows. PET imaging may involve the administration of a positron-emitting radionuclide tracer, for example, a compound or imaging agent described herein, to an individual. The tracer is then given sufficient time to associate with the protein of interest, at which time the individual is placed in a scanning device comprising a ring of scintillation detectors. An emitted positron travels through the individual's tissue for a short (isotope-dependent) distance, until it interacts with an electron. The interaction annihilates both the electron and the positron, producing a pair of photons. The photons are detected by a scintillator in the scanning device. Photons that do not arrive in pairs are ignored.

Also provided are methods of generating diagnostic images, and of detecting the presence or absence of a protein susceptible to aggregation, comprising PET with concurrent computed tomography imaging (PET/CT), with concurrent magnetic resonance imaging (PET/MRI), or single-photon emission computed tomography (SPECT) imaging. In general, computed tomography uses X-rays or gamma rays to detect the structure of the brain, while magnetic resonance imaging uses magnetic fields and radio waves.

Thus, a compound or an imaging agent described herein may be administered by methods known in the art including those described herein. The compound or imaging agent may enter circulation and bind to the protein susceptible to aggregation, or to aggregates thereof. When the compound or imaging agent is labeled with a positron-emitting isotope, the emitted particles may be detected.

In some embodiments, the compound or imaging agent is administered into the individual's vascular system. The compound or imaging agent may pass through the blood-brain barrier. Thus, generating an image may comprise generating an image of at least part of the individual's brain, for example, the part to which the compound has distributed.

Also provided are methods of generating diagnostic images, and of detecting the presence or absence of a protein susceptible to aggregation, in a biological sample comprising contacting the biological sample with an effective amount of a compound or an imaging agent described herein and generating an image associated with the biological sample. In some embodiments, the contacting and the generating may be conducted in vitro. In some embodiments the contacting is in vivo and the generating is in vitro.

Also provided are methods for detecting the presence or absence of a pathologic process associated with a protein susceptible to protein aggregation, for example huntingtin protein (HTT protein), in an individual comprising: administering an effective amount of a compound or an imaging agent described herein; generating an image to detect the presence or absence of huntingtin protein (HTT protein) in the image; and detecting the presence or absence of a pathologic process, e.g., a neurodegenerative disease. In some embodiments, the HTT protein is present as monomers, oligomers, or aggregates, or a combination thereof. In some embodiments, the protein susceptible to aggregation is huntingtin protein (HTT protein). The HTT protein may be mutant. In some embodiments, the HTT protein is found in the brain, for example, in basal ganglia.

In some embodiments, the body part or body area is selected from head, spinal cord, limb, thorax, and/or abdomen. In some embodiments, the body part or body area is brain. In some embodiments, the HTT protein is found in basal ganglia. In some embodiments, the protein susceptible to aggregation, e.g., HTT protein, is present in the brain, liver, heart, and/or muscle of the individual. In some embodiments, generating an image comprises positron emission tomography (PET) imaging, PET with concurrent computed tomography imaging (PET/CT), PET with concurrent magnetic resonance imaging (PET/MRI), single-photon emission computed tomography (SPECT) imaging, or a combination thereof. In some embodiments, generating an image comprises PET imaging. In some embodiments, the protein susceptible to aggregation, e.g., HTT protein, is present in the basal ganglia, cortex, hippocampus, and/or brain stem of the brain of the individual. In some embodiments, the protein susceptible to aggregation, e.g., HTT protein, is present as monomers, oligomers, or aggregates, or a combination thereof.

In some embodiments, the individual has, or is discovered to have, Huntington's disease.

Also provided are methods for detecting the presence or absence of a pathologic process associated with β-amyloid protein in an individual comprising: administering an effective amount of a compound or an imaging agent described herein; generating an image of a body part or body area of the individual; and detecting the presence or absence of the pathologic process. In some embodiments, the individual has, or is discovered to have, Alzheimer's Disease (AD).

Also provided are diagnostic methods of using a compound or an imaging agent described herein to monitor disease progression in a patient by quantifying the change in levels of the protein susceptible to aggregation in the patient.

In some embodiments, provided is a compound having suitable protein aggregate, e.g., HTT protein aggregate or β-amyloid protein aggregate, binding kinetics to function as imaging agents. Thus, a compound described herein may be characterized by one or more of: 1) a high affinity for such protein aggregates; 2) a low affinity for nearby structures; and/or 3) slow dissociation kinetics from such protein aggregates. Dissociation kinetics may be expressed as the dissociation rate constant $k_{diss}$, as defined in the equation below (wherein A and B refer to the protein aggregate and the imaging agent, and $k_{assn}$ is the association rate constant):

$$d[AB]/dt=k_{assn}[A][B]-k_{diss}[AB]$$

In some embodiments, the effective amount of the compound or imaging agent described herein comprises from about 0.1 to about 20 mCi. In some embodiments, the effective amount of the compound or imaging agent described herein comprises about 0.1, about 0.3, about 0.5, about 0.7, about 1, about 3, about 5, about 7, about 10, about 15, or about 20 mCi, or a range of values therebetween. In some embodiments, the effective amount of the compound or imaging agent described herein comprises about 10 mCi.

Suitable radionuclides that may be incorporated in a compound described herein include, but are not limited to, $^{3}H$ (also written as T), $^{11}C$, $^{18}F$, $^{35}S$, $^{123}I$, $^{125}I$, $^{75}Br$, $^{76}Br$, $^{77}Br$, $^{82}Br$, $^{131}I$, $^{15}O$, $^{13}N$, and $^{211}At$. The radionuclide that is incorporated in the compound will depend on the specific imaging application. In some embodiments including PET imaging, compounds that incorporate a radionuclide selected from $^{11}C$, $^{18}F$, $^{123}I$, $^{131}I$, $^{75}Br$, $^{76}Br$ or $^{77}Br$ may be used. In certain applications incorporation of a chelating radionuclide such as $^{99m}Tc$ may also be useful. In some embodiments, $^{18}F$ may be preferable over $^{11}C$ because with the longer half-life of $^{18}F$, imaging can be carried out long enough to allow a stronger signal to develop. In some embodiments, a compound or imaging agent described herein can be labeled with a positron emitting radionuclide or a gamma emitting radionuclide. Some examples of positron-emitting radionuclides include $^{15}O$, $^{13}N$, $^{11}C$, $^{18}F$, $^{76}Br$, and $^{124}I$, which have half-lives of about 2, 10, 20, 110 minutes, 16 hours, and 4.2 days respectively.

In some embodiments, a compound or an imaging agent described herein may be labelled with a positron emitter selected from $^{11}C$ and $^{18}F$. Methods for the introduction of $^{11}C$ may include, but are not limited to, alkylation with [$^{11}C$]iodomethane or [$^{11}C$]methyl triflate. Carbon-11 has a half-life of approximately 20 minutes, thus $^{11}C$ generally needs to be generated in an on-site cyclotron, and may be produced as [$^{11}C$]carbon dioxide. The [$^{11}C$]carbon dioxide is converted to the chemical species appropriate for the radiosynthesis (generally [$^{11}C$]iodomethane or the like), and the synthesis of the radiopharmaceutical is completed and used on-site in a PET imaging study after the appropriate radiochemical purity and specific activity have been determined. Typical methods of introducing $^{18}F$ include but are not limited to nucleophilic and electrophilic methods. Nucleophilic methods include displacement of a halide, tosylate, or other leaving group with labeled cesium fluoride, potassium fluoride, tetrabutylammonium fluoride tetramethylammonium fluoride, or potassium fluoride kryptofix-222. Electrophilic reagents that may be suitable for introducing [$^{18}F$]isotopes include labeled diethylaminosulfur trifluoride (DAST), bis(2-methoxyethyl)aminosulfur trifluoride (Deoxofluor), N-fluorobenzenesulfonimide (NFSI), N-fluoropyridinium salts, 1-chloromethyl-4-fluoro-1,4-diazoniabicyclo[2.2.2]octane bis(tetrafluoroborate) (Selectfluor), N-fluoropyridinium triflate, xenon fluoride, 2-pyridinesulfonyl fluoride (PyFluor), 3-pyridinesulfonyl fluoride, 4-pyridinesulfonyl fluoride, 4-chloro-2-pyridinesulfonyl fluoride, ethenesulfonyl fluoride, fluoro-benziodoxole, p-fluorophenylaminosulfur trifluoride, p-nitrophenylaminosulfur trifluoride, or pentafluorophenylaminosulfur trifluoride. General methods for the introduction of positron emitters are described in the literature (e.g., see Miller et al., *Angewandte Chemie International Edition,* 47 (2008), 8998-9033; Jacobson, O. et al., Bioconjugate Chem., 26 (2015), 1-18; Deng, X. et al., *Angewandte Chemie International Edition,* 58(9), (2019), 2580-2605).

Fluorine-18 has a half-life of approximately 110 minutes, thus synthesis of [$^{18}$F] radiopharmaceuticals need not necessarily have to occur at the site of the cyclotron nor proximal to the PET imaging study center. Fluorine-18 is also thought to exhibit favorable nuclear and physical characteristics, including high positron decay ratio (97%), favorable half-life (109.7 min), and low positron energy (up to 0.635 MeV). The positron energy may correspond to a short diffusion range (<2.4 mm) in vivo that may provide superior resolution limits of a PET image.

Methods of carrying out PET imaging are as described in the Examples herein, and as found in the literature. Examples of studies include "Carbon 11-labeled Pittsburgh compound B and carbon 11-labeled (R)-PKI 1195 positron emission tomographic imaging in Alzheimer's disease" Arch. Neurol. 2009; 66(1): 60-67.

As will be recognized, the steps of the methods described herein need not be performed any particular number of times or in any particular sequence. Additional objects, advantages and novel features of the disclosure will become apparent to those skilled in the art upon examination of the examples provided below, which are intended to be illustrative and are not limiting.

Indications and Treatment Methods

A compound or an imaging agent described herein may be useful for treating a disease or condition mediated, at least in part, by a protein susceptible to aggregation. In some embodiments, a compound or an imaging agent described herein is useful for treating a disease or condition mediated, at least in part, by HTT protein.

In some embodiments, treatment of a disease or condition mediated, at least in part, by a protein susceptible to aggregation may comprise administration of a compound or an imaging agent described herein. Treatment may include coadministration of a compound or an imaging agent described herein and one or more other active agents and/or therapies. Thus, in some embodiments, provided is a method of treating or preventing a disease or condition mediated, at least in part, by a protein susceptible to aggregation in a patient in need thereof, comprising administering to the patient a therapeutically effective amount of a compound or an imaging agent described herein.

Exemplary diseases and conditions are as follows.

Huntington's Disease (HD)

Huntington's disease (HD) is an inherited progressive neurodegenerative disorder, characterized by motor, cognitive, and psychiatric deficits as well as neurodegeneration and brain atrophy. Atrophy may begin in the striatum and cortex and extend to other subcortical brain regions. HD belongs to a family of neurodegenerative diseases in which an expanded CAG repeat tract results in long stretches of polyglutamine (polyQ) in an encoded protein. The family also includes dentatorubral-pallidoluysian atrophy (DRPLA), spinal and bulbar muscular atrophy (SBMA) and the spinocerebellar ataxias (SCAs). In HD, the selective neurodegeneration of the γ-aminobutyric acid-releasing spiny-projection neurons of the striatum had been observed, although neuron loss in many other brain regions has also been reported. Symptoms of HD include loss of motor control, psychiatric symptoms, memory and/or cognitive impairment.

HD protein huntingtin (HTT protein) is a 348-kDa multidomain protein that contains a polymorphic glutamine/proline-rich domain at its amino-terminus. The number of CAG repeats in the $IT_{15}$ gene that encodes HTT varies from 6 to 35 in healthy individuals; repeats of 36 or more define an HD allele. The length of the CAG expansion has been inversely correlated with age of disease onset, with cases of juvenile onset characterized by expansions of more than 60 repeats. The longer polyQ domain is believed to induce conformational changes in the HTT protein, which causes it to form intracellular aggregates that, in many, manifest as nuclear inclusions. However, aggregates can also form outside the nucleus. HTT protein is present in the nucleus, cell body, dendrites and nerve terminals of neurons, and is also associated with a number of organelles including the Golgi apparatus, endoplasmic reticulum and mitochondria.

The part of the brain most affected by HD, and thus believed to be most likely to contain HTT protein abnormalities, is a group of nerve cells at the base of the brain known collectively as the basal ganglia. The basal ganglia organize muscle-driven movements of the body, or "motor movement." The major components of the basal ganglia are the caudate and the putamen (together known as the striatum) and the globus pallidus (external and internal regions). The substantia nigra and the subthalamic nucleus are often included as part of the basal ganglia as well.

Basal ganglia are a group of subcortical nuclei responsible primarily for motor control, as well as other roles such as motor learning, executive functions and behaviors, and emotions. Disruption of the basal ganglia network are believed to contribute to several movement disorders. Normal function of the basal ganglia requires fine tuning of neuronal excitability within each nucleus to determine the degree of movement facilitation or inhibition at any given moment. This is mediated by the complex organization of the striatum, where the excitability of medium spiny neurons is controlled by several pre- and postsynaptic mechanisms as well as interneuron activity, and secured by several recurrent or internal basal ganglia circuits. The motor circuit of the basal ganglia has two entry points, the striatum and the subthalamic nucleus, and an output, the globus pallidus pars interna, which connects to the cortex via the motor thalamus.

For example, treatment may proceed by degradation of mutant huntingtin (mHTT) by a proteolysis targeting chimera (PROTAC) or bifunctional chimera comprising a compound described herein. Conjugation of a compound targeting mHTT to form a heterobifunctional composition are useful in such treatment. Examples of such conjugates are provided in International Application No. WO 2020/176424, incorporated herein by reference in its entirety. Such conjugates may have a formula

W-L-ULM wherein:

- W is a compound targeting mutant huntingtin protein (mHTT), such as a compound described herein;
- L is a bond or linking moiety optionally substituted with B;
  - B is a moiety that crosses the blood brain barrier and/or enhances cell permeability; and
- ULM is a E3 ubiquitin ligase targeting moiety;

where L, B, and ULM may be as described in WO 2020/176424.

In some embodiments, W is a moiety of Formula X as described herein.

In specific embodiments, W is a moiety of Formula X:

X

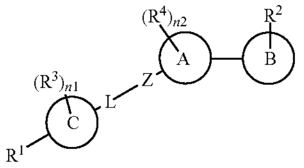

or an isotopically enriched analog, pharmaceutically acceptable salt, prodrug, tautomer, stereoisomer, or a mixture of stereoisomers thereof, wherein:

Ring A is a 9-membered bicyclic heteroaryl;

Ring B is a 6-membered heterocyclyl, 6-membered oxo-heterocyclyl, or 6-membered heteroaryl;

Ring C is a 6-membered heteroaryl;

Z is O, S, NH, or $N(C_{1-3}alkyl)$;

L is $CH_2$, $CH(C_{1-3}alkyl)$, $C(C_{1-3}alkyl)_2$, or C(O);

$R^1$ is cyano, halo, hydroxy, nitro, $C_{1-6}$alkyl, $C_{2-6}$alkenyl, $C_{2-6}$alkynyl, $C_{1-6}$haloalkyl, deuterated $C_{1-6}$haloalkyl, $C_{1-6}$alkoxy, $C_{1-6}$haloalkoxy, deuterated $C_{1-6}$haloalkoxy, $C_{1-6}$alkylthio, $C_{3-8}$ cycloalkyl, heterocyclyl, heteroaryl, amino, alkylamino, dialkylamino, or —O-alkylene-O—$SO_2$—$R^5$;

$R^5$ is aryl optionally substituted by alkyl;

$R^2$ is absent, cyano, halo, hydroxy, nitro, $C_{1-6}$alkyl, $C_{1-6}$haloalkyl, deuterated $C_{1-6}$haloalkyl, $C_{1-6}$alkoxy, $C_{1-6}$haloalkoxy, deuterated $C_{1-6}$haloalkoxy, $C_{1-6}$alkylthio, $C_{3-8}$ cycloalkyl, heterocyclyl, heteroaryl, amino, alkylamino, or dialkylamino;

$R^3$ is cyano, halo, hydroxy, nitro, $C_{1-6}$alkyl, $C_{1-6}$haloalkyl, deuterated $C_{1-6}$haloalkyl, $C_{1-6}$alkoxy, $C_{1-6}$haloalkoxy, deuterated $C_{1-6}$haloalkoxy, $C_{1-6}$alkylthio, $C_{3-8}$ cycloalkyl, heterocyclyl, heteroaryl, amino, alkylamino, or dialkylamino;

$R^4$ is cyano, halo, hydroxy, nitro, $C_{1-6}$alkyl, $C_{1-6}$haloalkyl, deuterated $C_{1-6}$haloalkyl, $C_{1-6}$alkoxy, $C_{1-6}$haloalkoxy, deuterated $C_{1-6}$haloalkoxy, $C_{1-6}$alkylthio, $C_{3-8}$ cycloalkyl, heterocyclyl, heteroaryl, amino, alkylamino, or dialkylamino;

n1 is 0, 1, or 2; and n2 is 0, 1, or 2;

in which one of $R^1$, $R^2$, $R^3$, or $R^4$ comprises a moiety substitutable by L or ULM;

ULM is a moiety of formula:

(XX)

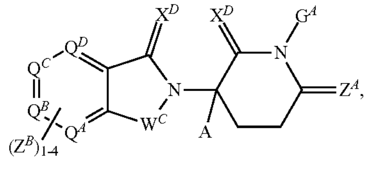

(XXI)

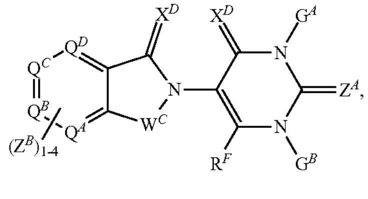

-continued (XXII)

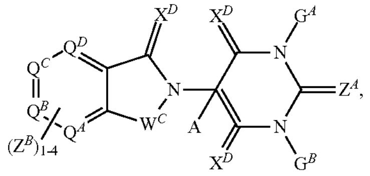

(XXIII)

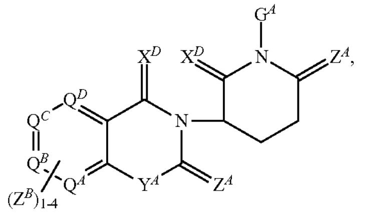

(XIV)

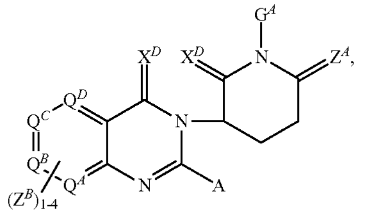

or (XV)

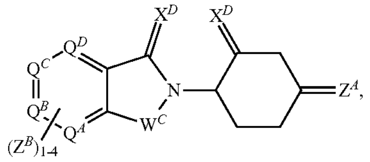

$W^C$ is $CH_2$, $CHR^E$, C═O, $SO_2$, NH, or N-alkyl;

each $X^D$ is independently selected from O, S, and $H_2$;

$Y^A$ is $CH_2$, —C═$CR^F$, NH, N-alkyl, N-aryl, N-heteroaryl, N-cycloalkyl, N-heterocyclyl, O, or S;

$Z^A$ is O, S, or $H_2$, provided that both $X^D$ and $Z^A$ cannot be $H_2$;

$G^A$ and $G^B$ are each independently selected from H, alkyl optionally substituted with $R^F$, OH, $R^FOCOOR^E$, $R^FOCONR^ER^G$, —$CH_2$-heterocyclyl optionally substituted with $R^F$, and benzyl optionally substituted with $R^F$;

$Q^A$, $Q^B$, $Q^C$, and $Q^D$ are each independently $CR^F$, N, or N-oxide;

A is H, alkyl, cycloalkyl, Cl, or F;

$R^E$ is —$CONR^FR^G$, —$OR^F$, —$NR^FR^G$, —$SR^F$, —$SO_2R^F$, —$SO_2NR^FR^G$, —$CR^FR^G$, —$CR^FNR^FR^G$, aryl, heteroaryl, optionally substituted alkyl, cycloalkyl, heterocycloalkyl, —$P(O)(OR^F)(R^G)$, —$P(O)R^FR^G$, —$OP(O)(OR^F)(R^G)$, —$OP(O)R^FR^G$, halo, —$CF_3$, —CN, —$NR^FSO_2NR^FR^G$, —$NR^FCONR^FR^G$, —$CONR^FCOR^G$, —$NR^FC$(═N—CN)$NR^FR^G$, —C(═N—CN)$NR^FR^G$, —$NR^FC$(═N—CN)$R^G$, —$NR^FC$(═C—$NO_2$)$NR^FR^G$, —$SO_2NR^FCOR^G$, —$NO_2$, —$CO_2R^F$, —C(C═N—$OR^F$)$R^G$, —$CR^F$═$CR^FR^G$, —$CCR^F$, —S(C═O)(C═N—$R^F$)$R^G$, —$SF_5$, or —$OCF_3$;

$R^F$ and $R^G$ are each independently selected from a bond, H, N, N-oxide, alkyl, cycloalkyl, aryl, heteroaryl, heterocyclyl, or —$C(O)R^H$, wherein the alkyl, cycloalkyl, aryl, heteroaryl, or heterocyclyl are optionally substituted;

$R^H$ is hydrogen, alkyl, aryl, heteroaryl, cycloalkyl, or heterocycloalkyl; and $Z^B$ is a functional group or atom, and optionally one of which is modified to be covalently joined to Formula X;

wherein a point of attachment of W to L-ULM is at any substitutable atom of Formula X; the linking moiety is of the formula:

$$-G_1-((CH_2)_a-G_2)_c-(CH_2)_b-G_3-$$

wherein:

each of $G_1$, $G_2$, and $G_3$ are independently a bond, —$NR_{28}$—, —O—, —$S(O)_{0-2}$—, —$NR_{28}C(O)$—, —$C(O)NR_{28}$—, —$NR_{28}S(O)_2$—, —$S(O)_2NR_{28}$—, —$CR_{29}$═N—$NR_{28}$—, —$NR_{28}$—N═$CR_{29}$—, —C(O)—, alkylene, heteroalkylene, alkenylene, heteroalkenylene, alkynylene, heteroalkynylene, arylene, heteroarylene, cycloalkylene, or heterocycloalkylene; wherein each alkylene, heteroalkylene, alkenylene, heteroalkenylene, alkynylene, heteroalkynylene, arylene, heteroarylene, cycloalkylene, or heterocycloalkylene is independently optionally substituted with one to five substituents independently selected from oxo, halo, $C_{1-4}$ alkyl, $C_{1-4}$ alkoxy, and $C_{1-4}$ haloalkyl;

each $R_{28}$ is independently hydrogen, $C_{1-4}$ alkyl, $C_{1-4}$ haloalkyl, aryl, heteroaryl, cycloalkyl, or heterocyclyl;

$R_{29}$ is $C_{1-4}$ alkyl, $C_{1-4}$ haloalkyl, aryl, heteroaryl, cycloalkyl, or heterocyclyl;

a and b are each independently 0, 1, 2, 3, 4, 5, 6, 7, or 8; and c is an integer between 0-20;

and wherein the linking moiety is optionally substituted, on a substitutable atom, with:

$$(-G_4-(CH_2)_d-G_5-)_e-B$$

each of $G^4$ and $G^5$ are independently a bond, —$NR_{28}$—, —O—, —$S(O)_{0-2}$—, —$NR_{28}C(O)$—, —$C(O)NR_{28}$—, —$NR_{28}S(O)_2$—, —$S(O)_2NR_{28}$—, —$CR_{29}$═N—$NR_{28}$—, —$NR_{28}$—N═$CR_{29}$—, —C(O)—, alkylene, heteroalkylene, alkenylene, heteroalkenylene, alkynylene, heteroalkynylene, arylene, heteroarylene, cycloalkylene, or heterocycloalkylene; wherein each alkylene, heteroalkylene, alkenylene, heteroalkenylene, alkynylene, heteroalkynylene, arylene, heteroarylene, cycloalkylene, or heterocycloalkylene is independently optionally substituted with one to five substituents independently selected from oxo, halo, $C_{1-4}$ alkyl, $C_{1-4}$ alkoxy, and $C_{1-4}$ haloalkyl;

d and e are each independently 0, 1, 2, 3, 4, 5, 6, 7, or 8; and

B is a carrier peptide, cholesterol, or a carrier peptide conjugated (e.g. via a linking moiety as described herein or covalently bonded) to cholesterol, for example, B may be Angiopep2, ApoE-I, ApoE-II, ApoB, THR, Peptide-22, L57, TGN, leptin30, RVG29, nipah virus envelope (env.) HR region conjugated to cholesterol, newcastle disease virus conjugated to cholesterol, or measles virus e tide conjugated to cholesterol; specific examples of B moieties include those in the table below:

| Peptide | Peptide sequence | SEQ ID NO. |
|---|---|---|
| Angiopep2 | TFFYGGSRGKRNNFKTEEY | 1 |
| ApoE-I | TEELRVRLASHLRKLRKRLLRDA | 2 |
| ApoE-II | Ac-(LRKLRKRLL)2-CONH2 | 3 |
| ApoB | SVIDALQYKLEGTTRLTRKRGLKLATALSLSNKFVEGS | 4 |
| THR | THRPPMWSPVWP-NH2 and retro-inverso | 5 |
| Peptide-22 | Ac-CMPRLRGC (cycle) | 6 |
| L57 | TWPKHFDKHTFYSILKLGKH | 7 |
| TGN | TGNYKALHPHNG | 8 |
| Leptin30 | YQQILTSMPSRNVIQISNDLENLRDLLHVL | 9 |
| RVG29 | YTIWMPENPRPGTPCDIFTNSRGKRASNG-COOH | 10 |
| Nipah Virus Env. HR region +Chol | Ac-VALDPIDISIVLNKIKSDLEESKEWIRRSNKILDSI-PEG4-Cholesterol | 11 |
| Newcastle disease virus peptide conjugated to cholesterol | Ac-VNKKIEEIDKKIEELNKKLEELEKKLEEVNKK-Peg4-Cholesterol | 12 |
| Measles virus peptide and cholesterol | Ac-PPISLERLDVGTNLGNAIAKLEDAKELLESSDQILR-PEG4-Cholesterol | 13 |

In some embodiments, W is moiety of Formula I, Formula La, or Formula Ib, in which one of $R^1$, $R^2$, or $R^3$ comprises a group substitutable by L or ULM.

The administration of a compound described herein may result in a decrease, for example, at least a 10% decrease (e.g., at least 15%, 20%, 25%, 30%, 35%, 40%, 45%, 50%, 55%, 60%, 65%, 70%, 75%, 80%, 85%, 90% or 100%) in one or more symptoms of a disease or condition described herein. The disease or condition may be a disorder of the nervous system that is secondary to a disease, condition, or therapy having a primary effect outside of the nervous system; an injury to the nervous system caused by physical, mechanical or chemical trauma; autoimmune neural degeneration; neurodegeneration secondary to infection; and/or ocular neurodegeneration. Symptoms of nerve degeneration include, e.g., tremors, slowness of movement, ataxia, loss of balance, depression, decreased cognitive function, short term memory loss, long term memory loss, confusion, changes in personality, language difficulties, loss of sensory perception, sensitivity to touch, numbness in extremities, muscle weakness, muscle paralysis, muscle cramps, muscle spasms, significant changes in eating habits, excessive fear or worry, insomnia, delusions, hallucinations, fatigue, back pain, chest pain, digestive problems, headache, rapid heart rate, dizziness, blurred vision, shadows or missing areas of vision, metamorphopsia, impairment in color vision, decreased recovery of visual function after exposure to bright light, and loss in visual contrast sensitivity.

A neurodegenerative disease is a disease or condition in which the function of a subject's nervous system becomes impaired. Examples of neurodegenerative diseases include, e.g., Alexander's disease, Alper's disease, Alzheimer's disease, Amyotrophic lateral sclerosis, Ataxia telangiectasia, Batten disease (also known as Spielmeyer-Vogt-Sjogren-Batten disease), Bovine spongiform encephalopathy (BSE), Canavan disease, Cockayne syndrome, Corticobasal degeneration, Creutzfeldt-Jakob disease, frontotemporal dementia, Gerstmann-Straussler-Scheinker syndrome, Huntington's disease, HIV-associated dementia, Kennedy's disease, Krabbe's disease, kuru, Lewy body dementia, Machado-Joseph disease (Spinocerebellar ataxia type 3), Multiple sclerosis, Multiple System Atrophy, Narcolepsy, Neuroborreliosis, Parkinson's disease, Pelizaeus-Merzbacher Disease, Pick's disease, Primary lateral sclerosis, Prion disease, Refsum's disease, Sandhoff disease, Schilder's disease, Subacute combined degeneration of spinal cord secondary to Pernicious Anaemia, Schizophrenia, Spinocerebellar ataxia, Spinal muscular atrophy, Steele-Richardson-Olszewski disease, insulin resistance, or Tabes *dorsalis.*

In some embodiments, the disease or condition is selected from Huntington's disease (HD), dentatorubral-pallidoluysian atrophy, spinal and bulbar muscular atrophy, spinocerebellar ataxia, spinal cord and/or brain injury, chronic pulmonary hypertension, Parkinson's disease, amyotrophic lateral sclerosis, cerebral cavernous malformation, cardiovascular disease, Alzheimer's disease (AD), glaucoma, multiple sclerosis (MS), corneal lesions, diabetes, chronic and/or neuropathic pain, stroke, ischemia, retinopathy, spinal muscular atrophy (SMA), erectile dysfunction, nephropathy (non-hypertensive), hypertensive nephropathy, hypertension (high blood pressure), optic nerve lesion, hepatic fibrosis, lupus, liver failure after transplant, encephalomyelitis, epilepsy, and glioblastoma.

A compound described herein, when administered to a subject, may inhibit neuron degeneration. In some embodiments, inhibiting neuron degeneration may include inhibiting axon or neuron degeneration in a neuron. Such inhibition with respect to the entire neuron or a portion thereof, such as the neuron cell body, axons and dendrites. This can be assessed, for example, by analysis of neurological function according to methods known in the art. The administration of a compound described herein may result in at least a 10% decrease (e.g., at least 15%, 20%, 25%, 30%, 35%, 40%, 45%, 50%, 55%, 60%, 65%, 70%, 75%, 80%, 85%, 90%, 95%, or 100%) in the number of neurons (or neuron bodies, axons, or dendrites thereof) that degenerate in a neuron population or in a subject compared to the number of neurons (or neuron bodies, axons, or dendrites thereof) that degenerate in neuron population or in a subject that is not administered the one or more of the compounds described herein.

Neurons can convey information from tissues and organs into the central nervous system (afferent or sensory neurons) and transmit signals from the central nervous systems to effector cells (efferent or motor neurons). Other neurons, designated interneurons, connect neurons within the central nervous system (the brain and spinal column). Certain specific examples of neuron types that may be subject to treatment according to the disclosure include cerebellar granule neurons, dorsal root ganglion neurons, PNS neurons (e.g. sensory neurons), and cortical neurons. Other examples of cell types that may be subject to treatment according to the disclosure include astrocytes and microglia.

Further, the compounds described herein can be used in the prevention or treatment of memory loss. Types of memory that can be affected by loss, and thus treated according to the disclosure, include episodic memory, semantic memory, short-term memory, and long-term memory.

In some embodiments, the disease or condition is a neurodegenerative disease selected from Alzheimer's disease, amyotrophic lateral sclerosis, Huntington's disease, Parkinson's disease, Prion disease, and spinocerebellar ataxias. In some embodiments, the neurodegenerative disease is classified as a trinucleotide repeat disorder. In some embodiments, the trinucleotide repeat disorder is classified as belonging to Category I, Category II, or Category III.

In some embodiments, the pathologic process is associated with, or caused by, a disease or condition selected from Huntington's disease (HD), dentatorubral-pallidoluysian atrophy, spinal and bulbar muscular atrophy, spinocerebellar ataxia, spinal cord and/or brain injury, chronic pulmonary hypertension, Parkinson's disease, amyotrophic lateral sclerosis, cerebral cavernous malformation, cardiovascular disease, Alzheimer's disease (AD), glaucoma, multiple sclerosis (MS), corneal lesions, diabetes, chronic and/or neuropathic pain, stroke, ischemia, retinopathy, spinal muscular atrophy (SMA), erectile dysfunction, nephropathy (non-hypertensive), hypertensive nephropathy, hypertension (high blood pressure), optic nerve lesion, hepatic fibrosis, lupus, liver failure after transplant, encephalomyelitis, epilepsy, and glioblastoma. In some embodiments, the pathologic process is a neurodegenerative disease selected from Alzheimer's disease, amyotrophic lateral sclerosis, Huntington's disease, Parkinson's disease, Prion disease, and spinocerebellar ataxias. In some embodiments, the neurodegenerative disease is classified as a trinucleotide repeat disorder. In some embodiments, the trinucleotide repeat disorder is classified as belonging to Category I, Category II, or Category III.

In some embodiments, the neurodegenerative disease is Huntington's disease.

Also provided is use of a compound described herein for the manufacture of a medicament for use in diagnosis, prevention, or treatment of a disease or condition described herein. For example, the disease or condition may be Huntington's disease.

Imaging Agents and Pharmaceutical Compositions

An imaging agent will generally comprise a compound described herein labeled with a positron emitting radionuclide. Imaging agents labeled with positron emitting radionuclides are generally administered via intravenous injection shortly after (for example, within one hour of synthesis) due to the short half-life of the radionuclides. The amount of imaging agent required will normally be determined by the prescribing physician. The dose may vary according to various factors, including but not limited to the associative kinetics of the compound, the quantity of emission from the radionuclide used, the half-life of the radionuclide, the body part, body area, and/or tissue to be imaged, and the characteristics of the individual. Those of ordinary skill in the art will appreciate that an effective amount will generally be the amount of labeled compound sufficient to produce emissions in the range of from about 0.1 to about 20 mCi, or about 1 to about 5 mCi. The mass of labeled compound in an effective amount of imaging agent may be about 0.1 to about 500 mg.

Generally, a compound or an imaging agent described herein may be administered to a patient in need thereof via any suitable route. Routes of administration may include, for example, parenteral administration, including subcutaneous, intramuscular, intravenous, by means of, for example a drip patch. Further suitable routes of administration include, but are not limited to, oral, rectal, nasal, topical (including buccal and sublingual), infusion, vaginal, intradermal, intraperitoneally, intracranially, intrathecal and epidural administration or administration via oral or nasal inhalation, by means of, for example a nebulizer or inhaler, or by an implant.

With regard to PET imaging, administration of a compound or an imaging agent described herein to the individual may be intravenous. The pharmaceutical composition may be in the form of a sterile injectable aqueous or oleaginous suspension. This suspension may be formulated according to the known art using those suitable dispersing or wetting agents and suspending agents that have been mentioned above. The sterile injectable preparation may also be sterile injectable solution or suspension in a non-toxic parentally acceptable vehicle, for example as a solution in 1,3-butanediol. Among the acceptable vehicles that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid can be useful in the preparation of injectables. Such solutions may be formulated as 0.01%-10% isotonic solutions, pH 5-7, with appropriate salts.

The compound or imaging agent described herein may be administered parenterally in a sterile medium. Parenteral administration includes subcutaneous injections, intravenous, intramuscular, intrathecal injection or infusion techniques. The compound or imaging agent described herein, depending on the vehicle and concentration used, can either be suspended or dissolved in the vehicle. Advantageously, adjuvants such as local anesthetics, preservatives and buffering agents can be dissolved in the vehicle. In many pharmaceutical compositions for parenteral administration the carrier comprises at least 90% by weight of the total composition. In some embodiments, the carrier for parenteral administration is chosen from propylene glycol, ethyl oleate, pyrrolidone, ethanol, and sesame oil.

A pharmaceutical composition, for example, for injection, may comprise a cyclodextrin. The cyclodextrin may be, for example, a hydroxypropyl cyclodextrin or a sulfobutylether cyclodextrin. The cyclodextrin may be, for example, an a-cyclodextrin, a D-cyclodextrin, or a y-cyclodextrin.

A compound or an imaging agent described herein may also be administered via microspheres, liposomes, other microparticulate delivery systems or sustained release formulations placed in certain tissues including blood. Suitable examples of sustained release carriers include semi-permeable polymer matrices in the form of shared articles, e.g., suppositories or microcapsules. Examples of the techniques and protocols mentioned above and other techniques and protocols which may be used in accordance with the invention can be found in Remington's Pharmaceutical Sciences, 18th edition, Gennaro, A. R., Lippincott Williams & Wilkins; 20th edition (Dec. 15, 2000) ISBN 0-912734-04-3 and Pharmaceutical Dosage Forms and Drug Delivery Systems; Ansel, N. C. et al. 7th Edition ISBN 0-683305-72-7, the entire disclosures of which are herein incorporated by reference.

In some embodiments, the compound or imaging agent described herein is administered as a pharmaceutical composition. Accordingly, provided are pharmaceutical compositions comprising at least one compound or imaging agent described herein, together with at least one pharmaceutically acceptable vehicle chosen from carriers, adjuvants, and excipients. A compound or imaging agent of the present disclosure can be formulated into a pharmaceutical composition using techniques known to those of skill in the art.

Pharmaceutically acceptable vehicles must be of sufficiently high purity and sufficiently low toxicity to render them suitable for administration to the animal being treated. The vehicle can be inert or it can possess pharmaceutical benefits. The amount of vehicle employed in conjunction with the compound or imaging agent may be sufficient to provide a practical quantity of material for administration per dose of the compound or imaging agent.

Exemplary pharmaceutically acceptable carriers or components thereof are sugars, such as lactose, glucose and sucrose; starches, such as corn starch and potato starch; cellulose and its derivatives, such as sodium carboxymethyl cellulose, ethyl cellulose, and methyl cellulose; powdered tragacanth; malt; gelatin; talc; solid lubricants, such as stearic acid and magnesium stearate; calcium sulfate; synthetic oils; vegetable oils, such as peanut oil, cottonseed oil, sesame oil, olive oil, and corn oil; polyols such as propylene glycol, glycerine, sorbitol, mannitol, and polyethylene glycol; alginic acid; phosphate buffer solutions; emulsifiers, such as the TWEENs®; wetting agents, such sodium lauryl sulfate; coloring agents; flavoring agents; tableting agents; stabilizers; antioxidants; preservatives; pyrogen-free water; isotonic saline; and phosphate buffer solutions.

Optional active agents may be included in a pharmaceutical composition, which do not substantially interfere with the activity of the compound or imaging agent described herein.

Effective concentrations of at least one compound or imaging agent described herein are mixed with a suitable pharmaceutically acceptable vehicle. In instances in which the compound or imaging agent exhibits insufficient solubility, methods for solubilizing compounds may be used. Such methods are known to those of skill in this art, and include, but are not limited to, using cosolvents, such as dimethylsulfoxide (DMSO), using surfactants, such as TWEEN®, or dissolution in aqueous buffer, for example, sodium bicarbonate.

Upon mixing or addition of a compound or imaging agent described herein, the resulting mixture may be a solution, suspension, emulsion, or the like. The form of the resulting mixture depends upon a number of factors, including the intended mode of administration and the solubility of the compound or imaging agent in the chosen vehicle. The effective concentration sufficient for imaging or treatment may be empirically determined according to known methods in the art.

Pharmaceutical compositions may be formulated for oral use, such as for example, tablets, troches, lozenges, aqueous or oily suspensions, dispersible powders or granules, emulsions, hard or soft capsules, or syrups or elixirs. Pharmaceutical compositions intended for oral use may be prepared according to any method known to the art for the manufacture of pharmaceutical compositions and such compositions may contain one or more agents, such as sweetening agents, flavoring agents, coloring agents and preserving agents, in order to provide pharmaceutically elegant and palatable preparations. In some embodiments, oral pharmaceutical compositions contain from 0.1 to 99% of the compound or imaging agent described herein. In some embodiments, oral pharmaceutical compositions contain at least 5% (weight %) of the compound or imaging agent. Some embodiments contain from 25% to 50% or from 5% to 75% of the compound or imaging agent.

Orally administered pharmaceutical compositions also include liquid solutions, emulsions, suspensions, powders, granules, elixirs, tinctures, syrups, and the like. The pharmaceutically acceptable carriers suitable for preparation of such compositions are well known in the art. Oral pharmaceutical compositions may contain preservatives, flavoring agents, sweetening agents, such as sucrose or saccharin, taste-masking agents, and coloring agents.

Typical components of carriers for syrups, elixirs, emulsions and suspensions include ethanol, glycerol, propylene glycol, polyethylene glycol, liquid sucrose, sorbitol and water. Syrups and elixirs may be formulated with sweetening agents, for example glycerol, propylene glycol, sorbitol or sucrose. Such pharmaceutical compositions may also contain a demulcent.

The compound or imaging agent described herein can be incorporated into oral liquid preparations such as aqueous or oily suspensions, solutions, emulsions, syrups, or elixirs, for example. Furthermore, pharmaceutical compositions containing the compound or imaging agent described herein can be presented as a dry product for constitution with water or other suitable vehicle before use. Such liquid preparations can contain conventional additives, such as suspending agents (e.g., sorbitol syrup, methyl cellulose, glucose/sugar, syrup, gelatin, hydroxyethyl cellulose, carboxymethyl cellulose, aluminum stearate gel, and hydrogenated edible fats), emulsifying agents (e.g., lecithin, sorbitan monooleate, or acacia), non-aqueous vehicles, which can include edible oils (e.g., almond oil, fractionated coconut oil, silyl esters, propylene glycol and ethyl alcohol), and preservatives (e.g., methyl or propyl p-hydroxybenzoate and sorbic acid).

For a suspension, typical suspending agents include methylcellulose, sodium carboxymethyl cellulose, Avicel® RC-591, tragacanth and sodium alginate; typical wetting agents include lecithin and polysorbate 80; and typical preservatives include methyl paraben and sodium benzoate.

Aqueous suspensions containing the compound or imaging agent in admixture with excipients suitable for the manufacture of aqueous suspensions are provided. Such excipients are suspending agents, for example sodium carboxymethylcellulose, methylcellulose, hydropropylmethylcellulose, sodium alginate, polyvinylpyrrolidone, gum tragacanth and gum acacia; dispersing or wetting agents; may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol substitute, or condensation products of ethylene oxide with partial esters derived from fatty acids and hexitol anhydrides, for example polyethylene sorbitan substitute. The aqueous suspensions may also contain one or more preservatives, for example ethyl, or n-propyl p-hydroxybenzoate.

Oily suspensions may be formulated by suspending the compound or imaging agent in a vegetable oil, for example peanut oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide palatable oral preparations. These pharmaceutical compositions may be preserved by the addition of an anti-oxidant such as ascorbic acid.

Pharmaceutical compositions may also be in the form of an oil-in-water emulsion. The oily phase may be a vegetable oil (for example, olive oil or peanut oil) or a mineral oil (for example, liquid paraffin) or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monooleate, and condensation products of the said partial esters with ethylene oxide, for example polyoxyethylene sorbitan monooleate.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above.

Tablets typically comprise conventional pharmaceutically acceptable adjuvants as inert diluents, such as calcium carbonate, sodium carbonate, mannitol, lactose and cellulose; binders such as starch, gelatin and sucrose; disintegrants such as starch, alginic acid and croscarmellose; lubricants such as magnesium stearate, stearic acid and talc. Glidants such as silicon dioxide can be used to improve flow characteristics of the powder mixture. Coloring agents, such as the FD&C dyes, can be added for appearance. Sweeteners and flavoring agents, such as aspartame, saccharin, menthol, peppermint, and fruit flavors, can be useful adjuvants for chewable tablets. Capsules (including time release and sustained release formulations) typically comprise one or more solid diluents disclosed above. The selection of carrier components often depends on secondary considerations like taste, cost, and shelf stability.

The pharmaceutical composition may also be coated by conventional methods, typically with pH or time-dependent coatings, such that the compound or imaging agent is released in the gastrointestinal tract in the vicinity of the desired topical application, or at various times to extend the desired action. Such dosage forms typically include, but are not limited to, one or more of cellulose acetate phthalate, polyvinylacetate phthalate, hydroxypropyl methylcellulose phthalate, ethyl cellulose, Eudragit® coatings, waxes and shellac.

Pharmaceutical compositions for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

The compound or imaging agent described herein may also be administered in the form of suppositories for rectal administration of the drug. These pharmaceutical compositions can be prepared by mixing the drug with a suitable non-irritating excipient that is solid at ordinary temperatures but liquid at rectal temperature and will therefore melt in the rectum to release the drug. Such materials include cocoa butter and polyethylene glycols.

The compound or imaging agent described herein may be formulated for local or topical application, such as for topical application to the skin and mucous membranes, such as in the eye, in the form of gels, creams, and lotions and for application to the eye. Topical pharmaceutical compositions may be in any form including, for example, solutions, creams, ointments, gels, lotions, milks, cleansers, moisturizers, sprays, skin patches, and the like.

Topical pharmaceutical compositions comprising at least one compound, or an isotopically labeled analog, pharmaceutically acceptable salt, solvate, prodrug, stereoisomer, or mixture of stereoisomers thereof, described herein can be admixed with a variety of carrier materials well known in the art, such as, for example, water, alcohols, aloe vera gel, allantoin, glycerine, vitamin A and E oils, mineral oil, propylene glycol, PPG-2 myristyl propionate, and the like.

Other materials suitable for use in topical carriers include, for example, emollients, solvents, humectants, thickeners and powders. Examples of each of these types of materials, which can be used singly or as mixtures of one or more materials, are as follows.

Representative emollients include stearyl alcohol, glyceryl monoricinoleate, glyceryl monostearate, propane-1,2-diol, butane-1,3-diol, mink oil, cetyl alcohol, iso-propyl isostearate, stearic acid, iso-butyl palmitate, isocetyl stearate, oleyl alcohol, isopropyl laurate, hexyl laurate, decyl oleate, octadecan-2-ol, isocetyl alcohol, cetyl palmitate, dimethylpolysiloxane, di-n-butyl sebacate, iso-propyl myristate, iso-propyl palmitate, iso-propyl stearate, butyl stearate, polyethylene glycol, triethylene glycol, lanolin, sesame oil, coconut oil, arachis oil, castor oil, acetylated lanolin alcohols, petroleum, mineral oil, butyl myristate, isostearic acid, palmitic acid, isopropyl linoleate, lauryl lactate, myristyl lactate, decyl oleate, and myristyl myristate; propellants, such as propane, butane, iso-butane, dimethyl ether, carbon dioxide, and nitrous oxide; solvents, such as ethyl alcohol, methylene chloride, iso-propanol, castor oil, ethylene glycol monoethyl ether, diethylene glycol monobutyl ether, diethylene glycol monoethyl ether, dimethyl sulfoxide, dimethyl formamide, tetrahydrofuran; humectants, such as glycerin, sorbitol, sodium 2-pyrrolidone-5-carboxylate, soluble collagen, dibutyl phthalate, and gelatin; and powders, such as chalk, talc, fullers earth, kaolin, starch, gums, colloidal silicon dioxide, sodium polyacrylate, tetra alkyl ammonium smectites, trialkyl aryl ammonium smectites, chemically modified magnesium aluminum silicate, organically modified montmorillonite clay, hydrated aluminum silicate, fumed silica, carboxyvinyl polymer, sodium carboxymethyl cellulose, and ethylene glycol monostearate.

The compound or imaging agent described herein may also be formulated for transdermal administration as a transdermal patch.

The compound or imaging agent described herein may also be administered in a liposome delivery system. Liposomes may be classified as small unilamellar vesicles, large unilamellar vesicles, and multilamellar vesicles. Liposomes can be formed from a variety of amphipathic molecules, in particular phospholipids. Constituents of liposomes may include cholesterol, stearylamine and/or phosphatidylcholines. Liposomes are suitable for various routes of administration including topical and injection into various tissues. Thus, intravitreal (e.g., in treatment of glaucoma), intraperitoneal, intravenous, intravascular, intraarticular, and intramuscular administration of liposomes is contemplated.

Other pharmaceutical compositions useful for attaining systemic delivery of the compound or imaging agent include sublingual, buccal and nasal dosage forms. Such pharmaceutical compositions typically comprise one or more of soluble filler substances such as sucrose, sorbitol and mannitol, and binders such as acacia, microcrystalline cellulose, carboxymethyl cellulose, and hydroxypropyl methylcellulose. Glidants, lubricants, sweeteners, colorants, antioxidants and flavoring agents disclosed above may also be included.

Pharmaceutical compositions for inhalation typically can be provided in the form of a solution, suspension or emulsion that can be administered as a dry powder or in the form of an aerosol using a conventional propellant (e.g., dichlorodifluoromethane or trichlorofluoromethane).

The pharmaceutical compositions may also optionally comprise an activity enhancer. The activity enhancer can be chosen from a wide variety of molecules that function in different ways to enhance or be independent of therapeutic effects of the compound or imaging agent described herein. Particular classes of activity enhancers include skin penetration enhancers and absorption enhancers.

Pharmaceutical compositions may also contain additional active agents that can be chosen from a wide variety of molecules, which can function in different ways to enhance the therapeutic effects of the compound or imaging agent described herein. These optional other active agents, when present, are typically employed in the pharmaceutical compositions at a level ranging from 0.01% to 15%. Some embodiments contain from 0.1% to 10% by weight of the composition. Other embodiments contain from 0.5% to 5% by weight of the composition.

The dose of the compound or imaging agent described herein depends upon a variety of factors including the particular pathologic process to be treated or detected, the physiology of the individual, the severity of the symptoms, the route of administration, the frequency of the dosage interval, the particular compound utilized, the efficacy, toxicology profile, pharmacokinetic profile of the compound, and the presence of any deleterious side-effects, among other considerations. The dose under a given set of circumstances generally will be determined by a practitioner on a case-by-case basis based on the above and other factors.

The compound or imaging agent described herein is typically administered at a dosage level and in a manner determined by a practitioner such as a physician. For example, the compound or imaging agent can be administered, in single or multiple doses, at a dosage level of generally 0.001-100 mg/kg, for example, 0.01-100 mg/kg, such as 0.1-70 mg/kg, for example, 0.5-10 mg/kg. The dose can be, for example, for administration once a day or twice a day. Unit dosage forms can contain generally 0.01-1000 mg of the compound or imaging agent described herein, for example, 0.1-50 mg. For intravenous administration, the compound or imaging agent can be administered, in single or multiple dosages, at a dosage level of, for example, 0.001-50 mg/kg, such as 0.001-10 mg/kg, for example, 0.01-1 mg/kg. Unit dosage forms can contain, for example, 0.1-10 mg of the compound or imaging agent.

Kits and Packaging

Also provided herein are kits that include a compound described herein and suitable packaging. In certain embodiments, a kit further includes instructions for use. In some embodiments, a kit includes a compound or an imaging agent described herein and a label and/or instructions for use of the compounds in the treatment of the indications, including the diseases or conditions, described herein.

Also provided herein are articles of manufacture that include a compound or an imaging agent described herein in a suitable container. The container may be a vial, jar, ampoule, preloaded syringe and intravenous bag.

Also provided are packaged pharmaceutical compositions. Such packaged compositions include a pharmaceutical composition comprising a compound or imaging agent described herein, and instructions for using the composition to treat a subject (typically a human patient). In some embodiments, the instructions are for using the pharmaceutical composition to detect a disease or condition described herein. The packaged pharmaceutical composition can include prescribing information; for example, to a patient or health care provider, or as a label in a packaged pharmaceutical composition. Prescribing information may include for example efficacy, dosage and administration, contraindication and adverse reaction information pertaining to the pharmaceutical composition.

In all of the foregoing the compound or imaging agent can be administered alone, as mixtures, or in combination with other active agents.

Also provided is use of a compound or imaging agent described herein for the manufacture of a medicament for use in diagnosis, prevention, or treatment of a disease or condition described herein. For example, the disease or condition may be Huntington's disease.

Also provided is use of a compound described herein for the manufacture of an imaging agent for use in diagnosis, prevention, or treatment of a disease or condition described herein. For example, the disease or condition may be Huntington's disease.

Combination Therapy

The methods described herein include methods for detecting, treating or preventing a disease or condition described herein, comprising administering to a subject, simultaneously or sequentially, a compound or imaging agent described herein and one or more additional active agents. For example, the disease or condition may be Huntington's disease. In methods using simultaneous administration, the agents can be present in a combined composition or can be administered separately. When used in combination with one or more additional active agent or agents, a compound or imaging agent described herein may be administered prior to, concurrently with, or following administration of the additional active agent or agents. The administration can be by the same route or by different routes.

Also provided is a pharmaceutical composition comprising a compound or imaging agent described herein and one or more additional active agents used in the treatment of Huntington's disease such as, but not limited to, carbamazepine, clonazepam, diazepam, fluoxetine, escitalopram, valproate, lamotrigine, amitriptyline, imipramine, desipramine, nortriptyline, paroxetine, fluoxetine, sertraline, tetrabenazine, haloperidol, chlorpromazine, thioridazine, sulpiride, quetiapine, clozapine, and risperidone. Similarly, also provided is a packaged pharmaceutical composition containing a pharmaceutical composition comprising a compound or imaging agent described herein, and another composition comprising one or more additional active agents used in the treatment of Huntington's disease such as, but not limited to, carbamazepine, clonazepam, diazepam, fluoxetine, escitalopram, valproate, lamotrigine, amitriptyline, imipramine, desipramine, nortriptyline, paroxetine, fluoxetine, sertraline, tetrabenazine, haloperidol, chlorpromazine, thioridazine, sulpiride, quetiapine, clozapine, and risperidone. In some embodiments, the active agent is carbamazepine, clonazepam, diazepam, fluoxetine, escitalopram, valproate, lamotrigine, amitriptyline, imipramine, desipramine, nortriptyline, paroxetine, fluoxetine, sertraline, tetrabenazine, haloperidol, chlorpromazine, thioridazine, sulpiride, quetiapine, clozapine, or risperidone.

Also provided are methods for treating or preventing Alzheimer's disease, including treating memory and/or cognitive impairment associated with Alzheimer's disease, comprising administering to a subject, simultaneously or sequentially, a compound or imaging agent described herein and one or more additional agents. In some embodiments, the active agent is Reminyl®, Cognex®, Aricept®, Exelon®, Akatinol®, Neotropin™, Eldepryl®, Estrogen or Clioquinol.

In some embodiments, compounds described herein can be administered with an active agent for treating Parkinson's disease, for example, with L-dopa, dopamine agonists (e.g., bromocriptine, pergolide, pramipexole, ropinirole, cabergoline, apomorphine, and lisuride), dopa decarboxylase inhibitors (e.g., levodopa, benserazide, and carbidopa), and/or MAO-B inhibitors (e.g., selegiline and rasagiline). In some embodiments, compounds described herein can be administered with an active agent for treating Alzheimer's disease, for example, with acetylcholinesterase inhibitors (e.g., donepezil, galantamine, and rivastigmine) and/or NMDA receptor antagonists (e.g., memantine).

Synthesis of the Compounds

A compound described herein may be prepared using the methods disclosed herein and routine modifications thereof, which will be apparent given the disclosure herein and methods well known in the art. Conventional and well-known synthetic methods may be used in addition to the teachings herein. The synthesis of a typical compound described herein may be accomplished as described in the following examples. If available, reagents may be purchased commercially, e.g., from Sigma Aldrich or other chemical suppliers.

A compound described herein can be prepared from readily available starting materials using, for example, the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in Wuts, P. G. M., Greene, T. W., & Greene, T. W. (2006), Greene's protective groups in organic synthesis. Hoboken, N.J., Wiley-Interscience, and references cited therein.

Furthermore, a compound described herein may contain one or more asymmetric ("chiral") centers. Accordingly, if desired, such compounds can be prepared or isolated as pure stereoisomers, i.e., as individual enantiomers or diastereomers or as stereoisomer-enriched mixtures. All such stereoisomers (and enriched mixtures) are included within the scope of this disclosure, unless otherwise indicated. Pure stereoisomers (or enriched mixtures) may be prepared using, for example, optically active starting materials or stereoselective reagents well-known in the art. Alternatively, racemic mixtures of such compounds can be separated using, for example, chiral column chromatography, supercritical fluid chromatography, chiral resolving agents, and the like. When enantiomerically pure or enriched compounds are desired, chiral chromatography and/or enantiomerically pure or enriched starting materials may be employed as conventionally used in the art or as described in the Examples.

The starting materials for the following reactions are generally known compounds or can be prepared by known procedures or obvious modifications thereof. For example, many of the starting materials are available from commercial suppliers such as Sigma Aldrich, Alfa Aesar, and the like. Others may be prepared by procedures or obvious modifications thereof, described in standard reference texts such as Fieser and Fieser's Reagents for Organic Synthesis, Volumes 1-15 (John Wiley, and Sons, 1991), Rodd's Chemistry of Carbon Compounds, Volumes 1-5, and Supplementals (Elsevier Science Publishers, 1989) organic Reactions, Volumes 1-40 (John Wiley, and Sons, 1991), March's Advanced Organic Chemistry, (John Wiley, and Sons, 5th Edition, 2001), and Larock's Comprehensive Organic Transformations (VCH Publishers Inc., 1989).

The terms "solvent," "inert organic solvent" and "inert solvent" refer to a solvent inert under the conditions of the reaction being described in conjunction therewith (including, for example, benzene, toluene, acetonitrile, tetrahydrofuran ("THF"), dimethylformamide ("DMF"), chloroform, methylene chloride (or dichloromethane), diethyl ether, methanol, pyridine and the like). Generally, the term inert, as used herein with respect to a solvent, refers to a material that does not undergo reaction to form the target compound of interest through carbon-carbon bond forming reactions. Unless specified to the contrary, the solvents used in the reactions of the present disclosure are inert organic solvents, and the reactions are carried out under an inert gas, preferably nitrogen or argon.

The term "q.s." means adding a quantity sufficient to achieve a stated function, e.g., to bring a solution to the desired volume (i.e., 100%).

It will also be appreciated that in each of the schemes below, the addition of any substituent may result in the production of a number of isomeric products (including, but not limited to, enantiomers or one or more diastereomers) any or all of which may be isolated and purified using conventional techniques.

Incorporation of a label into a compound or imaging agent described herein may be conducted by reacting an appropriate starting material(s) with a reagent including a positron-emitting isotope. Methods typically follow the same principles as standard organic chemical reactions, and may be carried out by any method known to those of skill in the art, including those provided in the present disclosure.

Schemes 1 and 2 provide exemplary synthetic routes for the synthesis of compounds provided herein (e.g., compounds of Formula I). The compounds of Formula I, or other formulas or compounds disclosed herein, are typically prepared from, e.g., Compound 1 and Compound 6, and by attaching the desired substituents using suitable conditions (e.g., nucleophilic addition or cross coupling).

In some embodiments, synthesis of a compound described herein begins according to Scheme 1.

Scheme 1

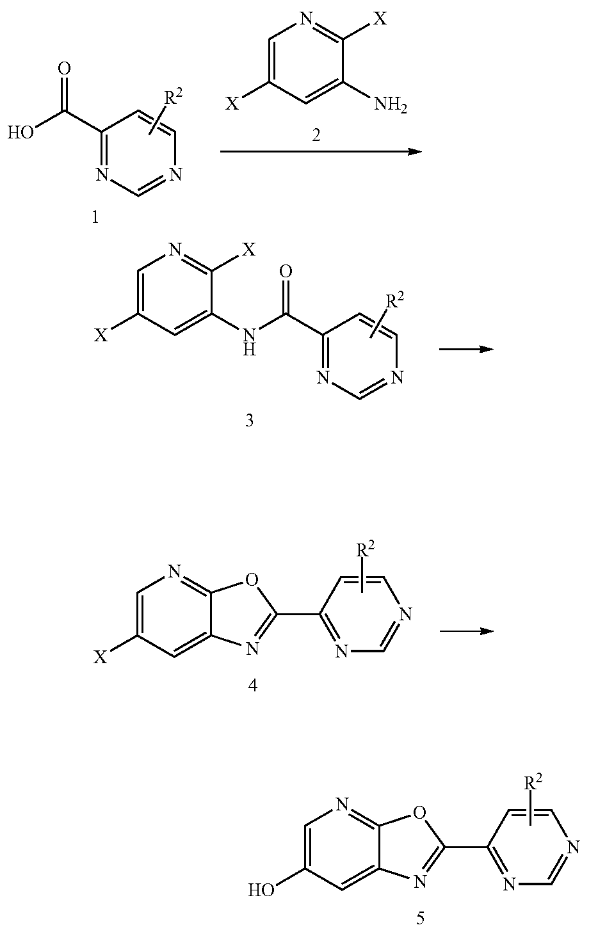

1
2
3
4
5

In Scheme 1, $R^2$ is as defined herein, and X is a halogen, such as bromo, chloro, or iodo. In Scheme 1, pyrimidine-4-carboxylic acid 1 undergoes an amide bond formation with pyridine amine compound 2 in the presence of peptide coupling reagent, such as EDC·HCl, HOBt, HATU, and the like, and a suitable base, such as pyridine and the like, to provide compounds of formula 3. Alternatively, pyrimidine-4-carboxylic acid 1 can be converted to the corresponding pyrimidine acyl halide by contacting 1 with a halogenating agent, including, but not limited to, phosphorus (V) oxychloride, oxalyl chloride, and the like, and then reacted directly with pyridine amine compound 2 to provide for compounds of formula 3. Compound 3 is then cyclized by treating with a base, such as sodium carbonate and the like, under microwave irradiation to provide oxazolopyridine compound 4. The remaining halide on oxazolopyridine compound 4 can be converted to a hydroxyl group via a Miyaura borylation (e.g., in the presence of a palladium-based reagent, such as $PdCl_2$(dppf) or any other suitable reagent, bis(pinacolato)diboron, and a suitable base, such as potassium acetate and the like), followed by an oxidation of the intermediate boronate ester with sodium perborate tetrahydrate or any other suitable reagent, to provide for compounds of formula 5.

In some embodiments, synthesis of a compound described herein may be carried out according to Scheme 2.

Scheme 2

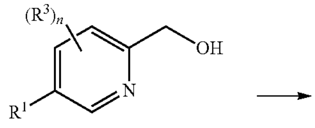

6

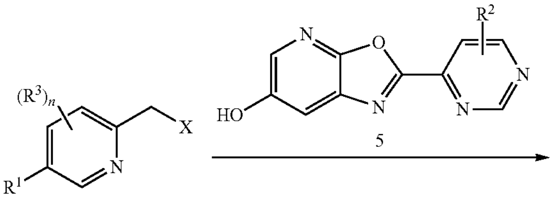

5

7

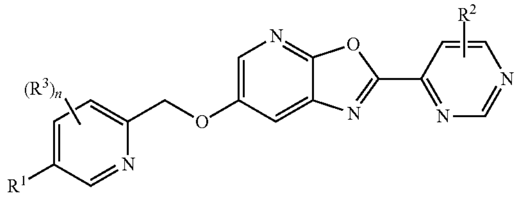

Formula I, Ia, or Ib

In Scheme 2, $R^1$, $R^2$, $R^3$, and n are as defined herein, and X is a halogen, such as bromo, chloro, or iodo. In Scheme 2, the primary alcohol of pyridine compounds of formula 6 is converted to a halide by treatment with thionyl chloride and the like to provide for compounds of formula 7. Compounds of Formula I, Ia, or Ib can be accessed via an $S_N2$ reaction between oxazolopyridine compound 5 and pyridine compound 7, in the presence of a suitable base, such as potassium carbonate and the like. Alternatively, pyridine compound 6 can be reacted directly with oxazolopyridine compound 5 under suitable Mitsunobu reaction conditions (e.g., in the presence of cyanomethyltributylphosphorane, triphenylphosphine and an azodicarboxylate, or any other suitable reagent) to provide for compounds of Formula I, La, or Ib.

Synthesis of compounds described herein may also be carried out by the method described herein or by methods known in the art, for example, those described in International Publication No. WO 2016/033445.

Synthesis of compounds of Formula I, Ia, or Ib described herein that carry a $^{18}F$-radionuclide, including but not limited to compound 9, may be prepared according to Scheme 3.

Scheme 3

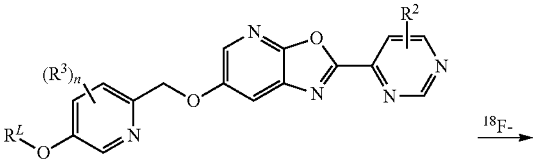

8

-continued

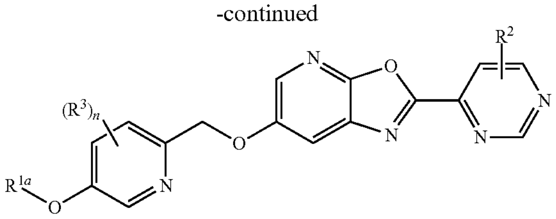

9

In Scheme 3, $R^2$, $R^3$, and n are as defined herein; $R^L$ is $C_{1-6}$alkyl, $C_{1-6}$haloalkyl, or deuterated $C_{1-6}$haloalkyl substituted with one leaving group (such as mesylate, tosylate, or triflate); and $R^{1a}$ of compound 9 is $C_{1-6}$haloalkyl or deuterated $C_{1-6}$haloalkyl, wherein at least one halo of $R^{1a}$ is $^{18}F$. In Scheme 3, the $^{18}F$ anion generated from a cyclotron is reacted with compound 8 in the presence of a base (such as potassium carbonate, 2-(tert-butyl)-1,1,3,3-tetramethylguanidine and the like) under phase transfer conditions (for example, K2,2,2 and the like) to give compound 9 under standard conditions.

A person of skill in the art will appreciate that any of the compounds described herein may be prepared from starting materials obtained from a commercial supplier. Alternatively, syntheses of compounds described herein may be as described herein or as known to those of skill in the art.

EXAMPLES

The following examples are included to demonstrate specific embodiments of the disclosure. It should be appreciated by those of skill in the art that the techniques disclosed in the examples which follow represent techniques to function well in the practice of the disclosure, and thus can be considered to constitute specific modes for its practice. However, those of skill in the art should, in light of the present disclosure, appreciate that many changes can be made in the specific embodiments which are disclosed and still obtain a like or similar result without departing from the spirit and scope of the disclosure.

1. General Experimental Procedures

Commercially available reagents and solvents (HPLC grade) were used without further purification. $^1H$ NMR spectra were recorded on a Bruker DRX 500 MHz spectrometer or Bruker DPX 250 MHz spectrometer or a Bruker AVANCE 300 or on a Bruker AVANCE 500 spectrometer in deuterated solvents.

Chemical shifts (S) are in parts per million. Flash column chromatography refers to automated purification on Biotage Isolera systems using an appropriately sized SNAP or KPNH pre-packed silica columns and the solvents recorded in the experimental section; or on Isco Combiflash Rf systems using appropriately sized pre-packed silica columns and the solvents recorded in the experimental section. Reverse phase MPLC chromatography was performed on Isco Combiflash Rf systems using appropriately sized pre-packed C18 columns and the solvents recorded in the experimental section Thin-layer chromatography (TLC) analysis was performed with Kieselgel 60 F254 (Merck) plates and visualized using UV light. SCX chromatography was performed with Biotage Isolute Flash SCX-2 loading the sample in methanol and eluting with methanol then 5% ammonia in methanol.

2. Analytical Methods

Acidic-Phase HPLC Methods

Alternatively, HPLC-MS (METCR1410) was performed on Shimadzu LCMS-2010EV systems using a reverse phase Kinetix Core-Shell C18 column (5 μm, 2.1×50 mm) at a column temp of 40° C., gradient 5-100% B (A=water/0.1% formic acid, B=acetonitrile/0.1% formic acid) over 1.2 min, then 100% B over 0.1 min, injection volume 3 μL, flow=1.2 mL/min. All other aspects of the method were unchanged.

Alternatively, (MET-uHPLC-AB-101) analytical HPLC-MS were performed on a Waters Acquity UPLC system with Waters PDA and ELS detectors using a Phenomenex Kinetex-XB C-18 column, (1.7 μm, 2.1 mm×100 mm at a column temp of 40° C., gradient 5-100% B (A=water/0.1% formic acid; B=acetonitrile/0.1% formic acid) over 5.3 min, then 100% B for 0.5 min, flow=0.6 mL/min. UV spectra were recorded at 215 nm using a Waters Acquity PDA detector. Mass spectra were obtained over the range m/z 150 to 850 at a sampling rate of 2 scans per second using a Waters ZQ. Data were integrated and reported using OpenLynx software.

Alternatively, UHPLC (METAMRI001) was performed on a Waters Acquity H-Class system using an Acquity UPLC BEH C18 column (1.7 m, 2.1×75 mm), gradient 5-100% B (A=water/0.1% trifluoroacetic acid, B=acetonitrile/0.1% trifluoroacetic acid) at an ambient column temp (approx. 22° C.) over 6.0 min then 100% B for 2.0 min, flow=0.5 mL/min. UV spectra were recorded at 254 and 215 nm.

Alternatively, UHPLC (METAMRI002) was performed on a Waters Acquity H-Class system using an Acquity UPLC BEH C18 column (1.7 μm, 2.1×75 mm), gradient 5-100% B (A=water/0.1% trifluoroacetic acid, B=acetonitrile/0.1% trifluoroacetic acid) at an ambient column temp (approx. 22° C.) over 6.0 min then 100% B for 2.0 min, flow=0.4 mL/min. UV spectra were recorded at 254 and 215 nm.

Alternatively, mass spectra and LCMS analyses were obtained using a Waters Acquity SQD (ESI, UP-LCMS) system or an Agilent G6100A SQ LCMS system. All example compounds display an LC purity of >95% unless stated otherwise.

Basic-Phase HPLC Methods

Analytical HPLC-MS (METCR1600), was performed on Hewlett Packard HPLC systems using reverse phase Phenomenex Gemini C18 columns (3 μm, 2.0×100 mm), gradient 5-100% B (A=2 mM ammonium bicarbonate in water buffered to pH 10, B=acetonitrile) over 5.5 min then 100% B for 0.4 min, injection volume 3 μL, flow=0.5 mL/minute. UV spectra were recorded at 215 nm using a Waters PDA detector. Mass spectra were obtained over the range m/z 150 to 850 at a sampling rate of 2 scans per second using a Waters ZQ. Data were integrated and reported using OpenLynx software.

All example compounds display an LC purity of >95% unless stated otherwise.

Preparative HPLC Methods

Preparative HPLC separations were performed on a Varian Prep HPLC system using Varian SD-1 preparative LC pumps and ProStar 325 UV/Vis Detector. An XBridge Prep C18 OBD column (5 μm, 19×250 mm) was used, eluted according to solvent gradient Method 2.

Method 2

| Time (min) | Flow (mL/min) | % A | % B |
|---|---|---|---|
| 0.0 | 5 | 95 | 5 |
| 0.5 | 5 | 95 | 5 |

-continued

Method 2

| Time (min) | Flow (mL/min) | % A | % B |
|---|---|---|---|
| 1.0 | 20 | 95 | 5 |
| 4.0 | 20 | 95 | 5 |
| 44.0 | 20 | 0 | 100 |

A = Water with v/v 0.1% formic acid
B = Acetonitrile

Intermediates

Intermediate 1: (5-(Allyloxy)pyridin-2-yl)methanol

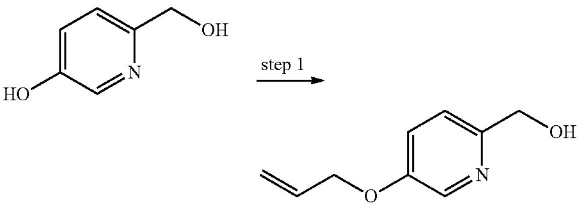

Step 1: (5-(Allyloxy)pyridin-2-yl)methanol

A solution of 6-(hydroxymethyl)pyridin-3-ol (100 mg, 0.799 mmol) and allyl bromide (0.080 mL, 0.92 mmol) in acetone (3.0 mL) was treated with a solution of potassium carbonate (166 mg, 1.19 mmol) in water (3.0 mL), dropwise, then the solution was heated at 60° C. for 2 h. After this time, the solution was cooled to rt and extracted with MTBE (3×40 mL). The combined organic layers were dried over sodium sulfate, filtered, and the filtrate was concentrated in vacuo to give the title compound. H NMR (300 MHz, $CDCl_3$) 8.27 (d, J=2.4 Hz, 1H), 7.25-7.16 (m, 2H), 6.11-5.98 (m, 1H), 5.47-5.45 (m, 1H), 5.41-5.30 (m, 1H), 4.70 (s, 2H), 4.61-4.58 (m, 2H), 3.39 (br s, 1H).

Intermediate 2: (5-(Fluoromethoxy)pyridin-2-yl)methanol

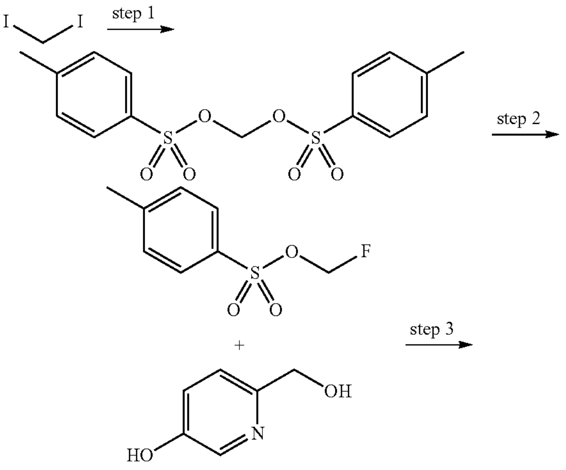

-continued

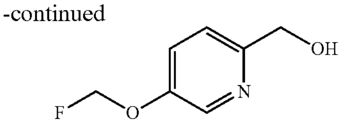

Step 1: Methylene bis(4-methylbenzenesulfonate)

A mixture of silver p-toluenesulfonate (11.5 g, 41.1 mmol) and MeCN (43.4 mL) was treated with diiodomethane (5.00 g, 18.7 mmol), and the mixture was stirred at reflux for 16 h. After this time, the mixture was cooled to rt, filtered, and the filter cake washed with MeCN (3×20 mL). The filtrate was concentrated in vacuo. DCM (40 mL) was added to the residue, the suspension was filtered, and the filter cake was washed with DCM (3×20 mL). The filtrate was concentrated in vacuo, and the residue obtained was recrystallized from EtOH (30 mL). The isolated product was dried in vacuo to afford the title compound. $^1$H NMR (300 MHz, $CDCl_3$) 7.59 (d, J=8.4 Hz, 4H), 7.25 (d, J=8.7 Hz, 4H), 5.81 (s, 2H), 2.45 (s, 6H).

Step 2: Fluoromethyl 4-methylbenzenesulfonate

A mixture of methylene bis(4-methylbenzenesulfonate) (4.09 g, 11.5 mmol) and MeCN (26.7 mL) was treated with 1 M TBAF in THF (12.6 mL, 12.6 mmol), and the mixture was stirred at reflux for 2 h. After this time, the solvent was removed in vacuo, and the residue obtained was dissolved in EtOAc (40 mL). The solution was washed with brine (40 mL), dried over sodium sulfate, filtered, and concentrated in vacuo. The residue obtained was purified by FCC (silica, 0-50% EtOAc in heptane) to afford the title compound. $^1$H NMR (300 MHz, $CDCl_3$) 7.84 (d, J=8.4 Hz, 2H), 7.36 (d, J=8.1 Hz, 2H), 5.74 (d, J=51.0 Hz, 2H), 2.64 (s, 3H).

Step 3: (5-(Fluoromethoxy)pyridin-2-yl)methanol

A mixture of 6-(hydroxymethyl)pyridin-3-ol (300 mg, 2.40 mmol), fluoromethyl 4-methylbenzenesulfonate (588 mg, 2.88 mmol) and acetone (9.0 mL) was treated with potassium carbonate (994 mg, 7.19 mmol), and the mixture was heated at 70° C. for 16 h. After this time, the mixture was cooled to rt and extracted with DCM (3×40 mL). The combined organic layers were dried over sodium sulfate, filtered, and the filtrate was concentrated in vacuo. The residue obtained was purified by FCC (silica, 0-5% MeOH in DCM) to afford the title compound. $^1$H NMR (300 MHz, DMSO-$d_6$) 8.32 (d, J=3.0 Hz, 1H), 7.58 (dd, J=8.7, 2.7 Hz, 1H), 7.46 (d, J=8.7 Hz, 1H), 5.90 (d, J=54.0 Hz, 2H), 5.41 (t, J=5.7 Hz, 1H), 4.52 (d, J=5.7 Hz, 2H).

Intermediate 3: 2-((6-(Chloromethyl)pyridin-3-yl)oxy)ethyl 4-methylbenzenesulfonate

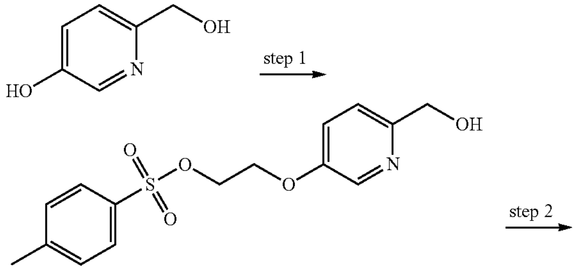

-continued

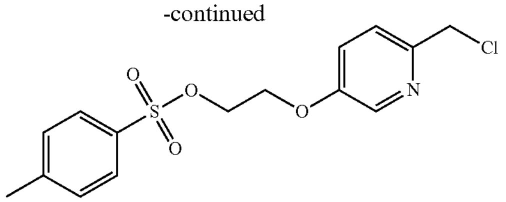

Step 1: 2-((6-(Hydroxymethyl)pyridin-3-yl)oxy) ethyl 4-methylbenzenesulfonate

Ethylene di(p-toluenesulfonate) (3.55 g, 9.59 mmol) was added to a mixture of 6-(hydroxymethyl)pyridin-3-ol (400 mg, 3.20 mmol) and cesium carbonate (3.12 g, 9.59 mmol) in MeCN (40 mL), and the mixture was stirred at 80° C. for 2.5 h. After this time, the reaction mixture was cooled, filtered through diatomaceous earth, and the filter cake was washed with EtOAc (2×50 mL). The filtrate was concentrated in vacuo, and the residue obtained was purified by FCC (silica, 0-10% MeOH in DCM) to give the title compound. $^1$H NMR (300 MHz, $CDCl_3$) 8.13-8.12 (m, 1H), 7.82 (d, J=8.1 Hz, 2H), 7.35 (d, J=7.8 Hz, 2H), 7.16-7.14 (m, 2H), 4.70 (s, 2H), 4.41-4.38 (m, 2H), 4.22-4.19 (m, 2H), 3.33 (br s, 1H), 2.46 (s, 3H).

Step 2: 2-((6-(Chloromethyl)pyridin-3-yl)oxy)ethyl 4-methylbenzenesulfonate

Thionyl chloride (0.208 mL, 2.85 mmol) was added to a solution of 2-((6-(hydroxy-methyl)pyridin-3-yl)oxy)ethyl 4-methylbenzenesulfonate (460 mg, 1.42 mmol) in DCM (9.9 mL) at 0° C., and the solution was stirred at 0° C. for 1 h. After this time, the reaction mixture was poured into water (25 mL) and extracted with DCM (2×25 mL). The combined organic layers were dried over sodium sulfate, filtered, and concentrated in vacuo to give the title compound. $^1$H NMR (300 MHz, $CDCl_3$) 8.13 (d, J=3.0 Hz, 1H), 7.81 (d, J=8.4 Hz, 2H), 7.37-7.34 (m, 3H), 7.12 (dd, J=8.7, 3.0 Hz, 1H), 4.63 (s, 2H), 4.41-4.38 (m, 2H), 4.22-4.19 (m, 2H), 2.46 (s, 3H).

Intermediate 4: 2-(Chloromethyl)-3-fluoro-5-methoxypyridine

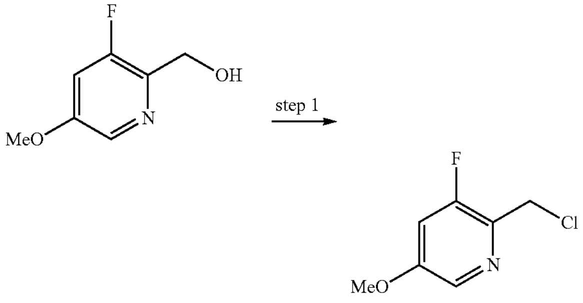

Step 1: 2-(Chloromethyl)-3-fluoro-5-methoxypyridine

Thionyl chloride (0.065 mL, 0.89 mmol) was added to a mixture of (3-fluoro-5-methoxy-pyridin-2-yl)methanol (70 mg, 0.45 mmol) in DCM (3.1 mL), and the mixture was stirred at rt for 20 min. After this time, the mixture was poured into water (25 mL) and extracted with DCM (2×25 mL). The combined organic layers were dried over sodium sulfate, filtered, and concentrated in vacuo to give the title compound which was used without purification.

Method 1

Scheme for Method 1

Scheme for Method 1

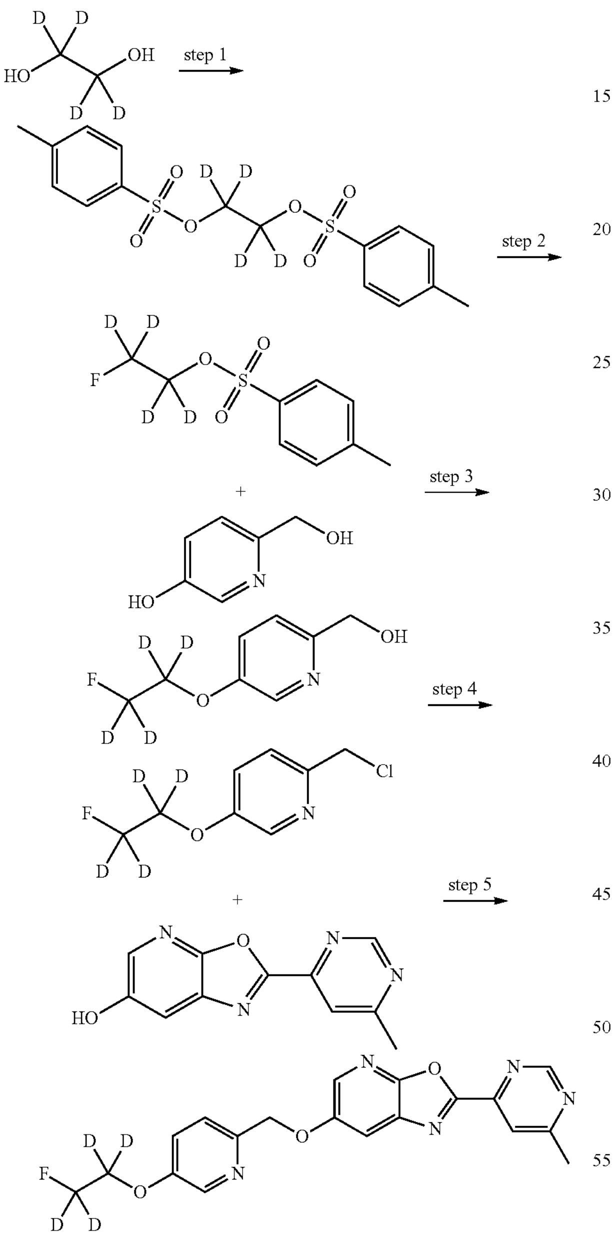

Example 1-1

Step 1: Ethane-1,2-diyl-$d_4$ bis(4-methylbenzenesulfonate)

p-Toluenesulfonyl chloride (5.77 g, 30.3 mmol) was added to a mixture of ethylene glycol-$d_4$ (0.673 mL, 12.1 mmol) and triethylamine (8.41 mL, 60.5 mmol) in DCM (80 mL), and the mixture was stirred at room temperature for 16 h. After this time, DCM (40 mL) was added, and the mixture was washed with water (100 mL). The aqueous layer was extracted with DCM (100 mL), and the combined organic layers were dried over sodium sulfate, filtered, and concentrated in vacuo. The residue obtained was purified by FCC (silica, 0-5% EtOAc in DCM) to afford the title compound. $^1$H NMR (300 MHz, $CDCl_3$) 7.74 (d, J=8.4 Hz, 4H), 7.34 (d, J=7.8 Hz, 4H), 2.46 (s, 6H). MS ($ES^+$) $(M+H)^+$ 375.

Step 2: 2-Fluoroethyl-1,1,2,2-$d_4$ 4-methylbenzenesulfonate

TBAF, 1.0 M in THF (8.97 mL, 8.97 mmol), was added to ethane-1,2-diyl-$d_4$ bis(4-methyl-benzenesulfonate) (2.80 g, 7.48 mmol) in MeCN (17.4 mL), and the mixture was stirred at reflux for 2 h. After this time, the mixture was cooled, diluted with DCM (100 mL), and washed with water (40 mL). The aqueous layer was extracted with DCM (100 mL), and the combined organic layers were dried over sodium sulfate, filtered, and the filtrate was concentrated in vacuo. The residue obtained was purified by FCC (silica, 0-100% DCM in heptane) to afford the title compound. $^1$H NMR (300 MHz, $CDCl_3$) 7.36 (d, J=8.1 Hz, 2H), 7.82 (d, J=8.4 Hz, 2H), 2.46 (s, 3H).

Step 3: (5-(2-Fluoroethoxy-1,1,2,2-$d_4$)pyridin-2-yl) methanol

A mixture of 2-fluoroethyl-1,1,2,2-$d_4$ 4-methylbenzene-sulfonate (363 mg, 1.60 mmol), 6-(hydroxymethyl)pyridin-3-ol (200 mg, 1.60 mmol), and cesium carbonate (1.56 g, 4.80 mmol) in MeCN (20.0 mL) was stirred at 80° C. for 2.5 h. After this time, the reaction mixture was cooled and filtered through diatomaceous earth. The filter cake was rinsed with EtOAc (2×50 mL), and the filtrate was concentrated in vacuo. The residue obtained was purified by FCC (silica, 0-5% MeOH in DCM) to afford the title compound. $^1$H NMR (300 MHz, $CDCl_3$) 8.29 (d, J=2.7 Hz, 1H), 7.29-7.19 (m, 2H), 4.72 (s, 2H), 3.39 (br s, 1H).

Step 4: 2-(Chloromethyl)-5-(2-fluoroethoxy-1,1,2,2-$d_4$)pyridine

Thionyl chloride (0.139 mL, 1.91 mmol) was added to a mixture of (5-(2-fluoroethoxy-1,1,2,2-$d_4$)pyridin-2-yl) methanol (167 mg, 0.953 mmol) in DCM (6.7 mL), and the mixture was stirred at 0° C. for 1 h. After this time, the mixture was poured into water (25 mL), the layers were separated, and the aqueous layer was extracted with DCM (2×25 mL). The combined organic layers were dried over sodium sulfate, filtered, and concentrated in vacuo to afford the title compound. $^1$H NMR (300 MHz, $CDCl_3$) 8.30 (d, J=2.7 Hz, 1H), 7.48 (d, J=8.7 Hz, 1H), 7.36 (dd, J=8.7, 3.0 Hz, 1H), 4.72 (s, 2H).

Step 5: 6-((5-(2-Fluoroethoxy-1,1,2,2-$d_4$)pyridin-2-yl)methoxy)-2-(6-methyl-pyrimidin-4-yl)oxazolo[5,4-b]pyridine Potassium carbonate (391 mg, 2.83 mmol) was added to a mixture of 2-(6-methylpyrimidin-4-yl)oxazolo[5,4-b]pyridin-6-ol (215 mg, 0.942 mmol,) and 2-(chloromethyl)-5-(2-fluoroethoxy-1,1,2,2-$d_4$)pyridine (182 mg, 0.942 mmol) in DMF (5.5 mL), and the mixture was stirred at rt for 16 h and at 40° C. for 5 h. After this time, the mixture was cooled, mixed with water (40 mL), and extracted with EtOAc (3×20 mL) and DCM (20 mL). The combined organic layers were dried over sodium sulfate, filtered, and the filtrate was concentrated in vacuo. The residue obtained was purified by FCC (silica, 0-5% MeOH in DCM) to give the title compound.

Example 1-1: 6-((5-(2-Fluoroethoxy-1,1,2,2-$d_4$) pyridin-2-yl)methoxy)-2-(6-methyl-pyrimidin-4-yl) oxazolo[5,4-b]pyridine $^1$H NMR (300 MHz, $CDCl_3$) 9.32 (d, J=1.2 Hz, 1H), 8.36 (d, J=2.4 Hz, 1H), 8.30 (d, J=2.7 Hz, 1H), 8.10 (d, J=0.6 Hz, 1H), 7.76 (d, J=3.0 Hz, 1H), 7.48 (d, J=8.7 Hz, 1H), 7.31-7.26 (m, 1H), 5.27 (s, 2H), 2.70 (s, 3H). $^{19}$F NMR (282 MHz, $CDCl_3$) −225.80. Tr(METAMRI001)=3.38 min, (ES$^+$) (M+H)$^+$ 386.2, 99%.

The following additional compounds were prepared by Method 1:

Example 1-2: 2-((6-(((2-(6-Methylpyrimidin-4-yl) oxazolo[5,4-b]pyridin-6-yl)oxy)-methyl)pyridin-3-yl)oxy)ethyl 4-methylbenzenesulfonate

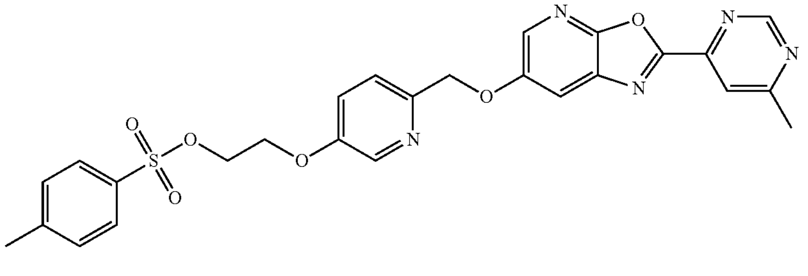

$^1$H NMR (300 MHz, DMSO-$d_6$) 9.31 (d, J=1.2 Hz, 1H), 8.29 (d, J=2.7 Hz, 1H), 8.20 (d, J=3.0 Hz, 1H), 8.10 (s, 1H), 7.82 (d, J=8.4 Hz, 2H), 7.75 (d, J=2.7 Hz, 1H), 7.44 (d, J=8.7 Hz, 1H), 7.36 (d, J=8.1 Hz, 2H), 7.17 (dd, J=8.7, 3.0 Hz, 1H), 5.25 (s, 2H), 4.42-4.39 (m, 2H), 4.24-4.21 (m, 2H), 2.70 (s, 3H), 2.46 (s, 3H). Tr(METAMRI001)=4.05 min, (ES$^+$) (M+H)$^+$ 534.3, 99%.

Example 1-3: 6-((3-Fluoro-5-methoxypyridin-2-yl) methoxy)-2-(6-methylpyrimidin-4-yl)oxazolo[5,4-b] pyridine

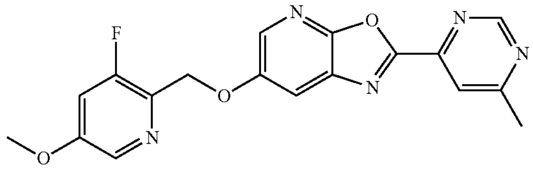

$^1$H NMR (500 MHz, $CDCl_3$) 9.31 (d, J=1.0 Hz, 1H), 8.29 (d, J=3.0 Hz, 1H), 8.20 (d, J=2.0 Hz, 1H), 8.10 (s, 1H), 7.88 (d, J=2.5 Hz, 1H), 7.01 (dd, J=11.0, 2.5 Hz, 1H), 5.31 (d, J=2.0 Hz, 2H), 3.89 (s, 3H), 2.70 (s, 3H). $^{19}$F NMR (282 MHz, $CDCl_3$) −122.91. Tr(METAMRI001)=3.72 min, (ES$^+$) (M+H)$^+$ 368.1, 99%.

Example 1-4: 2-((6-(((2-(6-Methylpyrimidin-4-yl) oxazolo[5,4-b]pyridin-6-yl)oxy)methyl)pyridin-3-yl) oxy)-ethyl-1,1,2,2-$d_4$ 4-methylbenzenesulfonate

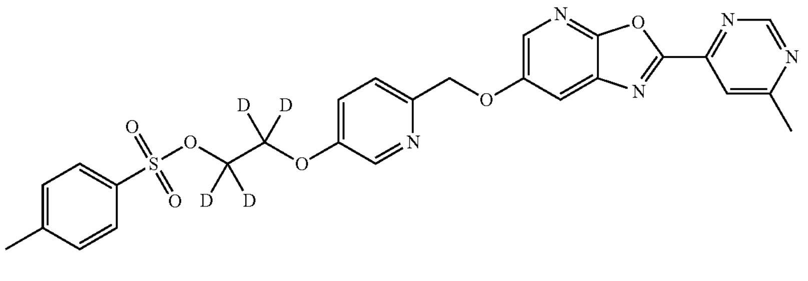

$^1$H NMR (500 MHz, $CDCl_3$) 9.31 (d, J=1.0 Hz, 1H), 8.29 (d, J=3.0 Hz, 1H), 8.20 (d, J=3.0 Hz, 1H), 8.09 (d, J=0.5 Hz, 1H), 7.82 (dd, J=8.5, 2.0 Hz, 2H), 7.75 (d, J=2.5 Hz, 1H), 7.44 (d, J=8.5 Hz, 1H), 7.35 (d, J=8.0 Hz, 2H), 7.17 (dd, J=8.5, 3.0 Hz, 1H), 5.25 (s, 2H), 2.70 (s, 3H), 2.45 (s, 3H). Tr(METAMRI001)=4.37 min, ($ES^+$) $(M+H)^+$ 538.3, 99%.

Method 2

Scheme for Method 2

Scheme for Method 2

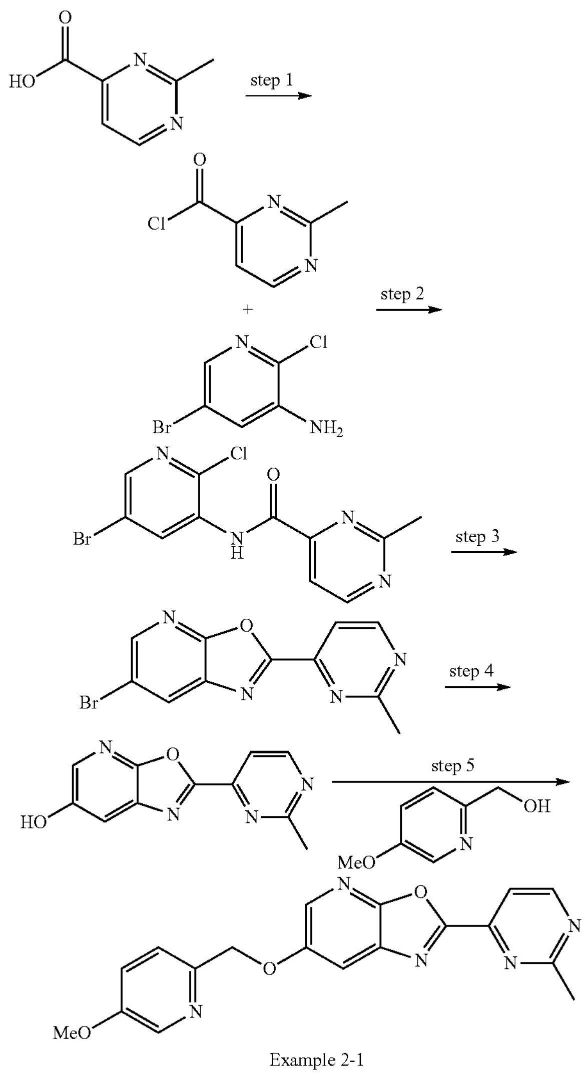

Example 2-1

Step 1: 2-Methylpyrimidine-4-carbonyl chloride

To a solution of 2-methylpyrimidine-4-carboxylic acid (5.0 g, 36.2 mmol) in anhydrous dichloromethane (100 mL) was added N,N-dimethylformamide (0.2 mL) and the reaction was cooled to 0° C. Oxalyl chloride (5.7 mL, 66.2 mmol) was added dropwise and the reaction was allowed to warm to room temperature over 2 hours in a nitrogen atmosphere. The reaction mixture was concentrated in vacuo and co-distilled with dichloromethane (3×30 mL) to afford the title compound. Tr(METCR1410) (MeOH)=0.64 min, ($ES^+$) (M+H)+158, 85%, as the methyl ester.

Step 2: N-(5-Bromo-2-chloropyridin-3-yl)-2-methylpyrimidine-4-carboxamide

To a stirred solution of 2-methylpyrimidine-4-carbonyl chloride (5.7 g, 36.2 mmol) in pyridine (40 mL) at 0° C. was added 5-bromo-2-chloropyridin-3-amine (7.9 g, 38.0 mmol). The mixture was stirred at room temperature overnight. Water was added to the mixture. The precipitate was filtered and washed with water to give the title compound. $^1$H NMR (500 MHz, DMSO-$d_6$) 10.64 (s, 1H), 9.09 (d, J=5.0 Hz, 1H), 8.82 (d, J=2.3 Hz, 1H), 8.46 (d, J=2.3 Hz, 1H), 7.98 (d, J=5.0 Hz, 1H), 2.80 (s, 3H). Tr(METCR1410) =1.23 min, ($ES^+$) $(M+H)^+$ 327, 329, 96%, Step 3: 4-{6-Bromo-[1,3]oxazolo[5,4-b]pyridin-2-yl}-2-methylpyrimidine In duplicate: To a solution of N-(5-bromo-2-chloropyridin-3-yl)-2-methylpyrimidine-4-carboxamide (400 mg, 1.22 mmol) in anhydrous N,N-dimethylformamide (12 mL) in a microwave vessel was added sodium carbonate (129 mg, 1.22 mmol). The reaction vessel was sealed and irradiated at 160° C. for 2 hours. The combined cooled reaction mixtures were concentrated in vacuo and the residue triturated from water. The crude residue was purified by column chromatography (0-100% ethyl acetate in heptane followed by 0-25% methanol in dichloromethane) to give the title compound. $^1$H NMR (500 MHz, DMSO-$d_6$) δ 9.04 (d, J=5.1 Hz, 1H), 8.79 (d, J=2.2 Hz, 1H), 8.67 (d, J=2.2 Hz, 1H), 8.17 (d, J=5.1 Hz, 1H), 2.79 (s, 3H). Tr(METCR1410)=1.01 min, ($ES^+$) $(M+H)^+$ 291, 293, 82%.

The recovered starting material was split (200 mg and 330 mg) and the reaction repeated at greater dilution (in 10 mL and 15 mL N,N-dimethylformamide respectively). The reactions were heated for 7 and 2 hours respectively and purified as above to afford the title compound. $^1$H NMR (500 MHz, DMSO-$d_6$) 9.13-8.95 (m, 1H), 8.78 (d, J=2.2 Hz, 1H), 8.66 (d, J=2.2 Hz, 1H), 8.16 (d, J=5.1 Hz, 1H), 2.78 (s, 3H). Tr(METCR1410)=1.01 min, ($ES^+$) (M+H)+291, 293, 63%.

Step 4: 2-(2-Methylpyrimidin-4-yl)-[1,3]oxazolo[5,4-b]pyridin-6-ol

4-{6-Bromo-[1,3]oxazolo[5,4-b]pyridin-2-yl}-2-methylpyrimidine (170 mg, 0.58 mmol) was dissolved in dioxane (10 mL) and degassed with a stream of $N_2$ for 10 minutes. Potassium acetate (143 mg, 1.46 mmol), bis(pinacolato) diboron (163 mg, 0.64 mmol), and [1,1'-bis(diphenylphosphino)ferrocene]dichloropalladium(II), complex with dichloromethane ($PdCl_2$(dppf)·DCM) (43 mg, 0.06 mmol) were added and the reaction heated at 100° C. under nitrogen for 2.5 hours. After complete conversion to the boronate ester/boronic acid, the reaction mixture was cooled to room temperature. Water (3 mL) was added, followed by sodium perborate tetrahydrate (108 mg, 0.7 mmol), and the reaction mixture was stirred at room temperature for 3 hours. The reaction mixture was diluted with water (5 mL) and resultant precipitate was filtered and dried to afford the title compound. Tr(METCR1410)=0.77 min, ($ES^+$) (M+H)+229, 59%.

Step 5: {4-{6-[(5-Methoxypyridin-2-yl)methoxy]-[1,3]oxazolo[5,4-b]pyridin-2-yl}-2-methylpyrimidine To a pressure tube was added 2-(2-methylpyrimidin-4-yl)-[1,3]oxazolo[5,4-b]pyridin-6-ol (59%, 74 mg, 0.19 mmol), (5-methoxypyridin-2-yl)methanol (26.62 mg, 0.19 mmol), and CMBP (0.06 mL, 0.21 mmol) in toluene. The vessel was sealed and heated at 100° C. for 2 hours. Additional (cyanomethylene)tributylphosphorane (CMBP) (0.10 mL, 0.38 mmol) was added and the reaction mixture was stirred at 110° C. for 7 hours. The cooled reaction mixture was concentrated in vacuo and triturated with 1:1 ethyl acetate: heptane, 3:1 ethyl acetate: heptane, and finally 100% ethanol to afford the title compound.

Example 2-1: {4-{6-[(5-Methoxypyridin-2-yl)methoxy]-[1,3]oxazolo[5,4-b]pyridin-2-yl}-2-methylpyrimidine $^1$H NMR (500 MHz, DMSO-$d_6$) 9.01 (d, J=5.1 Hz, 1H), 8.33 (t, J=3.2 Hz, 2H), 8.20-8.10 (m, 2H), 7.58 (d, J=8.5 Hz, 1H), 7.46 (dd, J=8.6, 2.9 Hz, 1H), 5.29 (s, 2H), 3.85 (s, 3H), 2.78 (s, 3H). Tr(MET-uHPLC-AB-101)=2.28 min, (ES$^+$) (M+H)$^+$ 350.2, 96%

Method 3

Scheme for Method 3

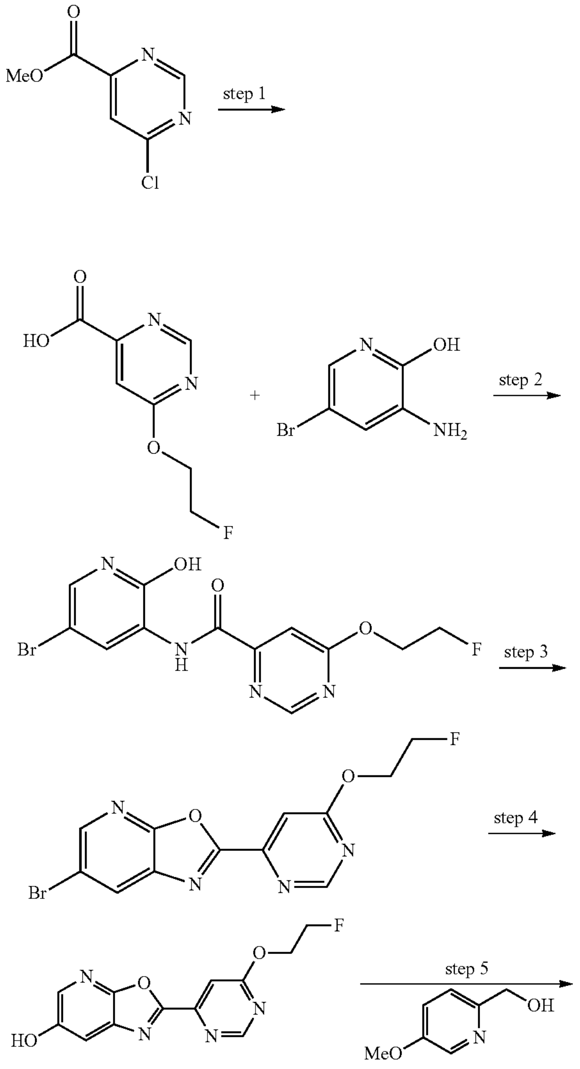

-continued

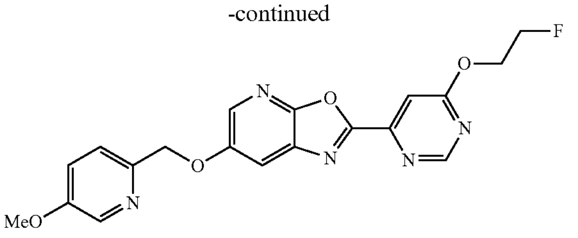

Example 3-1

Step 1: 6-(2-Fluoroethoxy)pyrimidine-4-carboxylic acid

To a stirred solution of 2-fluoroethanol (0.62 mL, 10.7 mmol) in DMF (20 mL) at 0° C. was added sodium hydride (60%, 428 mg, 10.7 mmol). The reaction was stirred for 5 minutes and ethyl 6-chloropyrimidine-4-carboxylate (1.0 g, 5.4 mmol) was added at 0° C. The reaction mixture was warmed to room temperature and stirred for 4 hours. The reaction mixture was quenched with water (15 mL) and diluted with ethyl acetate (15 mL). The organic layer was separated and washed with brine (10 mL). The aqueous phase was acidified using 2 M HCl and extracted with chloroform: isopropanol (3:1, 5×10 mL). The combined organics were dried ($Na_2SO_4$), filtered, and concentrated in vacuo to afford the title compound. $^1$H NMR (250 MHz, DMSO-$d_6$) 8.91 (d, J=1.0 Hz, 1H), 7.40 (d, J=1.0 Hz, 1H), 4.93-4.71 (m, 2H), 4.70-4.55 (m, 2H). Tr(METCR1410) =0.37 min, (ES$^+$) (M+H)$^+$ 187, 100%.

Step 2: N-(5-Bromo-2-hydroxypyridin-3-yl)-6-(2-fluoroethoxy)pyrimidine-4-carboxamide EDC·HCl (745 mg, 3.9 mmol) was added to a solution of 3-amino-5-bromopyridin-2-ol (490 mg, 2.6 mmol) and 6-(2-fluoroethoxy)pyrimidine-4-carboxylic acid (482 mg, 2.6 mmol) in pyridine (20 mL) and the resulting mixture was stirred at room temperature for 15 hours. The reaction mixture was then diluted with water (10 mL) and the resulting precipitate was collected, washed with water and heptane, and dried under vacuum to afford the title compound. $^1$H NMR (500 MHz, DMSO-$d_6$) 12.52 (s, 1H), 10.58 (s, 1H), 9.01 (d, J=1.0 Hz, 1H), 8.46 (d, J=2.6 Hz, 1H), 7.51 (dd, J=7.4, 1.8 Hz, 2H), 4.87-4.74 (m, 2H), 4.74-4.65 (m, 2H). Tr(METCR1410)=1.05 min, (ES$^+$) (M+H)$^+$ 357, 359, 76%.

Step 3: 4-{6-Bromo-[1,3]oxazolo[5,4-b]pyridin-2-yl}-6-(2-fluoroethoxy)pyrimidine A mixture of triphenylphosphine (725 mg, 2.76 mmol), hexachloroethane (818 mg, 3.45 mmol), and triethylamine (0.77 mL, 5.53 mmol) in DCM (25 mL) was stirred for 5 minutes before N-(5-bromo-2-hydroxypyridin-3-yl)-6-(2-fluoroethoxy)pyrimidine-4-carboxamide (94%, 525 mg, 1.38 mmol) was added. The reaction mixture was stirred at room temperature for 20 hours. After standing overnight, a precipitate was observed. The precipitate was collected and dried under vacuum to afford the title compound. Tr(METCR1600)=1.05 min, (ES$^+$) (M+H)$^+$ 339, 341, 88%.

Step 4: 2-[6-(2-Fluoroethoxy)pyrimidin-4-yl]-[1,3]oxazolo[5,4-b]pyridin-6-ol In duplicate: 4-{6-bromo-[1,3]oxazolo[5,4-b]pyridin-2-yl}-6-(2-fluoroethoxy)pyrimidine (195 mg, 0.58 mmol) was dissolved in THF (10 mL) in a pressure tube and de-gassed with a stream of $N_2$ for 10 minutes. Potassium acetate (141 mg, 1.44 mmol), bis(pinacolato)diboron (161 mg, 0.63 mmol), and $PdCl_2$(dppf) (42 mg, 0.06 mmol) were added and the reaction vessel was sealed and heated at 80° C. under nitrogen for 16 hours. The reaction mixtures were combined and cooled to room temperature. Water (5 mL) was added and the resultant precipitate was removed by filtration. Sodium perborate tetrahydrate (212 mg, 1.38 mmol) was added to the filtrate and the reaction mixture was stirred at room temperature for 4.5 hours.

The reaction mixture was concentrated in vacuo and water (10 mL) was added. The precipitate was collected by vacuum filtration and dried further under vacuum at 40° C. for 2 hours to afford the title compound. $^1$H NMR (500 MHz, DMSO-$d_6$) 10.29 (s, 1H), 9.02 (s, 1H), 8.06 (s, 1H), 7.69 (s, 2H), 4.86 (s, 1H), 4.75 (d, J=11.8 Hz, 2H), 4.68 (s, 1H). Tr(METCR1410)=0.89 min, (ES$^+$) (M+H) 277, 74%.

Step 5: 4-(2-Fluoroethoxy)-6-{6-[(5-methoxypyridin-2-yl)methoxy]-[1,3]oxazolo[5,4-b]pyridin-2-yl}pyrimidine To a pressure tube was added 2-[6-(2-fluoroethoxy)pyrimidin-4-yl]-[1,3]oxazolo[5,4-b]pyridin-6-ol (74%, 223 mg, 0.6 mmol), (5-methoxypyridin-2-yl)methanol (91 mg, 0.66 mmol), and CMBP (0.19 mL, 0.72 mmol) in toluene (5 mL). The vessel was sealed and heated at 100° C. for 5 hours. The reaction mixture was retreated with (5-methoxypyridin-2-yl)methanol (91 mg, 0.66 mmol) and CMBP (0.19 mL, 0.72 mmol) and stirred at 100° C. for a further 15 hours. The cooled reaction mixture was concentrated in vacuo and purified by column chromatography (0-20% methanol in DCM) then by prep HPLC to afford the title compound.

Example 3-1: 4-(2-Fluoroethoxy)-6-{6-[(5-methoxypyridin-2-yl)methoxy]-[1,3]oxazolo[5,4-b]pyridin-2-yl}pyrimidine $^1$H NMR (500 MHz, DMSO-$d_6$) 9.04 (d, J=1.0 Hz, 1H), 8.33-8.31 (m, 2H), 8.16 (d, J=2.8 Hz, 1H), 7.72 (d, J=1.0 Hz, 1H), 7.57 (d, J=8.5 Hz, 1H), 7.45 (dd, J=8.6, 2.9 Hz, 1H), 5.28 (s, 2H), 4.89-4.66 (m, 2H), 4.78-4.74 (m, 2H), 3.84 (s, 3H). Tr(MET-uHPLC-AB-101)=2.67 min, (ES$^+$) (M+H)$^+$ 398, 99%.

Method 4

Scheme for Method 4

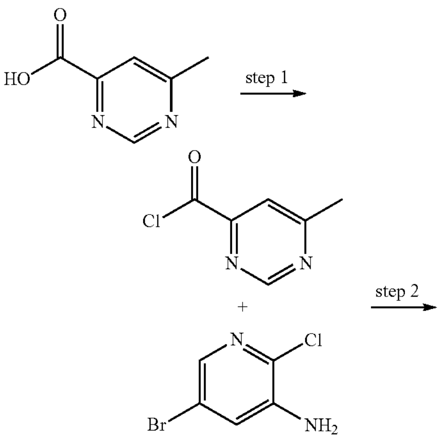

-continued

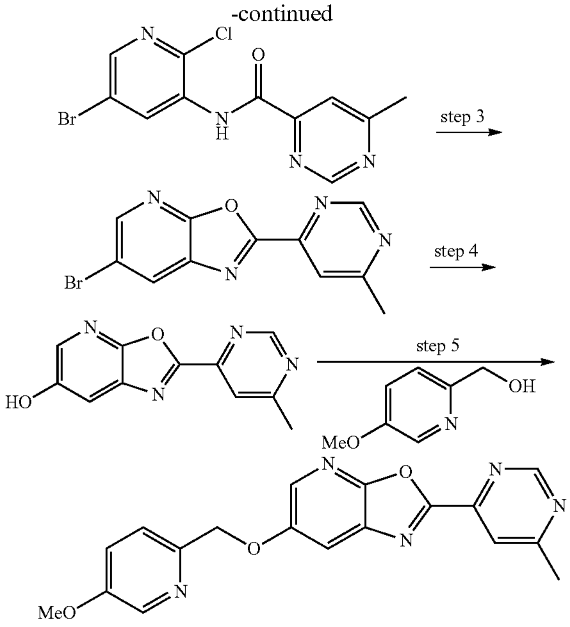

Example 4-1

Steps 1 and 2: N-(5-Bromo-2-chloropyridin-3-yl)-6-methylpyrimidine-4-carboxamide To a solution of 5-bromo-2-chloropyridin-3-amine (1.61 g, 7.8 mmol) in pyridine (25 mL) was added 6-methylpyrimidine-4-carboxylic acid (1.07 g, 7.8 mmol) at room temperature. The reaction mixture was then cooled to 0° C. and phosphorus (V) oxychloride (1.44 ml, 15.5 mmol) was added dropwise over 10 minutes. The reaction mixture was stirred at 0° C. for 1 hour, then quenched at 0° C. with water (10 mL) and then concentrated in vacuo. The residue was triturated with water to afford the title compound. $^1$H NMR (500 MHz, DMSO-$d_6$) δ 10.64 (s, 1H), 9.31 (d, J=1.2 Hz, 1H), 8.79 (d, J=2.3 Hz, 1H), 8.46 (d, J=2.3 Hz, 1H), 8.10 (s, 1H), 2.65 (s, 3H). Tr(METCR1410)=1.24 min, (ES$^+$) (M+H)$^+$ 327, 329, 100%.

Step 3: 4-{6-Bromo-[1,3]oxazolo[5,4-b]pyridin-2-yl}-6-methylpyrimidine

In quadruplicate: To a solution of N-(5-bromo-2-chloropyridin-3-yl)-6-methylpyrimidine-4-carboxamide (400 mg, 1.22 mmol) in anhydrous N,N-dimethylformamide (15 mL) in a microwave vessel was added sodium carbonate (129 mg, 1.22 mmol). The vessel was sealed and irradiated at 160° C. for 4 hours. The cooled reaction mixture was concentrated in vacuo and the residue was triturated with water. The crude residue was purified by column chromatography (0-100% EtOAc in heptane followed by 0-20% methanol in DCM) to give the title compound. $^1$H NMR (500 MHz, DMSO-$d_6$) δ 9.32 (d, J=1.2 Hz, 1H), 8.78 (d, J=2.2 Hz, 1H), 8.66 (d, J=2.2 Hz, 1H), 8.32-8.26 (m, 1H), 2.65 (s, 3H). Tr(METCR1410)=1.01 min, (ES$^+$) (M+H)$^+$ 291, 293, 66%.

Step 4: 2-(6-Methylpyrimidin-4-yl)-[1,3]oxazolo[5,4-b]pyridin-6-ol

4-{6-Bromo-[1,3]oxazolo[5,4-b]pyridin-2-yl}-6-methylpyrimidine (66%, 163 mg, 0.37 mmol) was dissolved in dioxane (10 mL) in a pressure tube and de-gassed with a stream of $N_2$ for 10 minutes. Potassium acetate (91 mg, 0.92 mmol), bis(pinacolato)diboron (103 mg, 0.41 mmol), and $PdCl_2$(dppf) (27 mg, 0.04 mmol) were added, and the reaction vessel sealed and heated at 100° C. under nitrogen for 4 hours. After complete conversion to the boronate ester/boronic acid, the reaction mixture was cooled to room temperature, water (3 mL) was added, and the resultant precipitate was collected and removed. Sodium perborate tetrahydrate (78 mg, 0.50 mmol) was added to the filtrate and the reaction mixture was stirred at room temperature for 17 hours. The reaction mixture was quenched with water (5 mL) and concentrated in vacuo. The residue was diluted with water (3 mL) and the resultant collected and dried by vacuum filtration to afford the title compound. Tr(METCR1410)=0.81 min, ($ES^+$) (M+H)+229, 43%.

Step 5: 4-{6-[(5-Methoxypyridin-2-yl)methoxy]-[1,3]oxazolo[5,4-b]pyridin-2-yl}-6-methylpyrimidine To a pressure tube was added 2-(6-methylpyrimidin-4-yl)-[1,3]oxazolo[5,4-b]pyridin-6-ol (47%, 70 mg, 0.14 mmol), (5-methoxypyridin-2-yl)methanol (40 mg, 0.29 mmol), and CMBP (0.08 mL, 0.29 mmol) in toluene (5 mL).

The vessel was sealed and heated at 75° C. for 8 hours. The reaction mixture was re-treated with (5-methoxypyridin-2-yl)methanol (40 mg, 0.29 mmol) and CMBP (0.08 mL, 0.29 mmol), and heated at 75° C. for 10 hours. The reaction mixture was again re-treated with (5-methoxypyridin-2-yl) methanol (40 mg, 0.29 mmol) and CMBP (0.08 mL, 0.29 mmol), and heated at 75° C. for 3 hours. The cooled reaction mixture was concentrated in vacuo and triturated with 3:1 EtOAc:heptane, followed by 3:1 ethanol:water. The material was purified twice by column chromatography (0-10% methanol in DCM and then separately with 0-10% EtOAc in heptane followed by 0-10% methanol in DCM). Trituration with ethanol and prep HPLC (high pH) gave the title compound.

Example 4-1: 4-{6-[(5-Methoxypyridin-2-yl)methoxy]-[1,3]oxazolo[5,4-b]pyridin-2-yl}-6-methylpyrimidine $^1H$ NMR (500 MHz, DMSO-$d_6$) 9.29 (d, J=1.2 Hz, 1H), 8.35-8.30 (m, 2H), 8.26 (s, 1H), 8.16 (d, J=2.7 Hz, 1H), 7.57 (d, J=8.6 Hz, 1H), 7.46 (dd, J=8.6, 3.0 Hz, 1H), 5.29 (s, 2H), 3.84 (s, 3H), 2.64 (s, 3H). Tr(MET-uHPLC-AB-101)=2.31 min, ($ES^+$) $(M+H)^+$ 350, 100%.

Method 5

Scheme for Method 5

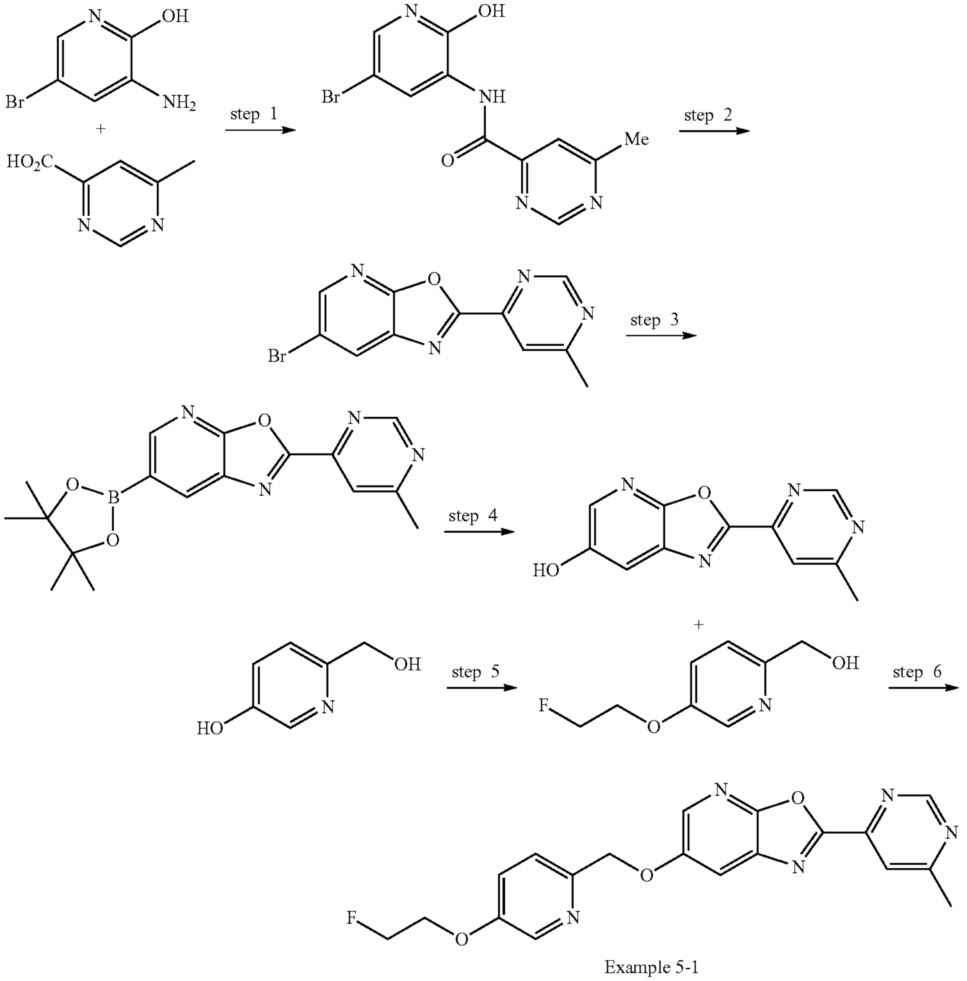

Example 5-1

Step 1: N-(5-Bromo-2-hydroxypyridin-3-yl)-6-methylpyrimidine-4-carboxamide

A mixture of 3-amino-5-bromopyridin-2-ol (1.37 g, 7.25 mmol) in DCM (109 mL) was treated with 6-methylpyrimidine-4-carboxylic acid (1.00 g, 7.25 mmol), and the mixture was cooled to 0° C. and treated with pyridine (2.92 mL, 36.2 mmol) and EDC (2.08 g, 10.9 mmol). The mixture was stirred at 0° C. for 10 min and at rt for 16 h. After this time, the mixture was concentrated in vacuo. The residue obtained was triturated with DCM (10 mL), and the resultant was collected by filtration and dried in vacuo to give the title compound. $^1$H NMR (300 MHz, DMSO-$d_6$) 12.56 (br s, 1H), 10.63 (s, 1H), 9.27 (d, J=1.2 Hz, 1H), 8.45 (d, J=2.7 Hz, 1H), 8.06 (d, J=0.6 Hz, 1H), 7.51 (d, J=2.7 Hz, 1H), 2.63 (s, 3H).

Step 2: 6-Bromo-2-(6-methylpyrimidin-4-yl)oxazolo[5,4-b]pyridine

A mixture of triphenylphosphine (3.56 g, 13.6 mmol) and hexachloroethane (2.01 g, 8.49 mmol) in DCM (79 mL) was treated with triethylamine (3.78 mL, 27.2 mmol) dropwise over 15 min. The mixture was stirred at rt for 10 min. N-(5-Bromo-2-hydroxypyridin-3-yl)-6-methylpyrimidine-4-carboxamide (1.05 g, 3.40 mmol) was then added, and the mixture was stirred at rt for 16 h. After this time, the mixture was washed with saturated aqueous sodium bicarbonate (100 mL) and water (100 mL). The organic layer was dried over sodium sulfate, filtered, and the filtrate was concentrated in vacuo. The residue obtained was purified by FCC (silica, 0-5% MeOH in DCM) to give the title compound. $^1$H NMR (300 MHz, DMSO-$d_6$) 9.34 (d, J=0.9 Hz, 1H), 8.56 (d, J=2.1 Hz, 1H), 8.33 (d, J=2.1 Hz, 1H), 8.13 (d, J=0.6 Hz, 1H), 2.72 (s, 3H).

Step 3: 2-(6-Methylpyrimidin-4-yl)-6-(4,4,5,5-tetramethyl-1,3,2-dioxaborolan-2-yl)oxazolo[5,4-b]pyridine A mixture of 6-bromo-2-(6-methylpyrimidin-4-yl)oxazolo[5,4-b]pyridine (350 mg, 1.20 mmol), bis(pinacolato) diboron (458 mg, 1.80 mmol), potassium acetate (295 mg, 3.01 mmol), $PdCl_2$(dppf) (88 mg, 0.12 mmol), and THF (8.8 mL) was heated at 90° C. for 7 h. After this time, the mixture was cooled and treated with water (5 mL). The resultant was collected by filtration, washed with water (3 mL), and dried in vacuo to give the title compound. $^1$H NMR (300 MHz, DMSO-$d_6$) 9.32 (d, J=1.2 Hz, 1H), 8.71 (d, J=1.2 Hz, 1H), 8.50 (d, J=1.5 Hz, 1H), 8.32 (d, J=0.6 Hz, 1H), 2.65 (s, 3H), 1.36 (s, 12H).

Step 4: 2-(6-Methylpyrimidin-4-yl)oxazolo[5,4-b]pyridin-6-ol

A mixture of 2-(6-methylpyrimidin-4-yl)-6-(4,4,5,5-tetramethyl-1,3,2-dioxaborolan-2-yl)-oxazolo[5,4-b]pyridine (435 mg, 1.29 mmol) in THF (22.0 mL) was treated with a mixture of sodium perborate tetrahydrate (237 mg, 1.54 mmol) in water (22.0 mL), and the mixture was stirred at rt for 1 h. After this time, the mixture was treated with saturated aqueous ammonium chloride (10 mL). The volatiles were removed in vacuo, and the resulting aqueous suspension was filtered. The collected material was washed with water (15 mL), dried in vacuo, and purified by FCC (silica, 0-5% MeOH in DCM) to give the title compound. $^1$H NMR (300 MHz, DMSO-$d_6$) 10.29 (s, 1H), 9.28 (d, J=1.2 Hz, 1H), 8.24 (d, J=0.9 Hz, 1H), 8.07 (d, J=2.7 Hz, 1H), 7.69 (d, J=2.7 Hz, 1H), 2.63 (s, 3H).

Step 5: (5-(2-Fluoroethoxy)pyridin-2-yl)methanol

A mixture of 6-(hydroxymethyl)pyridin-3-ol (270 mg, 2.16 mmol) and potassium carbonate (447 mg, 3.23 mmol) in anhydrous MeCN (6 mL) was treated with 1-bromo-2-fluoroethane (0.32 mL, 4.3 mmol), and the resulting reaction mixture was heated at 70° C. for 24 h in a sealed tube. After this time, the reaction mixture was cooled to rt, diluted with water (50 mL), and extracted with EtOAc (3×50 mL). The organic layers were combined, dried over sodium sulfate, filtered, and the filtrate concentrated under reduced pressure to afford the title compound, that was used in the next step without further purification. $^1$H NMR (300 MHz, DMSO-$d_6$) 8.22 (dd, J=2.7, 0.6 Hz, 1H), 7.45-7.37 (m, 2H), 5.32 (t, J=5.7 Hz, 1H), 4.85-4.82 (m, 1H), 4.69-4.66 (m, 1H), 4.49 (d, J=5.7 Hz, 2H), 4.37-4.34 (m, 1H), 4.27-4.24 (m, 1H). MS (ES$^+$) (M+H)$^+$ 172.

Step 6: 6-((5-(2-Fluoroethoxy)pyridin-2-yl)methoxy)-2-(6-methylpyrimidin-4-yl)oxazolo[5,4-b]pyridine CMBP (0.23 mL, 0.88 mmol) was added to a mixture of 2-(6-methylpyrimidin-4-yl)oxazolo[5,4-b]pyridin-6-ol (100 mg, 0.438 mmol) and (5-(2-fluoroethoxy)pyridin-2-yl)methanol (113 mg, 0.657 mmol) in anhydrous toluene (5 mL), and the mixture was heated at 100° C. for 2 h. After this time, the mixture was cooled to room temperature, adsorbed onto silica gel with 1:1 MeOH/DCM (100 mL), and purified by FCC (silica, 0-10% MeOH in DCM). The product was triturated with acetonitrile to give the title compound.

Example 5-1: 6-((5-(2-Fluoroethoxy)pyridin-2-yl)methoxy)-2-(6-methylpyrimidin-4-yl) oxazolo[5,4-b]pyridine $^1$H NMR (500 MHz, DMSO-$d_6$) 9.29 (d, J=1.0 Hz, 1H), 8.35 (d, J=3.0 Hz, 1H), 8.32 (d, J=2.5 Hz, 1H), 8.25 (s, 1H), 8.15 (d, J=2.5 Hz, 1H), 7.58 (d, J=8.5 Hz, 1H), 7.50 (dd, J=8.5, 3.0 Hz, 1H), 5.30 (s, 2H), 4.82-4.81 (m, 1H), 4.73-4.71 (m, 1H), 4.39-4.37 (m, 1H), 4.33-4.31 (m, 1H), 2.64 (s, 3H). $^{19}$F NMR (282 MHz, DMSO-$d_6$)-222.33. Tr (METAMRI002)=3.00 min, (ES$^+$) (M+H)$^+$ 382.2, 98%.

The following additional compounds were prepared by Method 1:

Example 5-2: 6-((5-(Allyloxy)pyridin-2-yl)methoxy)-2-(6-methylpyrimidin-4-yl) oxazolo[5,4-b]pyridine

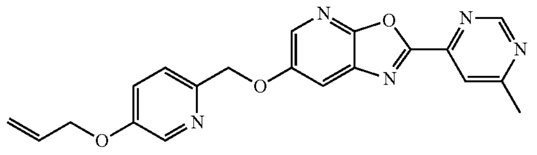 [SMILES: C=CCOc1ccc(COc2cnc3oc(-c4cc(C)ncn4)nc3c2)nc1]

$^1$H NMR (500 MHz, DMSO-$d_6$) 9.29 (d, J=0.9 Hz, 1H), 8.33-8.32 (m, 2H), 8.25 (d, J=0.3 Hz, 1H), 8.15 (d, J=1.5 Hz, 1H), 7.56 (d, J=5.1 Hz, 1H), 7.46 (dd, J=5.4, 1.8 Hz, 1H), 6.09-6.01 (m, 1H), 5.44-5.40 (m, 1H), 5.31-5.28 (m, 3H), 4.68-4.67 (m, 2H), 2.64 (s, 3H). Tr (METAMRI002)=13.03 min, ($ES^+$) $(M+H)^+$ 376.1, 99%.

Example 5-3: 6-((5-(Fluoromethoxy)pyridin-2-yl) methoxy)-2-(6-methylpyrimidin-4-yl) oxazolo[5,4-b]pyridine

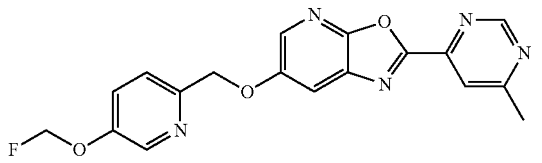 [SMILES: Cc1cc(-c2nc3cc(OCc4ccc(OCF)cn4)cnc3o2)ncn1]

$^1H$ NMR (500 MHz, DMSO-$d_6$) 9.29 (d, J=1.0 Hz, 1H), 8.45 (d, J=1.5 Hz, 1H), 8.34 (d, J=2.5 Hz, 1H), 8.25 (s, 1H), 8.16 (d, J=3.0 Hz, 1H), 7.66 (d, J=1.5 Hz, 2H), 5.94 (d, J=54.0 Hz, 2H), 5.34 (s, 2H), 2.64 (s, 3H). 19F NMR (282 MHz, DMSO-$d_6$)-151.59. Tr (METAMRI002)=12.49 min, ($ES^+$) $(M+H)^+$ 368.1, 98%.

Method 6

Scheme for Method 6

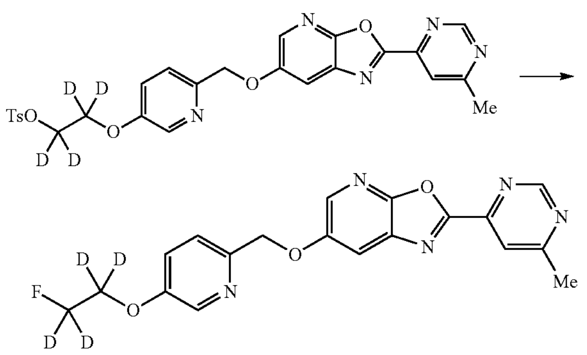

6-((5-2-fluoroethoxy-1,1,2,2-$d_4$)pyridin-2-yl)methoxy)-2-(6-methylpyrimidin-4-yl)oxazolo[5,4-b]pyridine (Example 1-1) To a stirring mixture of potassium fluoride (0.00011 g, 0.0019 mmol), 4,7,13,16,21,24-hexaoxa-1,10-diazabicyclo[8.8.8]hexacosane (K222, 0.00418 g, 0.011 mmol), and 2-(tert-butyl)-1,1,3,3-tetramethylguanidine (BTMG, 0.0019 g, 0.011 mmol) in dimethyl sulfoxide (0.35 mL) was added 2-((6-(((2-(6-methylpyrimidin-4-yl)oxazolo [5,4-b]pyridin-6-yl)oxy)methyl)pyridin-3-yl)oxy)ethyl-1,1,2,2-$d_4$ 4-methylbenzenesulfonate (Example 1-4) (0.00199 g, 0.00370 mmol), and the mixture was stirred at 100° C. for 30 min. After this time, the reaction mixture was cooled to room temperature, mixed with formic acid (0.1 mL), and injected through a syringe filter (0.2 m) onto an XBridge C18 column (5 μm ODB, 19×250 mm), eluted with 22% CAN in water (0.1% formic acid v/v) for 30 min (20 mL/min). The fractions collected between 19.87 and 21.32 min were concentrated to afford 6-((5-(2-fluoroethoxy-1,1,2,2-$d_4$)pyridin-2-yl)methoxy)-2-(6-methylpyrimidin-4-yl) oxazolo[5,4-b]pyridine: $^1H$ NMR (500 MHz, DMSO-$d_6$) δ 9.29 (s, 1H), 8.35 (d, J=2.9 Hz, 1H), 8.32 (d, J=2.7 Hz, 1H), 8.25 (s, 1H), 8.15 (d, J=2.7 Hz, 1H), 7.58 (d, J=8.6 Hz, 1H), 7.50 (dd, J=8.6, 2.9 Hz, 1H), 5.29 (s, 2H), 2.63 (s, 3H); MS (ESI) m/z 386 $[M+H]^+$; HPLC (Phenomenex Luna C18(2), 5 μm, 4.6×150 mm), 5-90% ACN in water (0.1% TFA v/v) over 20 min (1.15 mL/min), $t_R$=8.28 min, >99% (AUC) at 254 and 215 nm.

Biological Assays

Exon1-Q46 Radioligand Binding Assay

For radioligand binding assays (RBA), MBP-HTT(1-89) Q46-His(6×) ("Exon1-Q46") protein was generated based on a previous publication (Scherzinger et al. Cell, Vol. 90, 549-558, Aug. 8, 1997). For experiments, 30 μM MBP-Exon1-Q46 was incubated with 150 μg/mL thrombin in assay buffer (150 mM NaCl, 50 mM Tris pH 8.0) and 2 mM $CaCl_2$ for 16 hours at 37° C. Aggregated Exon1-Q46 was pelleted by centrifugation for 5 minutes at 13,000 rpm in a bench top centrifuge and re-dissolved in the same volume of assay buffer. Test compounds were prepared by titration in DMSO at 11 concentrations from 63 μM to 2 nM. For the RBA, Exon1-Q46 protein aggregates and test compounds were pre-incubated in assay buffer for 20 minutes at room temperature, in 100 μL/well in a 96-well plate (pp, round bottom). Then, ligand was added in 50 L/well and incubated for 60 minutes at 37° C. Final assay concentrations were 1 μM to 30 μM test compound, 1 μM Exon1-Q46 protein (equivalent monomer concentration), and 0.3 nM ligand [$^3H_3$-methyl]-5-((5-methoxypyridin-2-yl)methoxy)-2-(pyrazin-2-yl)benzo[d]oxazole. Samples were transferred onto GF/B filter plates and washed 2× with 200 μL PBS using a Filtermate Harvester. After drying filter plates for 1 hour at 55° C., the back of the plates were sealed with foil and 30 μL/well scintillation fluid (Packard MicroScint 40) added, incubated for 15 minutes in the dark, and counted in a MicroBeta reader. For analysis, replicate data from independent assay plates were normalized towards 0% and 100% inhibition using control wells of vehicle (0% inhibition) and 1 M unlabelled [$^3H_3$-methyl]-5-((5-methoxypyridin-2-yl) methoxy)-2-(pyrazin-2-yl)benzo[d]oxazole (100% inhibition). $IC_{50}$ values were determined with a sigmoidal inhibition model with four variables (top, bottom, slope, $IC_{50}$) in a global fit using the normalized replicate data.

The results for various example compounds were as provided in the table below (+++<100 nM; ++100-500 nM; +>500 nM; ND: not determined):

| Compound No. | Potency Range |
|---|---|
| 1-1 | +++ |
| 1-2 | +++ |
| 1-3 | +++ |
| 2-1 | +++ |
| 3-1 | +++ |
| 4-1 | +++ |
| 5-1 | +++ |
| 5-2 | +++ |
| 5-3 | +++ |

Imaging in a Mouse Model and Deuterium Effect on Bone Uptake

A total of 61 wild-type (WT) and 68 heterozygous (HET) Q175DN mice at 3 and 9 months of age were included in the study. Dynamic μPET/CT imaging (90 min for $^{18}F$-labeled Compound 1-1) was performed in HET Q175DN mice and WT littermates.

Dynamic PET Scan

MicroPET/CT imaging was performed on two Siemens Inveon PET-CT scanners (Siemens Preclinical Solution, USA). Animals (both wild type (WT) and the HET Q175DN mice that carries one copy of the expanded human HTF exon-1 gene) were placed side by side on the scanner bed with the heart of the animals in the scanner's field of view. Anesthesia was induced by inhalation of isoflurane (5% for induction, and 1.5-2% for maintenance during preparation and scanning) supplemented with oxygen. After induction, all mice were catheterized in the tail vein for intravenous (i.v.) bolus injection of the tracer and placed on the scanner bed. Respiration was constantly monitored using the Monitoring Acquisition Module (Minerve, France) during the entire scanning period. The core body temperature of the animals was maintained using a warm air flow.

At the onset of the 120 min (for proof-of-concept) or 90 min (for the cross-sectional study) dynamic microPET scan, mice were injected with a bolus of radiotracer over a 12 second interval (1 mL/min) using an automated pump (Pump 11 Elite, Harvard Apparatus, USA). Tracer was injected with an activity as high as possible to obtain good image quality, while keeping the cold dose as low as possible. Overall, HET Q175DN animals were injected with a bolus of 6.8±2.9 MBq, while WT littermates were injected with a bolus of 7.0±1.9 MBq. PET data were acquired in list mode. Following the microPET scan, a 10 min 80 kV/500 μA CT scan was performed for attenuation and scatter correction.

PET image processing

Acquired PET data were reconstructed into 45 or 39 frames (depending on scan duration) of increasing length (12×10 s, 3×20 s, 3×30 s, 3×60 s, 3×150 s, and 21 or 15×300 s) using a list-mode iterative reconstruction with proprietary spatially variant resolution modeling with 8 iterations and 16 subsets of the 3D ordered subset expectation maximization (OSEM 3D) algorithm. Normalization, dead time, random, decay, and CT-based attenuation corrections were applied. PET image frames were reconstructed on a 128×128×159 grid with 0.776×0.776×0.796 $mm^3$ voxels. Image analysis was performed with PMOD 3.6 software (Pmod Technologies, Zurich, Switzerland) for any regional based analysis. Spatial normalization of the PET/CT images was done through rigid matching of the CT and PET imaging to the CT image of the Waxholm template. Time activity curves (SUV TACs) of different regions (striatum, motor cortex, cerebellum, thalamus, and hippocampus) were extracted from the images. Kinetic data were investigated for different models (1TCM, 2TCM, 3TCM, and Logan linear model) and then finally fitted by the two tissue compartments model (2TCM) to calculate the total volume of distribution ($V_T$) using an image derived input function (IDIF) based on the 90 minutes data. The input function was obtained from the whole blood activity derived from the PET images by putting a volume-of-interest (threshold based 50% of max) in the lumen of the left ventricle.

Analysis

Pharmacokinetic modeling was performed for regional quantification. Parallel assessment of various kinetic models was performed to define the most suitable method for PET imaging using $^{18}$F-labeled Compound 1-1 as a tracer. Fractional uptake (Ki (IDIF)) (3sTCM) for $^{18}$F-labeled Compound 1-1 was calculated using an image-derived input function (IDIF) (not pictured).

In vivo radiometabolite profiles were determined in plasma and brain of 9 months old Q175DN mice (n=3-6 per genotype and time point) at 5-, 15-, 30-, 45-, 60-, and 90-min post-injection. No brain-penetrant radiometabolite species were observed. A comparison study at 3 months of age with a comparator compound was executed (n=18-20 per genotype) (not pictured).

Average $^{18}$F-labeled Compound 1-1 SUV images at 60-90 min of HET and WT mice was determined. As predicted, SUV images at 60-90 min post-injection displayed elevated values in HET compared to WT.

Radiometabolite analysis revealed a favorable plasma profile with no apparent brain-penetrant species. Significant differences between genotypes at 9 months of age could be measured in all relevant regions. An injected mass dose below 0.8 g/kg was found workable. Test-Retest variability was moderate and intra-animal variability was noted.

In comparison to a comparator compound, in mice at 3 months of age, $^{18}$F-labeled Compound 1-1 displayed higher discrimination power.

Figure 2:
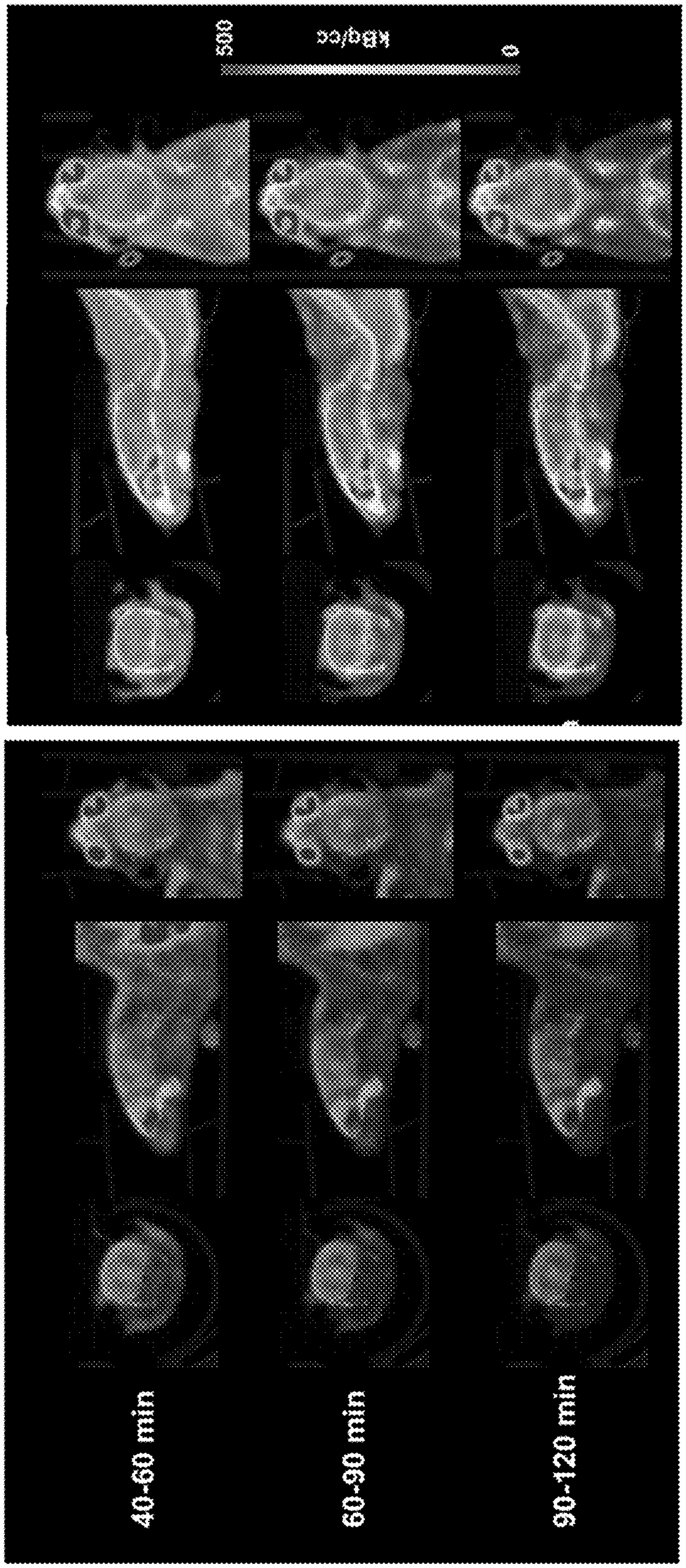
FIG. 2 depicts PET images for Compound 1-1 and Compound 5-1 for three different time periods following administration in mice.

Using a similar methodology, following administration in mice, SUV of Compound $^{18}$F-labeled Compound 1-1 and Compound 5-1 bone uptake of fluorine-18 was measured. A graph of the bone uptake SUV results is depicted in FIG. 1, while PET images for 40-60 min, 60-90 min, and 90-120 min are provided in FIG. 2. Images are overlaid onto MRI mouse brain template for anatomical localization. Based on the results, it can be seen that $^{18}$F-labeled Compound 1-1 provided superior PET imaging resolution due to reduced cleavage of the terminal fluoride in vivo in subject animals.

PET Imaging Example

The following example provides an illustrative, non-limiting, procedure that may be utilized when performing PET imaging studies on an individual in a clinical setting. The individual is either unmedicated or pre-medicated with an unlabeled compound. The individual may undergo fasting, allowing water intake ad libitum, prior to PET imaging. A 20 G two inch venous catheter is inserted into the contralateral ulnar vein for administration of the imaging agent.

The human subject is positioned in the PET camera and a tracer dose of imaging agent is administered via i.v. catheter. Either arterial or venous blood samples are taken at appropriate time intervals throughout the PET scan in order to analyze and quantitate the fraction of unmetabolized compound in plasma. Images are acquired for up to 120 minutes. Within ten minutes of the injection of radiotracer and at the end of the imaging session, 1 mL blood samples are obtained for determining the plasma concentration of any unlabeled imaging agent compound (or other compound of intervention) which may have been administered before the PET tracer.

Tomographic images are obtained through image reconstruction. For example, for determining the distribution of imaging agent, regions of interest (ROIs) are drawn on the reconstructed image. Regions of interest in a brain image may include, for example, the striatum, cerebellum, or basal ganglia. Imaging agent uptake over time in these regions may be used to generate time activity curves (TAC). Data may be expressed as radioactivity per unit time per unit volume (e.g., μCi/cc/mCi injected dose), or as radioactivity per unit volume. TAC data may be processed with various methods known in the field to yield quantitative parameters, an example of which is Binding Potential (BP). For further description of imaging procedure, see, for example, Waxman A.D., et al., Society of Nuclear Medicine Procedure Guideline for FDG PET Brain Imaging, ver. 1.0, (Feb. 8, 2009).

Unless otherwise defined, all technical and scientific terms used herein have the same meaning as commonly understood by one of ordinary skill in the art to which this disclosure belongs.

The disclosures illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the disclosure.

All publications, patent applications, patents, and other references mentioned herein are expressly incorporated by reference in their entirety, to the same extent as if each were incorporated by reference individually. In case of conflict, the present specification, including definitions, will control.

The invention claimed is:

1. A compound that is:

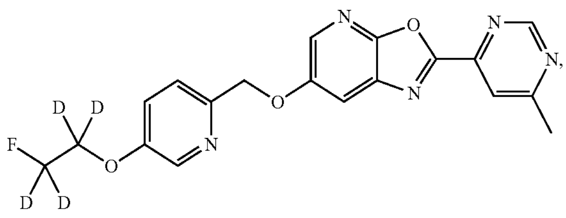 [SMILES: [2H]C([2H])(F)C([2H])([2H])Oc1ccc(COc2cnc3oc(-c4cc(C)ncn4)nc3c2)nc1]

or a pharmaceutically acceptable salt thereof, optionally wherein the compound, or a pharmaceutically acceptable salt thereof, is labeled with a positron-emitting isotope.

2. The compound of claim 1, wherein the compound, or a pharmaceutically acceptable salt thereof, is labeled with a positron-emitting isotope.

3. The compound of claim 2, wherein the compound, or a pharmaceutically acceptable salt thereof, contains a positron-emitting isotope selected from $^{11}C$, $^{13}N$, $^{15}O$, and $^{18}F$.

4. An imaging agent comprising the compound of claim 2, or a pharmaceutically acceptable salt thereof.

5. A method of detecting a presence or absence of a protein susceptible to aggregation in an individual comprising administering an effective amount of a compound of claim 2, or a pharmaceutically acceptable salt thereof, to the individual, and generating an image of a body part or body area of the individual.

6. The method of claim 5, wherein the presence or absence of a protein aggregate corresponds to a presence or absence of a neurodegenerative disease.

7. The method of claim 6, wherein the neurodegenerative disease is selected from Alzheimer's disease, amyotrophic lateral sclerosis, Huntington's disease, Parkinson's disease, Prion disease, and spinocerebellar ataxias.

8. The method of claim 5, wherein generating an image comprises positron emission tomography (PET) imaging, PET with concurrent computed tomography imaging (PET/CT), PET with concurrent magnetic resonance imaging (PET/MRI), single-photon emission computed tomography (SPECT) imaging, or a combination thereof.

* * * * *

SEQUENCE LISTING

```
<160> NUMBER OF SEQ ID NOS: 13

<210> SEQ ID NO 1
<211> LENGTH: 19
<212> TYPE: PRT
<213> ORGANISM: Artificial Sequence
<220> FEATURE:
<223> OTHER INFORMATION: Synthetic Construct

<400> SEQUENCE: 1

Thr Phe Phe Tyr Gly Gly Ser Arg Gly Lys Arg Asn Asn Phe Lys Thr
1               5                   10                  15

Glu Glu Tyr


<210> SEQ ID NO 2
<211> LENGTH: 23
<212> TYPE: PRT
<213> ORGANISM: Artificial Sequence
<220> FEATURE:
<223> OTHER INFORMATION: Synthetic Construct

<400> SEQUENCE: 2

Thr Glu Glu Leu Arg Val Arg Leu Ala Ser His Leu Arg Lys Leu Arg
1               5                   10                  15

Lys Arg Leu Leu Arg Asp Ala
            20


<210> SEQ ID NO 3
<211> LENGTH: 18
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (18)..(18)
<223> OTHER INFORMATION: AMIDATION

<400> SEQUENCE: 3

Leu Arg Lys Leu Arg Lys Arg Leu Leu Leu Arg Lys Leu Arg Lys Arg
1               5                   10                  15

Leu Leu


<210> SEQ ID NO 4
<211> LENGTH: 38
<212> TYPE: PRT
<213> ORGANISM: Artificial Sequence
<220> FEATURE:
<223> OTHER INFORMATION: Synthetic Construct

<400> SEQUENCE: 4

Ser Val Ile Asp Ala Leu Gln Tyr Lys Leu Glu Gly Thr Thr Arg Leu
1               5                   10                  15

Thr Arg Lys Arg Gly Leu Lys Leu Ala Thr Ala Leu Ser Leu Ser Asn
            20                  25                  30
```

Lys Phe Val Glu Gly Ser
35

<210> SEQ ID NO 5
<211> LENGTH: 12
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (12)..(12)
<223> OTHER INFORMATION: AMIDATION

<400> SEQUENCE: 5

Thr His Arg Pro Pro Met Trp Ser Pro Val Trp Pro
1 5 10

<210> SEQ ID NO 6
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: ACETYLATION

<400> SEQUENCE: 6

Cys Met Pro Arg Leu Arg Gly Cys
1 5

<210> SEQ ID NO 7
<211> LENGTH: 20
<212> TYPE: PRT
<213> ORGANISM: Artificial Sequence
<220> FEATURE:
<223> OTHER INFORMATION: Synthetic Construct

<400> SEQUENCE: 7

Thr Trp Pro Lys His Phe Asp Lys His Thr Phe Tyr Ser Ile Leu Lys
1 5 10 15

Leu Gly Lys His
20

<210> SEQ ID NO 8
<211> LENGTH: 12
<212> TYPE: PRT
<213> ORGANISM: Artificial Sequence
<220> FEATURE:
<223> OTHER INFORMATION: Synthetic Construct

<400> SEQUENCE: 8

Thr Gly Asn Tyr Lys Ala Leu His Pro His Asn Gly
1 5 10

<210> SEQ ID NO 9
<211> LENGTH: 30
<212> TYPE: PRT
<213> ORGANISM: Artificial Sequence
<220> FEATURE:
<223> OTHER INFORMATION: Synthetic Construct

<400> SEQUENCE: 9

Tyr Gln Gln Ile Leu Thr Ser Met Pro Ser Arg Asn Val Ile Gln Ile
1 5 10 15

Ser Asn Asp Leu Glu Asn Leu Arg Asp Leu Leu His Val Leu
20 25 30

<210> SEQ ID NO 10
<211> LENGTH: 29
<212> TYPE: PRT
<213> ORGANISM: Artificial Sequence
<220> FEATURE:
<223> OTHER INFORMATION: Synthetic Construct

<400> SEQUENCE: 10

Tyr Thr Ile Trp Met Pro Glu Asn Pro Arg Pro Gly Thr Pro Cys Asp
1 5 10 15

Ile Phe Thr Asn Ser Arg Gly Lys Arg Ala Ser Asn Gly
20 25

<210> SEQ ID NO 11
<211> LENGTH: 36
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: ACETYLATION
<220> FEATURE:
<221> NAME/KEY: SITE
<222> LOCATION: (36)..(36)
<223> OTHER INFORMATION: PEG4-Cholesterol ester of isoleucine
<220> FEATURE:
<221> NAME/KEY: MOD_RES
<222> LOCATION: (36)..(36)
<223> OTHER INFORMATION: PEG4-Cholesterol ester of isoleucine

<400> SEQUENCE: 11

Val Ala Leu Asp Pro Ile Asp Ile Ser Ile Val Leu Asn Lys Ile Lys
1 5 10 15

Ser Asp Leu Glu Glu Ser Lys Glu Trp Ile Arg Arg Ser Asn Lys Ile
20 25 30

Leu Asp Ser Ile
35

<210> SEQ ID NO 12
<211> LENGTH: 32
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (32)..(32)
<223> OTHER INFORMATION: PEG4-Cholesterol ester of lysine

<400> SEQUENCE: 12

Val Asn Lys Lys Ile Glu Glu Ile Asp Lys Lys Ile Glu Glu Leu Asn
1 5 10 15

Lys Lys Leu Glu Glu Leu Glu Lys Lys Leu Glu Glu Val Asn Lys Lys
20 25 30

<210> SEQ ID NO 13
<211> LENGTH: 36
<212> TYPE: PRT

-continued

```
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (36)..(36)
<223> OTHER INFORMATION: PEG4-Cholesterol ester of arginine

<400> SEQUENCE: 13

Pro Pro Ile Ser Leu Glu Arg Leu Asp Val Gly Thr Asn Leu Gly Asn
1               5                   10                  15

Ala Ile Ala Lys Leu Glu Asp Ala Lys Glu Leu Leu Glu Ser Ser Asp
            20                  25                  30

Gln Ile Leu Arg
        35
```